US007807817B2

(12) United States Patent
Joyce et al.

(10) Patent No.: US 7,807,817 B2
(45) Date of Patent: *Oct. 5, 2010

(54) ENZYMATIC NUCLEIC ACID MOLECULES

(75) Inventors: Gerald F. Joyce, Encinitas, CA (US); Ronald R. Breaker, Guilford, CT (US)

(73) Assignee: The Scripps Research Institute, La Jolla, CA (US)

(*) Notice: Subject to any disclaimer, the term of this patent is extended or adjusted under 35 U.S.C. 154(b) by 735 days.

This patent is subject to a terminal disclaimer.

(21) Appl. No.: 11/605,177

(22) Filed: Nov. 28, 2006

(65) Prior Publication Data

US 2007/0219365 A1  Sep. 20, 2007

Related U.S. Application Data

(60) Division of application No. 09/423,035, filed as application No. PCT/US98/08677 on Apr. 29, 1998, now Pat. No. 7,141,665, said application No. 09/423,035 is a continuation-in-part of application No. 08/849,567, filed as application No. PCT/US95/15580 on Dec. 1, 1995, now Pat. No. 6,326,174, which is a continuation-in-part of application No. 08/472,194, filed on Jun. 7, 1995, now Pat. No. 5,807,718, and a continuation-in-part of application No. 08/349,023, filed on Dec. 2, 1994, now abandoned.

(60) Provisional application No. 60/045,228, filed on Apr. 29, 1997.

(51) Int. Cl.
*C07H 21/04* (2006.01)
*A61K 31/70* (2006.01)

(52) U.S. Cl. .................. 536/24.5; 514/44; 536/23.1
(58) Field of Classification Search .................. None
See application file for complete search history.

(56) References Cited

U.S. PATENT DOCUMENTS

| 5,861,288 A | 1/1999 | Usman et al. |
| 5,879,938 A | 3/1999 | Usman et al. |
| 5,998,203 A * | 12/1999 | Matulic-Adamic et al. .. 435/325 |
| 6,008,343 A | 12/1999 | Jennings et al. |
| 6,159,714 A | 12/2000 | Usman et al. |

FOREIGN PATENT DOCUMENTS

WO  WO95/11304  4/1995

OTHER PUBLICATIONS

Breaker, DNA enzymes, 1997, *Nature Biotech.*, 15:427-431.
Beaudry and Joyce, "Directed Evolution of an RNA Enzyme", *Science*, 257:635-641 (1992).
Breaker, et al., "Continuous in Vitro Evolution of Bacteriophage RNA Polymerase Promoters", *Biochemistry*, 33:11980-11986 (1994).
Breaker and Joyce, "Inventing and Improving Ribozyme Function: Rational Design Versus Iterative Selection Methods", *Trends Biotech*, 12:268-275 (1994).
Breaker and Joyce, "A DNA Enzyme with Mg2+-Dependent RNA Phosphoesterase Activity", *Chemistry & Biology*, 2:655-660 (1995).
Burgstaller and Famulok, "Synthetic Ribozymes and the First Deoxyribozyme", *Angew. Chem. Int. Ed. Engl.*, 34:1189-1192 (1995).
Cadwell and Joyce, "Randomization of Genes by PCR Mutagenesis", *PCR Methods and Applications*, 2:28-33 (1992).
Cadwell and Joyce, "Mutagenic PCR", *PCR Methods and Applications*, 3(Suppl): s136-s140 (1994).
Chartrand, et al., "A Oligodeoxyribonucleotide with Catalytic Properties", *Proc. RNA Society*, (1994) Abstract.
Joyce and Inoue, "A Novel Technique for the Rapid Preparation of Mutant RNAs", *Nucleic Acids Research*, 17:711-722 (1989).
Joyce, "Amplification, Mutation and Selection of Catalytic RNA", *Gene*, 82:83-87 (1989).
Joyce, "In Vitro Evolution of Nucleic Acids", *Current Opinion in Structural Biology*, 4:331-336 (1994).
Lehman and Joyce, "Evolution In Vitro of an RNA Enzyme with Altered Metal Dependence", *Nature*, 361:182-185 (1993).
Pan and Uhlenbeck, "In Vitro Selection of RNAs that Undergo Autolytic Cleavage with Pb2+", *Biochemistry*, 31:3887-3895 (1992).
Pan and Uhlenbeck, "A Small Metalloribozyme with a Two-Step Mechanism", *Nature*, 358:560-563 (1992).
Paquette, et al., "The Conformation of Single-Stranded Nucleic Acids tDNA Versus tRNA". *Eur. J. Biochem.*, 189:259-265 (1990).
Perreault, et al., "Mixed Deoxyribo- and Ribo-oligonucleotides with Catalytic Activity", *Nature*, 344:565-567 (1990).
Robertson and Joyce, "Selection In Vitro of an RNA Enzyme that Specifically Cleaves Single-Stranded DNA", *Nature*, 344:467-468 (1990).
Tsang and Joyce, "Evolutionary Optimization of the Catalytic Properties of a DNA-Cleaving Ribozyme", *Biochemistry*, 33:5966-5973 (1994).
Williams, et al., "Function of Specific 2'-Hydroxyl Groups of Guanosines in a Hammerhead Ribozyme Probed by 2' Modifications", *Proc. Natl. Acad. Sci., USA*, 89:918-921 (1992).
Yang, et al., "Minimum Ribonucleotide Requirement for Catalysis by the RNA Hammerhead Domain", *Biochemistry*, 31:5005-5009 (1992).

* cited by examiner

*Primary Examiner*—Tracy Vivlemore
(74) *Attorney, Agent, or Firm*—Hugh Wang; Thomas Fitting

(57) ABSTRACT

The present invention discloses nucleic acid enzymes and deoxyribonucleic acid enzymes capable of cleaving nucleic acid sequences or molecules, particularly RNA, in a site-specific manner, as well as compositions including same. Methods of making and using the disclosed enzymes and compositions are also disclosed.

38 Claims, 12 Drawing Sheets

FIG. 3

HIV-1 *gag-pol* substrate 2 mM $Mg^{2+}$, 150 mM NaCl, pH 7.5, 37 °C

HIV-1 *gag-pol* substrate 2 mM $Mg^{2+}$, 150 mM NaCl, pH 7.5, 37 °C

ENZYMATIC NUCLEIC ACID MOLECULES

This application is a divisional of and claims priority to application Ser. No. 09/423,035, filed Jan. 13, 2000, now issued now U.S. Pat. No. 7,141,665, which is a U.S. National Stage of and claims priority to International Patent Application No. PCT/US98/08677, filed Apr. 29, 1998, published, which is a non-provisional and claims priority to Application Ser. No. 60/045,228, filed Apr. 29, 1997, now abandoned. Application Ser. No. 09/423,035 is a continuation-in part and claims priority to application Ser. No. 08/849,567, filed Aug. 25, 1997, now issued now U.S. Pat. No. 6,326,174, which is a U.S. National Stage of and claims priority to International Patent Application No. PCT/US95/15580 filed Dec. 1, 1995, published, which is a continuation-in-part of and claims priority to application Ser. No. 08/472,194, filed Jun. 7, 1995, now issued now U.S. Pat. No. 5,807,718 and application Ser. No. 08/349,023, filed Dec. 2, 1994, now abandoned.

TECHNICAL FIELD

The present invention relates to nucleic acid enzymes or catalytic (enzymatic) DNA molecules that are capable of cleaving other nucleic acid molecules, particularly RNA. The present invention also relates to compositions containing the disclosed enzymatic DNA molecules and to methods of making and using such enzymes and compositions.

BACKGROUND

The need for catalysts that operate outside of their native context or which catalyze reactions that are not represented in nature has resulted in the development of "enzyme engineering" technology. The usual route taken in enzyme engineering has been a "rational design" approach, relying upon the understanding of natural enzymes to aid in the construction of new enzymes. Unfortunately, the state of proficiency in the areas of protein structure and chemistry is insufficient to make the generation of novel biological catalysts routine.

Recently, a different approach for developing novel catalysts has been applied. This method involves the construction of a heterogeneous pool of macromolecules and the application of an in vitro selection procedure to isolate molecules from the pool that catalyze the desired reaction. Selecting catalysts from a pool of macromolecules is not dependent on a comprehensive understanding of their structural and chemical properties. Accordingly, this process has been dubbed "irrational design" (Brenner et al., *Proc. Natl. Acad. Sci. USA*, 89:5381-5383, 1992).

Most efforts to date involving the rational design of enzymatic RNA molecules or ribozymes have not led to molecules with fundamentally new or improved catalytic function. However, the application of irrational design methods via a process we have described as "directed molecular evolution" or "in vitro evolution", which is patterned after Darwinian evolution of organisms in nature, has the potential to lead to the production of DNA molecules that have desirable functional characteristics.

This technique has been applied with varying degrees of success to RNA molecules in solution (see, e.g., Mills et al, *Proc. Natl. Acad. Sci. USA*, 58:217, 1967; Green et al, *Nature*, 347:406, 1990; Chowrira et al, *Nature*, 354:320, 1991; Joyce, *Gene*, 82:83, 1989; Beaudry et al, *Science*, 257:635-641, 1992; Robertson et al, *Nature*, 344:467, 1990), as well as to RNAs bound to a ligand that is attached to a solid support (Tuerk et al, *Science*, 249:505, 1990; Ellington et al, *Nature*, 346:818, 1990). It has also been applied to peptides attached directly to a solid support (Lam et al, *Nature*, 354:82, 1991); and to peptide epitopes expressed within a viral coat protein (Scott et al, *Science*, 249:386, 1990; Devlin et al, *Science*, 249:249, 1990; Cwirla et al, *Proc. Natl. Acad. Sci. USA*, 87:6378, 1990).

It has been more than a decade since the discovery of catalytic RNA (Kruger et al, *Cell*, 31:147-157, 1982; Guerrier-Takada et al, *Cell*, 35:849-857, 1983). The list of known naturally-occurring ribozymes continues to grow (see Cech, in *The RNA World*, Gesteland & Atkins (eds.), pp. 239-269, Cold Spring Harbor Laboratory Press, Cold Spring Harbor, N.Y. (1993); Pyle, *Science*, 261:709-714, 1993; Symons, *Curr. Opin. Struct. Biol.*, 4:322-330, 1994) and, in recent years, has been augmented by synthetic ribozymes obtained through in vitro evolution. (See Joyce, *Curr. Opin. Struct. Biol.*, 4:331-336, 1994; Breaker et al, *Trends Biotech.*, 12:268-275, 1994; Chapman et al, *Curr. Opin. Struct. Biol.*, 4:618-622, 1994).

It seems reasonable to assume that DNA can have catalytic activity as well, considering that it contains most of the same functional groups as RNA. However, with the exception of certain viral genomes and replication intermediates, nearly all of the DNA in biological organisms occurs as a complete duplex, precluding it from adopting a complex secondary and tertiary structure. Thus it is not surprising that DNA enzymes have not been found in nature.

Until the advent of the present invention, the design, synthesis and use of catalytic DNA molecules with nucleotide-cleaving capabilities has not been disclosed or demonstrated. Therefore, the discoveries and inventions disclosed herein are particularly significant, in that they highlight the potential of in vitro evolution as a means of designing increasingly more efficient catalytic molecules, including enzymatic DNA molecules that cleave other nucleic acids, particularly RNA.

BRIEF SUMMARY OF THE INVENTION

The present invention describes a synthetic or engineered (i.e., non-naturally-occurring) catalytic DNA molecule (or enzymatic DNA molecule) capable of cleaving a substrate nucleic acid (NA) sequence at a defined cleavage site. The invention also contemplates an enzymatic DNA molecule having an endonuclease activity.

A preferred catalytic DNA molecule has site-specific endonuclease activity specific for a nucleotide sequence defining a cleavage site in a preselected substrate nucleic acid sequence. The DNA molecule has first and second substrate binding regions flanking a core region, wherein the first substrate binding region has a sequence complementary to a first portion of the preselected substrate nucleic acid sequence, and the second substrate binding region has a sequence complementary to a second portion of the preselected substrate nucleic acid sequence. The core region has a sequence according to the formula:

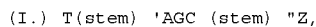

(I.) T(stem) 'AGC (stem) "Z, wherein the (stem)' and (stem)" are each three sequential nucleotides which when hybridized as a (stem)':(stem)" pair comprise three base pairs including at least two G:C pairs and wherein Z=WCGR or WCGAA, and W=A or T and R=A or G. In a preferred embodiment, formula I defines SEQ ID NO 120 (8-17).

Also contemplated is a core region having a sequence according to the formula:

(II.) RGGCTAGCXACAACGA (SEQ ID NO ), wherein X=T, C or A, and R=A or G. In a preferred embodiment, formula I defines SEQ ID NO 121 (10-23).

In another embodiment, the endonuclease activity is specific for a nucleotide sequence defining a cleavage site comprising single-stranded nucleic acid in a substrate nucleic acid sequence. In another preferred variation, the cleavage site is double-stranded nucleic acid. Similarly, substrate nucleic acid sequences may be single-stranded, double-stranded, partially single- or double-stranded, looped, or any combination thereof.

In another contemplated embodiment, the substrate nucleic acid sequence includes one or more nucleotide analogues. In one variation, the substrate nucleic acid sequence is a portion of, or attached to, a larger molecule.

In various embodiments, the larger molecule is selected from the group consisting of RNA, modified RNA, DNA, modified DNA, nucleotide analogs, or composites thereof. In another example, the larger molecule comprises a composite of a nucleic acid sequence and a non-nucleic acid sequence.

In another embodiment, the invention contemplates that a substrate nucleic acid sequence includes one or more nucleotide analogs. A further variation contemplates that the single stranded nucleic acid comprises RNA, DNA, modified RNA, modified DNA, one or more nucleotide analogs, or any composite thereof. In one embodiment of the disclosed invention, the endonuclease activity comprises hydrolytic cleavage of a phosphoester bond at the cleavage site.

In various preferred embodiments, the catalytic DNA molecules of the present invention are single-stranded in whole or in part. These catalytic DNA molecules may preferably assume a variety of shapes consistent with their catalytic activity. Thus, in one variation, a catalytic DNA molecule of the present invention includes one or more hairpin loop structures. In yet another variation, a catalytic DNA molecule may assume a shape similar to that of "hammerhead" ribozymes. In still other embodiments, a catalytic DNA molecule may assume a conformation similar to that of *Tetrahymena thermophila* ribozymes, e.g., those derived from group I introns.

Similarly, preferred catalytic DNA molecules of the present invention are able to demonstrate site-specific endonuclease activity irrespective of the original orientation of the substrate molecule. Thus, in one preferred embodiment, an enzymatic DNA molecule of the present invention is able to cleave a substrate nucleic acid sequence that is separate from the enzymatic DNA molecule—i.e., it is not linked to the DNAzyme. In another preferred embodiment, an enzymatic DNA molecule is able to cleave an attached substrate nucleic acid sequence—i.e., it is able to perform a reaction similar to self-cleavage.

The invention also contemplates enzymatic DNA molecules (catalytic DNA molecules, deoxyribozymes or DNAzymes) having endonuclease activity, whereby the endonuclease activity requires the presence of a divalent cation. In various preferred, alternative embodiments, the divalent cation is selected from the group consisting of $Pb^{2+}$, $Mg^{2+}$, $Mn^{2+}$, $Zn^{2+}$, and $Ca^{2+}$. Another variation contemplates that the endonuclease activity requires the presence of a monovalent cation. In such alternative embodiments, the monovalent cation is preferably selected from the group consisting of $Na^+$ and $K^+$.

In various preferred embodiments of the invention, an enzymatic DNA molecule comprises a nucleotide sequence selected from the group consisting of SEQ ID NO 3, SEQ ID NO 14; SEQ ID NO 15; SEQ ID NO 16; SEQ ID NO 17; SEQ ID NO 18; SEQ ID NO 19; SEQ ID NO 20; SEQ ID NO 21; and SEQ ID NO 22. In other preferred embodiments, a catalytic DNA molecule of the present invention comprises a nucleotide sequence selected from the group consisting of SEQ ID NO 23; SEQ ID NO 24; SEQ ID NO 25; SEQ ID NO 26; SEQ ID NO 27; SEQ ID NO 28; SEQ ID NO 29; SEQ ID NO 30; SEQ ID NO 31; SEQ ID NO 32; SEQ ID NO 33; SEQ ID NO 34; SEQ ID NO 35; SEQ ID NO 36; SEQ ID NO 37; SEQ ID NO 38; and SEQ ID NO 39.

Another preferred embodiment contemplates that a catalytic DNA molecule of the present invention comprises a nucleotide sequence selected from the group consisting of SEQ ID NO 50 and SEQ ID NO 51. In yet another preferred embodiment, a catalytic DNA molecule of the present invention comprises a nucleotide sequence selected from the group consisting of SEQ ID NOS 52 through 101. As disclosed herein, catalytic DNA molecules having sequences substantially similar to those disclosed herein are also contemplated. Thus, a wide variety of substitutions, deletions, insertions, duplications and other mutations may be made to the within-described molecules in order to generate a variety of other useful enzymatic DNA molecules; as long as said molecules display site-specific cleavage activity as disclosed herein, they are within the boundaries of this disclosure.

In a further variation of the present invention, an enzymatic DNA molecule of the present invention preferably has a substrate binding affinity of about 1 μM or less. In another embodiment, an enzymatic DNA molecule of the present invention binds substrate with a $K_D$ of less than about 0.1 μM.

The present invention also discloses enzymatic DNA molecules having useful turnover rates. In one embodiment, the turnover rate is less than 5 $hr^{-1}$; in a preferred embodiment, the rate is less than about 2 $hr^{-1}$; in a more preferred embodiment, the rate is less than about 1 $hr^{-1}$; in an even more preferred embodiment, the turnover rate is about 0.6 $hr^{-1}$ or less.

In still another embodiment, an enzymatic DNA molecule of the present invention displays a useful turnover rate wherein the $k_{obs}$ is less than 1 $min^{-1}$, preferably less than 0.1 $min^{-1}$; more preferably, less than 0.01 $min^{-1}$; and even more preferably, less than 0.005 $min^{-1}$. In one variation, the value of $k_{obs}$ is approximately 0.002 $min^{-1}$ or less.

The present invention also contemplates embodiments in which the catalytic rate of the disclosed DNA enzymes is fully optimized. Thus, in various preferred embodiments, the $K_m$ for reactions enhanced by the presence of $Mg^{2+}$ is approximately 0.5-20 mM, preferably about 1-10 mM, and more preferably about 2-5 mM.

The present invention also contemplates an embodiment whereby the nucleotide sequence defining the cleavage site comprises at least one nucleotide. In various other preferred embodiments, a catalytic DNA molecule of the present invention is able to recognize and cleave a nucleotide sequence defining a cleavage site of two or more nucleotides.

In various preferred embodiments, an enzymatic DNA molecule of the present invention comprises a conserved core flanked by one or more substrate binding regions. In one embodiment, an enzymatic DNA molecule includes first and second substrate binding regions. In another embodiment, an enzymatic DNA molecule includes two or more substrate binding regions.

As noted previously, preferred catalytic DNA molecules of the present invention may also include a conserved core. In one preferred embodiment, the conserved core comprises one or more conserved regions. In other preferred variations, the one or more conserved regions include a nucleotide sequence selected from the group consisting of CG; CGA; AGCG; AGCCG; CAGCGAT; CTTGTTT; and CTTATTT (see, e.g., FIG. 3).

In one embodiment of the invention, an enzymatic DNA molecule of the present invention further comprises one or more variable or spacer nucleotides between the conserved regions in the conserved core. In another embodiment, an enzymatic DNA molecule of the present invention further comprises one or more variable or spacer nucleotides between the conserved core and the substrate binding region.

In one variation, the first substrate binding region preferably includes a nucleotide sequence selected from the group consisting of CATCTCT; GCTCT; TTGCTTTTT; TGTCTTCTC; TTGCTGCT; GCCATGCTTT (SEQ ID NO 40); CTCTATTTCT (SEQ ID NO 41); GTCGGCA; CATCTCTTC; and ACTTCT. In another preferred variation, the second substrate binding region includes a nucleotide sequence selected from the group consisting of TATGTGACGCTA (SEQ ID NO 42); TATAGTCGTA (SEQ ID NO 43); ATAGCGTATTA (SEQ ID NO 44); ATAGTTACGTCAT (SEQ ID NO 45); AATAGTGAAGTGTT (SEQ ID NO 46); TATAGTGTA; ATAGTCGGT; ATAGGCCCGGT (SEQ ID NO 47); AATAGTGAGGCTTG (SEQ ID NO 48); and ATGNTG.

In various embodiments of the present invention, the substrate binding regions vary in length. Thus, for example, a substrate binding region may comprise a single nucleotide to dozens of nucleotides. However, it is understood that substrate binding regions of about 3-25 nucleotides in length, preferably about 3-15 nucleotides in length, and more preferably about 3-10 nucleotides in length are particularly preferred. In various embodiments, the individual nucleotides in the substrate binding regions are able to form complementary base pairs with the nucleotides of the substrate molecules; in other embodiments, noncomplementary base pairs are formed. A mixture of complementary and noncomplementary base pairing is also contemplated as falling within the scope of the disclosed embodiments of the invention.

In another preferred embodiment, a catalytic DNA molecule of the present invention may further comprise a third substrate binding region. In some preferred embodiments, the third region includes a nucleotide sequence selected from the group consisting of TGTT; TGTTA; and TGTTAG. Another preferred embodiment of the present invention discloses an enzymatic DNA molecule further comprising one or more variable or "spacer" regions between the substrate binding regions.

In another disclosed embodiment, the present invention contemplates a purified, synthetic enzymatic DNA molecule separated from other DNA molecules and oligonucleotides, the enzymatic DNA molecule having an endonuclease activity, wherein the endonuclease activity is specific for a nucleotide sequence defining a cleavage site comprising single- or double-stranded nucleic acid in a substrate nucleic acid sequence. In one variation, a synthetic (or engineered) enzymatic DNA molecule having an endonuclease activity is disclosed, wherein the endonuclease activity is specific for a nucleotide sequence defining a cleavage site consisting essentially of a single- or double-stranded region of a substrate nucleic acid sequence.

In yet another embodiment, the invention contemplates an enzymatic DNA molecule comprising a deoxyribonucleotide polymer having a catalytic activity for hydrolyzing a nucleic acid-containing substrate to produce substrate cleavage products. In one variation, the hydrolysis takes place in a site-specific manner. As noted previously, the polymer may be single-stranded, double-stranded, or some combination of both.

The invention further contemplates that the substrate comprises a nucleic acid sequence. In various embodiments, the nucleic acid sequence substrate comprises RNA, modified RNA, DNA, modified DNA, one or more nucleotide analogs, or composites of any of the foregoing. One embodiment contemplates that the substrate includes a single-stranded segment; still another embodiment contemplates that the substrate is double-stranded.

The present invention also contemplates an enzymatic DNA molecule comprising a deoxyribonucleotide polymer having a catalytic activity for hydrolyzing a nucleic acid-containing substrate to produce a cleavage product. In one variation, the enzymatic DNA molecule has an effective binding affinity for the substrate and lacks an effective binding affinity for the cleavage product.

In one preferred embodiment, the invention discloses a non-naturally-occurring enzymatic DNA molecule comprising a nucleotide sequence defining a conserved core flanked by recognition domains, variable regions, and spacer regions. Thus, in one preferred embodiment, the nucleotide sequence defines a first variable region contiguous or adjacent to the 5'-terminus of the molecule, a first recognition domain located 3'-terminal to the first variable region, a first spacer region located 3'-terminal to the first recognition domain, a first conserved region located 3'-terminal to the first spacer region, a second spacer region located 3'-terminal to the first conserved region, a second conserved region located 3'-terminal to the second spacer region, a second recognition domain located 3'-terminal to the second conserved region, and a second variable region located 3'-terminal to the second recognition domain.

In another embodiment, the nucleotide sequence preferably defines a first variable region contiguous or adjacent to the 5'-terminus of the molecule, a first recognition domain located 3'-terminal to the first variable region, a first spacer region located 3'-terminal to the first recognition domain, a first conserved region located 3'-terminal to the first spacer region, a second spacer region located 3'-terminal to the first conserved region, a second conserved region located 3'-terminal to the second spacer region, a second recognition domain located 3'-terminal to the second conserved region, a second variable region located 3'-terminal to the second recognition domain, and a third recognition domain located 3'-terminal to the second variable region.

In one variation of the foregoing, the molecule includes a conserved core region flanked by two substrate binding domains; in another, the conserved core region comprises one or more conserved domains. In other preferred embodiments, the conserved core region further comprises one or more variable or spacer nucleotides. In yet another embodiment, an enzymatic DNA molecule of the present invention further comprises one or more spacer regions.

The present invention further contemplates a wide variety of compositions. For example, compositions including an enzymatic DNA molecule as described hereinabove are disclosed and contemplated herein. In one alternative embodiment, a composition according to the present invention comprises two or more populations of enzymatic DNA molecules as described above, wherein each population of enzymatic DNA molecules is capable of cleaving a different sequence in a substrate. In another variation, a composition comprises two or more populations of enzymatic DNA molecules as described hereinabove, wherein each population of enzymatic DNA molecules is capable of recognizing a different substrate. In various embodiments, it is also preferred that compositions include a monovalent or divalent cation.

The present invention further contemplates methods of generating, selecting, and isolating enzymatic DNA molecules of the present invention. In one variation, a method of selecting enzymatic DNA molecules that cleave a nucleic acid sequence (e.g., RNA) at a specific site comprises the following steps: (a) obtaining a population of putative enzymatic DNA molecules—whether the sequences are naturally-occurring or synthetic—and preferably, they are single-stranded DNA molecules; (b) admixing nucleotide-containing substrate sequences with the aforementioned population of DNA molecules to form an admixture; (c) maintaining the admixture for a sufficient period of time and under predetermined reaction conditions to allow the putative enzymatic DNA molecules in the population to cause cleavage of the substrate sequences, thereby producing substrate cleavage products; (d) separating the population of DNA molecules from the substrate sequences and substrate cleavage products; and (e) isolating DNA molecules that cleave substrate nucleic acid sequences (e.g., RNA) at a specific site from the population.

In a further variation of the foregoing method, the DNA molecules that cleave substrate nucleic acid sequences at a specific site are tagged with an immobilizing agent. In one example, the agent comprises biotin.

In yet another variation of the aforementioned method, one begins by selecting a sequence—e.g., a predetermined "target" nucleotide sequence—that one wishes to cleave using an enzymatic DNA molecule engineered for that purpose. Thus, in one embodiment, the pre-selected (or predetermined) "target" sequence is used to generate a population of DNA molecules capable of cleaving substrate nucleic acid sequences at a specific site via attaching or "tagging" it to a deoxyribonucleic acid sequence containing one or more randomized sequences or segments. In one variation, the randomized sequence is about 40 nucleotides in length; in another variation, the randomized sequence is about 50 nucleotides in length. Randomized sequences that are 1-40, 40-50, and 50-100 nucleotides in length are also contemplated by the present invention.

In one embodiment of the present invention, the nucleotide sequence used to generate a population of enzymatic DNA molecules is selected from the group consisting of SEQ ID NO 4, 23, 50 AND 51. In another embodiment, the "target" or "substrate" nucleotide sequence comprises a sequence of one or more ribonucleotides—see, e.g., the relevant portions of SEQ ID NOS 4 and 23, and SEQ ID NO 49. It is also contemplated by the present invention that a useful "target" or "substrate" nucleotide sequence may comprise DNA, RNA, or a composite thereof.

The invention also contemplates methods as described above, wherein the isolating step further comprises exposing the tagged DNA molecules to a solid surface having avidin linked thereto, whereby the tagged DNA molecules become attached to the solid surface. As before, the substrate may be RNA, DNA, a composite of both, or a molecule including nucleotide sequences.

The present invention also contemplates a method for specifically cleaving a substrate nucleic acid sequence at a particular cleavage site, comprising the steps of (a) providing an enzymatic DNA molecule capable of cleaving a substrate nucleic acid sequence at a specific cleavage site; and (b) contacting the enzymatic DNA molecule with the substrate nucleic acid sequence to cause specific cleavage of the nucleic acid sequence at the cleavage site. In one variation, the enzymatic DNA molecule is a non-naturally-occurring (or synthetic) DNA molecule. In another variation, the enzymatic DNA molecule is single-stranded.

In still another variation of the foregoing method, the substrate comprises a nucleic acid. In various embodiments, the substrate nucleic acid comprises RNA, modified RNA, DNA, modified DNA, one or more nucleotide analogs, or composites of any of the foregoing. In yet another embodiment, the specific cleavage is caused by the endonuclease activity of the enzymatic DNA molecule. Alteration of reaction conditions—e.g., the adjustment of pH, temperature, percent cation, percent enzyme, percent substrate, and percent product—is also contemplated herein.

The present invention also contemplates a method of cleaving a phosphoester bond, comprising (a) admixing an catalytic DNA molecule capable of cleaving a substrate nucleic acid sequence at a defined cleavage site with a phosphoester bond-containing substrate, to form a reaction admixture; and (b) maintaining the admixture under predetermined reaction conditions to allow the enzymatic DNA molecule to cleave the phosphoester bond, thereby producing a population of substrate products. In one embodiment, the enzymatic DNA molecule is able to cleave the phosphoester bond in a site-specific manner. In another embodiment, the method further comprises the steps of (c) separating the products from the catalytic DNA molecule; and (d) adding additional substrate to the enzymatic DNA molecule to form a new reaction admixture.

The present invention also contemplates methods of engineering enzymatic DNA molecules that cleave phosphoester bonds. One exemplary method comprises the following steps: (a) obtaining a population of single-stranded DNA molecules; (b) introducing genetic variation into the population to produce a variant population; (c) selecting individuals from the variant population that meet predetermined selection criteria; (d) separating the selected individuals from the remainder of the variant population; and (e) amplifying the selected individuals.

BRIEF DESCRIPTION OF THE DRAWINGS

FIG. 3 illustrates the sequence alignment of individual variants isolated from the population after five rounds of selection. The fixed substrate domain is shown at the top, with the target riboadenylate identified via an inverted triangle (SEQ ID NO 13). Substrate nucleotides that are commonly involved in presumed base-pairing interactions are indicated by vertical bars. Sequences corresponding to the 50 initially-randomized nucleotides are aligned antiparallel to the substrate domain. All of the variants are 3'-terminated by the fixed sequence 5'-CGGTAAGCTTGGCAC-3' (not shown; SEQ ID NO 1). Nucleotides within the initially-randomized region that are presumed to form base pairs with the substrate domain are indicated on the right and left sides of the Figure; the putative base-pair-forming regions of the enzymatic DNA molecules are individually boxed in each sequence shown. Conserved regions are illustrated via the two large, centrally-located boxes.

FIG. 4A is a diagrammatic representation of the complex formed between the 19mer substrate (5[3]'-TCACTATrAGGAAGAGATGG-3[5]', SEQ ID NO 2) and 38mer DNA enzyme (5'-ACACATCTCT-GAAGTAGCGCCGCCGTATAGTGACGCTA-3', SEQ ID NO 3). The substrate contains a single adenosine ribonucleotide ("rA", adjacent to the arrow), flanked by deoxyribonucleotides. The synthetic DNA enzyme is a 38-nucleotide portion of the most frequently occurring variant shown in FIG. 3. Highly-conserved nucleotides located within the putative catalytic domain are "boxed". As illustrated, one conserved sequence is "AGCG", while another is "CG" (reading in the 5'-3' direction).

FIG. 4B shows an Eadie-Hofstee plot used to determine $K_m$ (negative slope) and $V_{max}$ (y-intercept) for DNA-catalyzed cleavage of [5'-$^{32}$P]-labeled substrate under conditions identical to those employed during in vitro selection. Initial rates of cleavage were determined for reactions involving 5 nM DNA enzyme and either 0.125, 0.5, 1, 2, or 4 µM substrate.

As noted, there are three lanes within each of the aforementioned four groups. In each group of three lanes, the first lane shows the lack of activity of the selected population in the absence of the metal cation, the second lane shows the observed activity in the presence of the metal cation, and the third lane shows the lack of activity of the starting pool (G0).

Figure 6A:
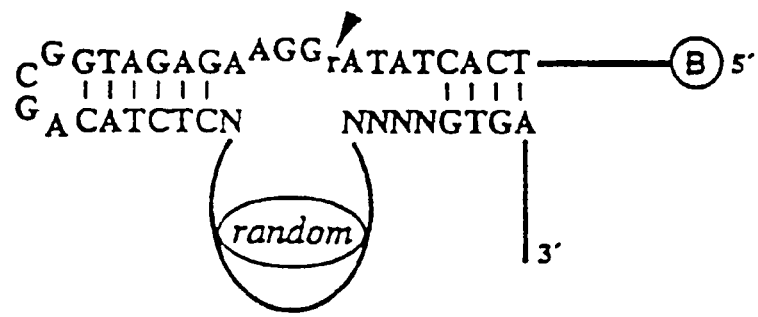
Figure 6B:
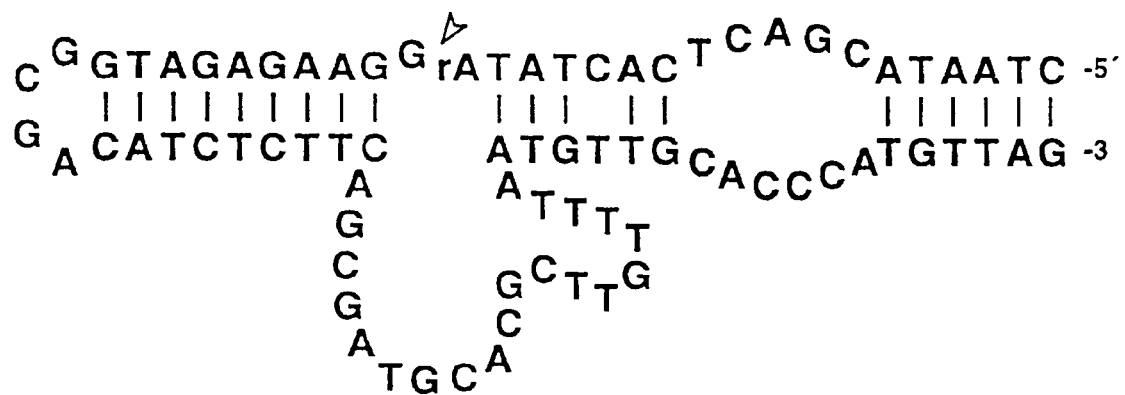

FIGS. 6A and 6B provide two-dimensional illustrations of a "progenitor" catalytic DNA molecule and one of several catalytic DNA molecules obtained via the selective amplification methods disclosed herein, respectively. FIG. 6A illustrates an exemplary molecule from the starting pool, showing the overall configuration of the molecules represented by SEQ ID NO 133. As illustrated, various complementary nucleotides flank the random ($N_{40}$) (SEQ ID NO 143) region. FIG. 6B is a diagrammatic representation of one of the $Mg^{2+}$-dependent catalytic DNA molecules (or "DNAzymes") (SEQ ID NO 123) generated via the within-described procedures. The location of the ribonucleotide in the substrate nucleic acid is indicated via the arrow in both FIGS. 6A and 6B.

Figure 7:
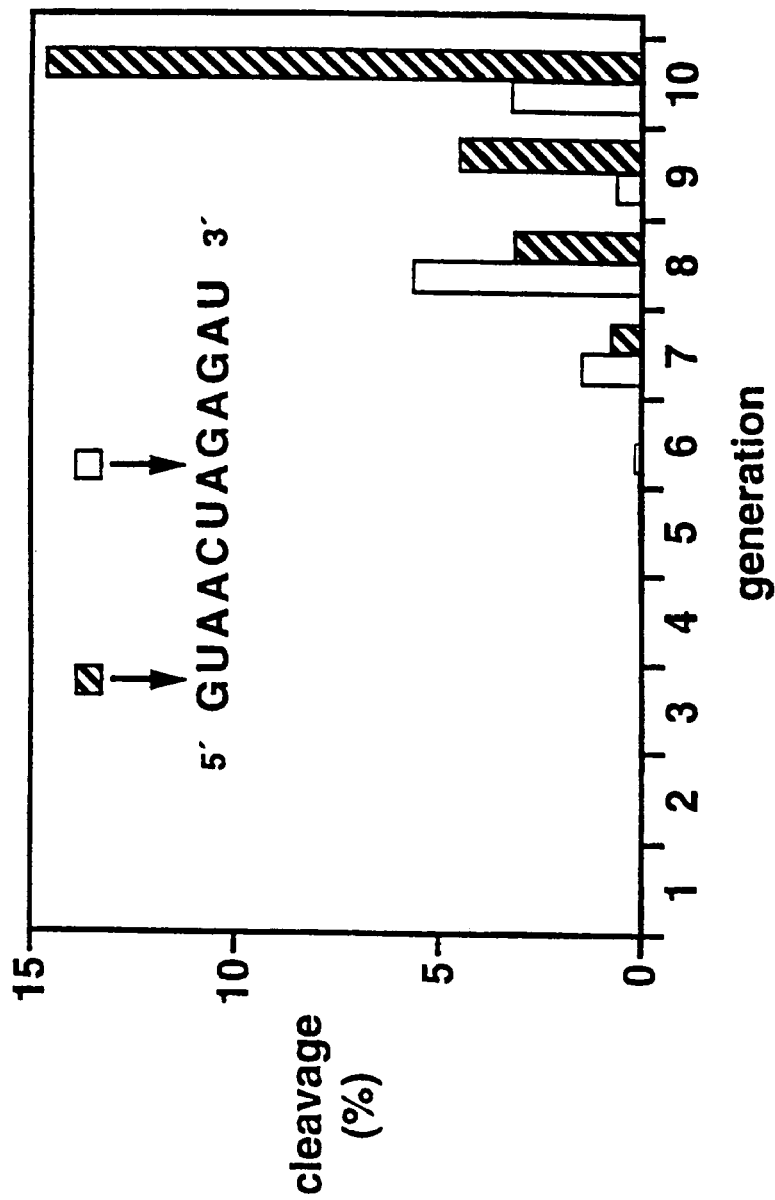

FIG. 7 illustrates some of the results of ten rounds of in vitro selective amplification carried out essentially as described in Example 5 hereinbelow. As shown, two sites and two families of catalysts emerged as displaying the most efficient cleavage of the target sequence. Cleavage conditions were essentially as indicated in FIG. 7, namely, 10 nM $Mg^{2+}$, pH 7.5, and 37° C.; data collected after the reaction ran for 2 hours is shown. Cleavage (%) is shown plotted against the number of generations (here, 0 through 10). The number/prevalence of catalytic DNA molecules capable of cleaving the target sequence at the indicated sites in the substrate is illustrated via the vertical bars, with cleavage at G↓UAACUAGAGAU shown by the striped bars, and with cleavage at GUAACUA↓GAGAU illustrated via the open (lightly-shaded) bars.

Figure 8:
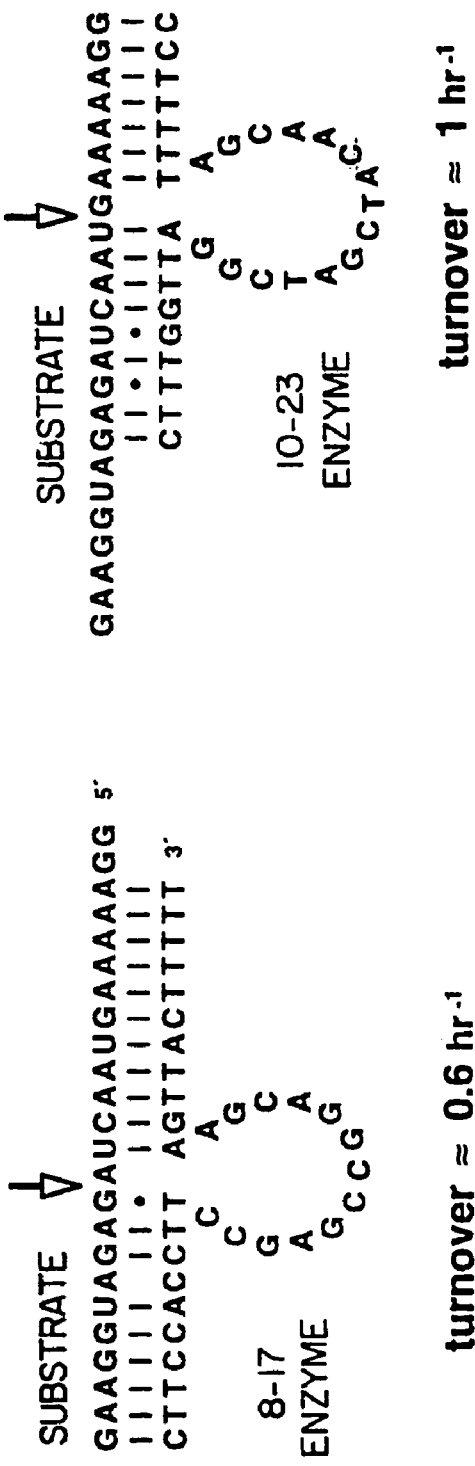

FIG. 8 illustrates the nucleotide sequences, cleavage sites, and turnover rates of two catalytic DNA molecules of the present invention, clones 8-17 (SEQ ID NO 134) and 10-23 (SEQ ID NO 136). Reaction conditions were as shown, namely, 10 mM $Mg^{2+}$, pH 7.5, and 37° C. The DNAzyme identified as clone 8-17 is illustrated on the left, with the site of cleavage of the RNA substrate indicated by the arrow. The substrate sequence (5',-GGAAAAAGUAACUAGAGAUG-GAAG-3' (SEQ ID NO 135))—which is separate from the DNAzyme (i.e., intermolecular cleavage is shown)—is labeled as such. Similarly, the DNAzyme identified herein as 10-23 is shown on the right, with the site of cleavage of the RNA substrate indicated by the arrow. Again, the substrate sequence is indicated (SEQ ID NO 135). For the 8-17 enzyme, the turnover rate was approximately 0.6 $hr^{-1}$; for the 10-23 enzyme, the turnover rate was approximately 1 $hr^{-1}$. Noncomplementary pairings are indicated with a closed circle (●), whereas complementary pairings are indicated with a vertical line (|).

Figure 9:
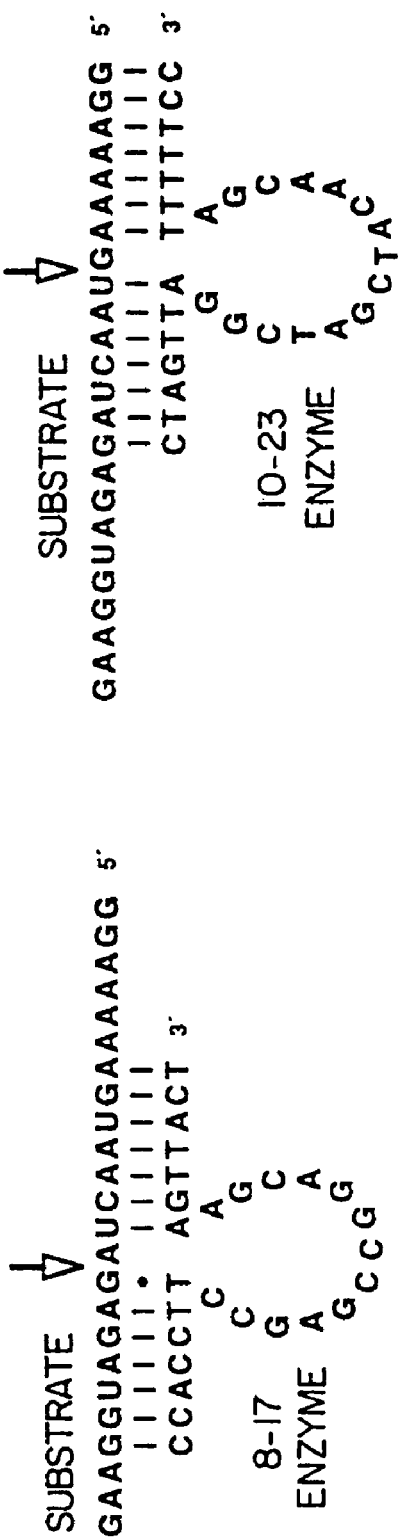

FIG. 9 further illustrates the nucleotide sequences, cleavage sites, and turnover rates of two catalytic DNA molecules of the present invention, clones 8-17 (SEQ ID NO 138) and 10-23 (SEQ ID NO 137). Reaction conditions were as shown, namely, 10 mM $Mg^{2+}$, pH 7.5, and 37° C. As in FIG. 8, the DNAzyme identified as clone 8-17 is illustrated on the left, with the site of cleavage of the RNA substrate indicated by the arrow. The substrate sequence (5'-GGAAAAAGUAACUA-GAGAUGGAAG-3' (SEQ ID NO 135))—which is separate from the DNAzyme (i.e., intermolecular cleavage is shown)—is labeled as such. Similarly, the DNAzyme identified herein as 10-23 is shown on the right, with the site of cleavage of the RNA substrate indicated by the arrow. Again, the substrate sequence is indicated (SEQ ID NO 135). For the 8-17 enzyme, $k_{obs}$ was approximately 0.002 $min^{-1}$; for the 10-23 enzyme, the value of $k_{obs}$ was approximately 0.01 $min^{-1}$. Noncomplementary pairings are indicated with a closed circle (●), whereas complementary pairings are indicated with a vertical line (|).

Figure 10:
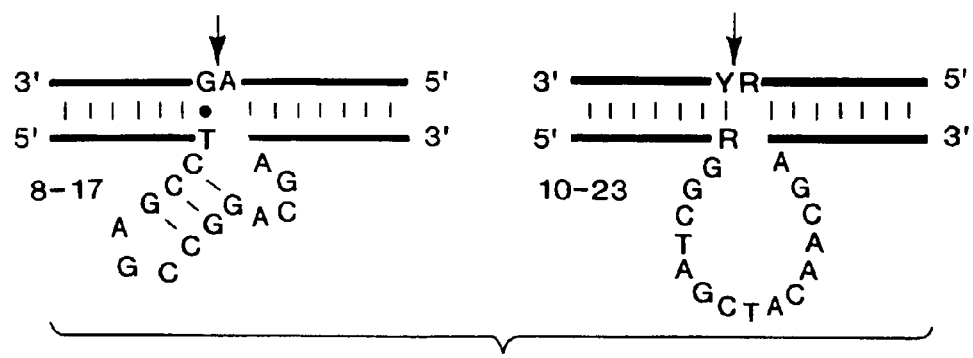

FIG. 10 illustrates a schematic showing the composition of the 8-17 and 10-23 catalytic motifs, SEQ ID NO 151 and SEQ ID NO:152, respectively. The DNA enzyme (bottom strand) binds the RNA substrate (top strand) through complementary Watson-Crick pairing (vertical lines) between unspecified complementary nucleotides (horizontal lines). Cleavage occurs at the position indicated by the arrow, where R=A or G and Y=U or C. The sequences 5'-TCCGAGCCGGACGA-3' (SEQ ID NO 120) and 5'-RGGCTAGCTACAACGA-3' (SEQ ID NO 121) are shown.

Figure 11:
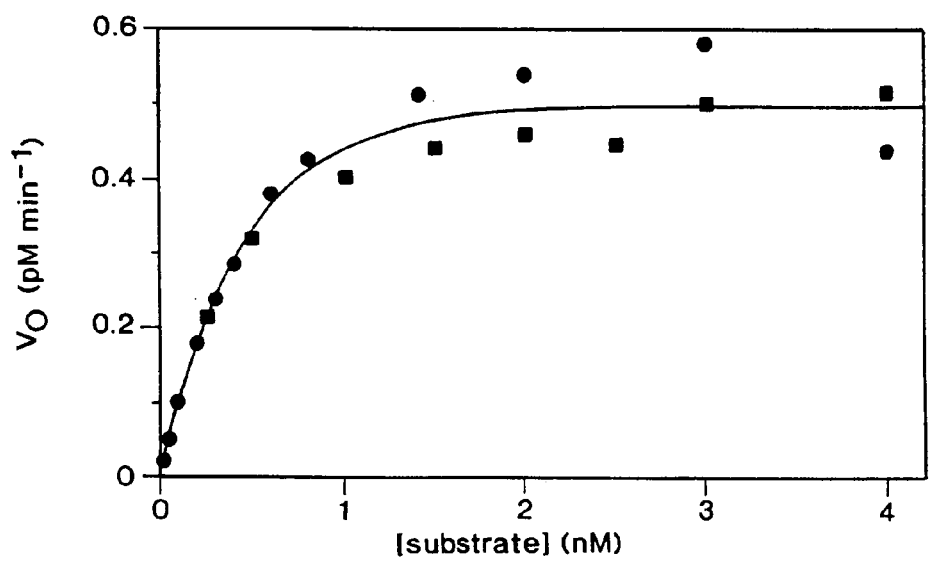

FIG. 11 illustrates the catalytic activity of the 10-23 DNA enzyme under multiple-turnover conditions as described in Example 6. Initial velocities were measured over the first 10% of the reaction, employing a fixed concentration of enzyme (0.004 nM) and varying concentrations of substrate (0.02-4 nM). The 17mer RNA substrate, corresponding to the start codon region of HIV-1 gag/pol mRNA, was prepared by in vitro transcription. Reaction conditions: 2 mM MgCl2, 150 mM NaCl, pH 7.5, 37 C. Data from two independent experiments are shown and were fit to the Michaelis-Menten equation: v=kcat [E]/(Km+[S]).

Figure 12A:
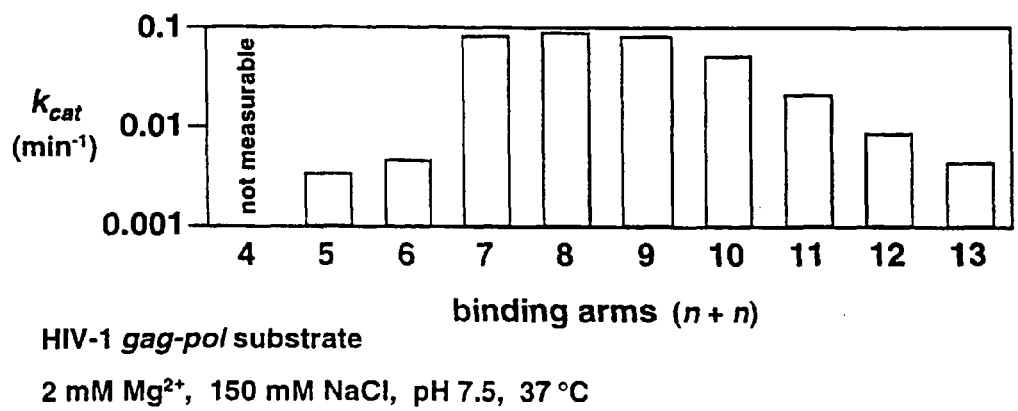
Figure 12B:
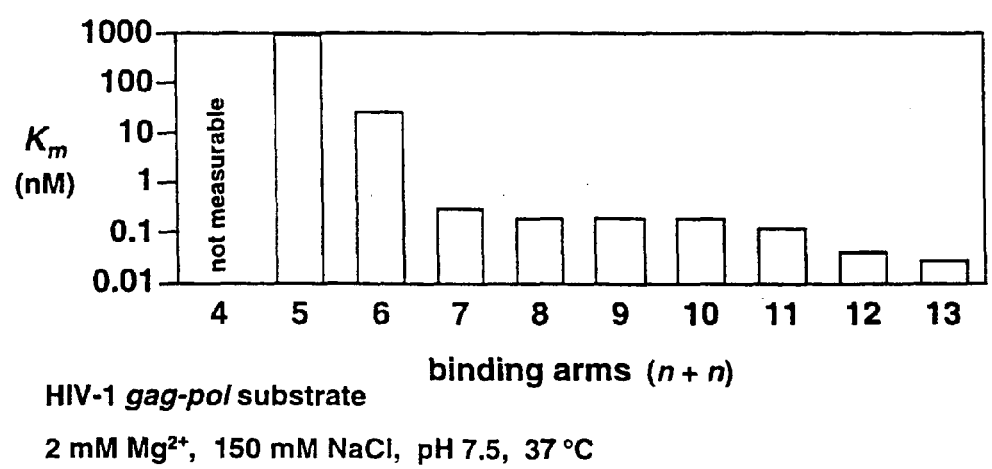

FIGS. 12A and 12B contain two panels that illustrate the effect of variation to the length of the substrate binding regions of a DNA enzyme of the invention, as described in Example 6. The length of the complementary substrate binding region was varied in length (n) from 4 to 13 nucleotides for each the first and second substrate binding region (arm), as noted, and the catalytic activity was measured and expressed as $k_{cat}$ (min$^{-1}$) and $K_m$ (nanomolar [nM]).

Figure 13:
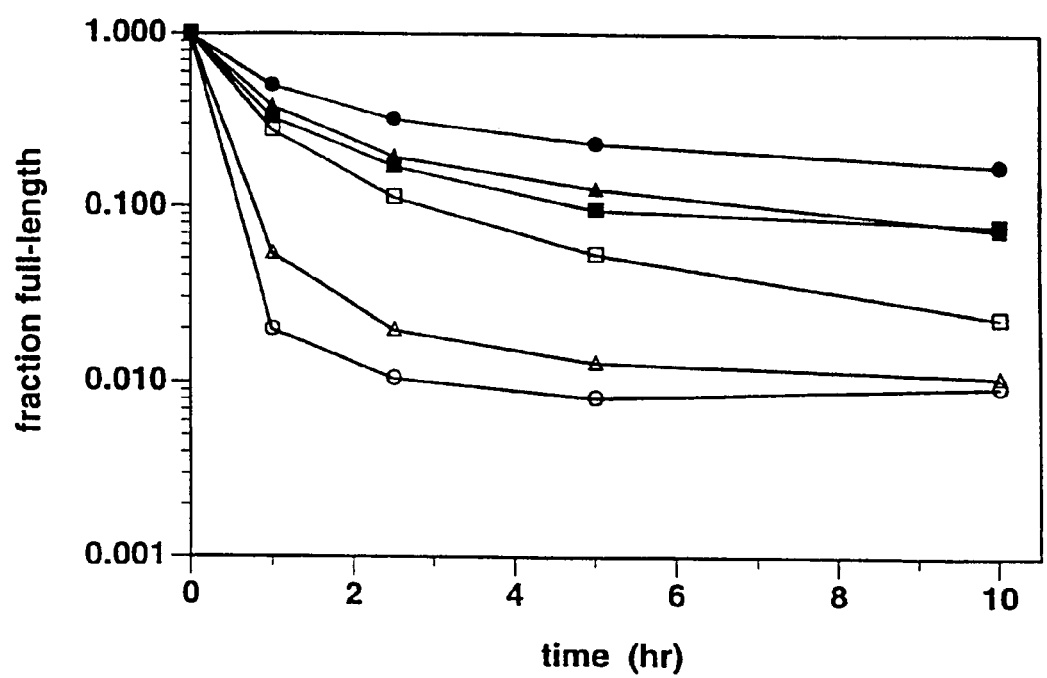

FIG. 13 illustrates the effect of modifications to the nucleotide residues of a DNA enzyme, as described in Example 6. DNA enzymes were incubated in 10% heat-inactivated fetal bovine serum in RPMI-1640 media at 37 °C, comparing unmodified DNA (open circles), inverted thymidylate (filled circles), five 2'-O—Me residues in each arm, (open squares), all 2-O—Me residues in each arm (filled squares), five P=S residues in core (open triangles), and three P=S residues in each arm (filled triangles).

DETAILED DESCRIPTION

A. Definitions

As used herein, the term "deoxyribozyme" is used to describe a DNA-containing nucleic acid that is capable of functioning as an enzyme. In the present disclosure, the term "deoxyribozyme" includes endoribonucleases and endodeoxyribonucleases, although deoxyribozymes with endoribonuclease activity are particularly preferred. Other terms used interchangeably with deoxyribozyme herein are "enzymatic DNA molecule", "DNAzyme", or "catalytic DNA molecule", which terms should all be understood to include enzymatically active portions thereof, whether they are produced synthetically or derived from organisms or other sources.

The term "enzymatic DNA molecules" also includes DNA molecules that have complementarity in a substrate-binding region to a specified oligonucleotide target or substrate; such molecules also have an enzymatic activity which is active to specifically cleave the oligonucleotide substrate. Stated in another fashion, the enzymatic DNA molecule is capable of cleaving the oligonucleotide substrate intermolecularly. This complementarity functions to allow sufficient hybridization of the enzymatic DNA molecule to the substrate oligonucleotide to allow the intermolecular cleavage of the substrate to occur. While one-hundred percent (100%) complementarity is preferred, complementarity in the range of 75-100% is also useful and contemplated by the present invention.

Enzymatic DNA molecules of the present invention may alternatively be described as having nuclease or ribonuclease activity. These terms may be used interchangeably herein.

The term "enzymatic nucleic acid" as used herein encompasses enzymatic RNA or DNA molecules, enzymatic RNA-DNA polymers, and enzymatically active portions or derivatives thereof, although enzymatic DNA molecules are a particularly preferred class of enzymatically active molecules according to the present invention.

The term "endodeoxyribonuclease", as used herein, is an enzyme capable of cleaving a substrate comprised predominantly of DNA. The term "endoribonuclease", as used herein, is an enzyme capable of cleaving a substrate comprised predominantly of RNA.

As used herein, the term "base pair" (bp) is generally used to describe a partnership of adenine (A) with thymine (T) or uracil (U), or of cytosine (C) with guanine (G), although it should be appreciated that less-common analogs of the bases A, T, C, and G (as well as U) may occasionally participate in base pairings. Nucleotides that normally pair up when DNA or RNA adopts a double stranded configuration may also be referred to herein as "complementary bases".

"Complementary nucleotide sequence" generally refers to a sequence of nucleotides in a single-stranded molecule or segment of DNA or RNA that is sufficiently complementary to that on another single oligonucleotide strand to specifically hybridize to it with consequent hydrogen bonding.

"Nucleotide" generally refers to a monomeric unit of DNA or RNA consisting of a sugar moiety (pentose), a phosphate group, and a nitrogenous heterocyclic base. The base is linked to the sugar moiety via the glycosidic carbon (1' carbon of the pentose) and that combination of base and sugar is a "nucleoside". When the nucleoside contains a phosphate group bonded to the 3' or 5' position of the pentose, it is referred to as a nucleotide. A sequence of operatively linked nucleotides is typically referred to herein as a "base sequence" or "nucleotide sequence", and their grammatical equivalents, and is represented herein by a formula whose left to right orientation is in the conventional direction of 5'-terminus to 3'-terminus, unless otherwise specified.

"Nucleotide analog" generally refers to a purine or pyrimidine nucleotide that differs structurally from A, T, G, C, or U, but is sufficiently similar to substitute for the normal nucleotide in a nucleic acid molecule. As used herein, the term "nucleotide analog" encompasses altered bases, different or unusual sugars (i.e. sugars other than the "usual" pentose), or a combination of the two. A listing of exemplary analogs wherein the base has been altered is provided in section C hereinbelow.

"Oligonucleotide or polynucleotide" generally refers to a polymer of single- or double-stranded nucleotides. As used herein, "oligonucleotide" and its grammatical equivalents will include the full range of nucleic acids. An oligonucleotide will typically refer to a nucleic acid molecule comprised of a linear strand of ribonucleotides. The exact size will depend on many factors, which in turn depends on the ultimate conditions of use, as is well known in the art.

As used herein, the term "physiologic conditions" is meant to suggest reaction conditions emulating those found in mammalian organisms, particularly humans. While variables such as temperature, availability of cations, and pH ranges may vary as described in greater detail below, "physiologic conditions" generally comprise a temperature of about 35-40° C., with 37° C. being particularly preferred, as well as a pH of about 7.0-8.0, with 7.5 being particularly preferred, and further comprise the availability of cations, preferably divalent and/or monovalent cations, with a concentration of about 2-15 mM Mg$^{2+}$ and 0-1.0 M Na+ being particularly preferred. "Physiologic conditions", as used herein, may optionally include the presence of free nucleoside cofactor. As noted previously, preferred conditions are described in greater detail below.

B. Enzymatic DNA Molecules

In various embodiments, an enzymatic DNA molecule of the present invention may combine one or more modifications or mutations including additions, deletions, and substitutions. In alternative embodiments, such mutations or modifications may be generated using methods which produce random or specific mutations or modifications. These mutations may, for example, change the length of, or alter the nucleotide sequence of, a loop, a spacer region or the recognition sequence (or domain). One or more mutations within one catalytically active enzymatic DNA molecule may be combined with the mutation(s) within a second catalytically active enzymatic DNA molecule to produce a new enzymatic DNA molecule containing the mutations of both molecules.

In other preferred embodiments, an enzymatic DNA molecule of the present invention may have random mutations introduced into it using a variety of methods well known to those skilled in the art. For example, the methods described by Cadwell et al, *PCR Methods and Applications,* 2:28-33, 1992, are particularly preferred for use as disclosed herein, with some modifications, as described in the Examples that follow. (Also see Cadwell et al, *PCR Methods and Applications,* 3(Suppl.):S136-S140, 1994.) According to this modified PCR method, random point mutations may be introduced into cloned genes.

The aforementioned methods have been used, for example, to mutagenize genes encoding ribozymes with a mutation rate of 0.66%±0.13% (95% confidence interval) per position, as determined by sequence analysis, with no strong preferences observed with respect to the type of base substitution. This allows the introduction of random mutations at any position in the enzymatic DNA molecules of the present invention.

Another method useful in introducing defined or random mutations is disclosed in Joyce et al, *Nucleic Acids Res.,* 17:711-722, 1989. This latter method involves excision of a template (coding) strand of a double-stranded DNA, reconstruction of the template strand with inclusion of mutagenic oligonucleotides, and subsequent transcription of the partially-mismatched template. This allows the introduction of defined or random mutations at any position in the molecule by including polynucleotides containing known or random nucleotide sequences at selected positions.

Enzymatic DNA molecules of the present invention may be of varying lengths and folding patterns, as appropriate, depending on the type and function of the molecule. For example, enzymatic DNA molecules may be about 15 to about 400 or more nucleotides in length, although a length not exceeding about 250 nucleotides is preferred, to avoid limiting the therapeutic usefulness of molecules by making them too large or unwieldy. In various preferred embodiments, an enzymatic DNA molecule of the present invention is at least about 20 nucleotides in length and, while useful molecules may exceed 100 nucleotides in length, preferred molecules are generally not more than about 100 nucleotides in length.

In various therapeutic applications, enzymatic DNA molecules of the present invention comprise the enzymatically active portions of deoxyribozymes. In various embodiments, enzymatic DNA molecules of the present invention preferably comprise not more than about 200 nucleotides. In other embodiments, a deoxyribozyme of the present invention comprises not more than about 100 nucleotides. In still other preferred embodiments, deoxyribozymes of the present invention are about 20-75 nucleotides in length, more preferably about 20-65 nucleotides in length. Other preferred enzymatic DNA molecules are about 10-50 nucleotides in length.

In other applications, enzymatic DNA molecules may assume configurations similar to those of "hammerhead" ribozymes. Such enzymatic DNA molecules are preferably no more than about 75-100 nucleotides in length, with a length of about 20-50 nucleotides being particularly preferred.

In general, if one intends to synthesize molecules for use as disclosed herein, the larger the enzymatic nucleic acid molecule is, the more difficult it is to synthesize. Those of skill in the art will certainly appreciate these design constraints. Nevertheless, such larger molecules remain within the scope of the present invention.

It is also to be understood that an enzymatic DNA molecule of the present invention may comprise enzymatically active portions of a deoxyribozyme or may comprise a deoxyribozyme with one or more mutations, e.g., with one or more base-pair-forming sequences or spacers absent or modified, as long as such deletions, additions or modifications do not adversely impact the molecule's ability to perform as an enzyme.

The recognition domain of an enzymatic DNA molecule of the present invention typically comprises two nucleotide sequences flanking a catalytic domain, and typically contains a sequence of at least about 3 to about 30 bases, preferably about 6 to about 15 bases, which are capable of hybridizing to a complementary sequence of bases within the substrate nucleic acid giving the enzymatic DNA molecule its high sequence specificity. Modification or mutation of the recognition site via well-known methods allows one to alter the sequence specificity of an enzymatic nucleic acid molecule. (See Joyce et al, *Nucleic Acids Res.,* 17:711-712, 1989.)

Enzymatic nucleic acid molecules of the present invention also include those with altered recognition sites or domains. In various embodiments, these altered recognition domains confer unique sequence specificities on the enzymatic nucleic acid molecule including such recognition domains. The exact bases present in the recognition domain determine the base sequence at which cleavage will take place. Cleavage of the substrate nucleic acid occurs within the recognition domain. This cleavage leaves a 2', 3', or 2',3'-cyclic-phosphate group on the substrate cleavage sequence and a 5' hydroxyl on the nucleotide that was originally immediately 3' of the substrate cleavage sequence in the original substrate. Cleavage can be redirected to a site of choice by changing the bases present in the recognition sequence (internal guide sequence). See Murphy et al, *Proc. Natl. Acad. Sci. USA,* 86:9218-9222, 1989.

Moreover, it may be useful to add a polyamine to facilitate recognition and binding between the enzymatic DNA molecule and its substrate. Examples of useful polyamines include spermidine, putrescine or spermine. A spermidine concentration of about 1 mM may be effective in particular embodiments, while concentrations ranging from about 0.1 mM to about 10 mM may also be useful.

In various alternative embodiments, an enzymatic DNA molecule of the present invention has an enhanced or optimized ability to cleave nucleic acid substrates, preferably RNA substrates. As those of skill in the art will appreciate, the rate of an enzyme-catalyzed reaction varies depending upon the substrate and enzyme concentrations and, in general, levels off at high substrate or enzyme concentrations. Taking such effects into account, the kinetics of an enzyme-catalyzed reaction may be described in the following terms, which define the reaction.

The enhanced or optimized ability of an enzymatic DNA molecule of the present invention to cleave an RNA substrate may be determined in a cleavage reaction with varying amounts of labeled RNA substrate in the presence of enzymatic DNA molecule. The ability to cleave the substrate is generally defined by the catalytic rate ($k_{cat}$) divided by the Michaelis constant ($K_M$). The symbol $k_{cat}$ represents the maximal velocity of an enzyme reaction when the substrate approaches a saturation value. $K_M$ represents the substrate concentration at which the reaction rate is one-half maximal.

For example, values for $K_M$ and $k_{cat}$ may be determined in this invention by experiments in which the substrate concentration [S] is in excess over enzymatic DNA molecule concentration [E]. Initial rates of reaction ($v_o$) over a range of substrate concentrations are estimated from the initial linear phase, generally the first 5% or less of the reaction. Data points are fit by a least squares method to a theoretical line given by the equation: $v=-K_M(v_o/[S])+V_{max}$. Thus, $k_{cat}$ and $K_M$ are determined by the initial rate of reaction, $v_o$, and the substrate concentration [S].

In various alternative embodiments, an enzymatic DNA molecule of the present invention has an enhanced or optimized ability to cleave nucleic acid substrates, preferably RNA substrates. In preferred embodiments, the enhanced or optimized ability of an enzymatic DNA molecule to cleave RNA substrates shows about a 10- to $10^9$-fold improvement over the uncatalyzed rate. In more preferred embodiments, an enzymatic DNA molecule of the present invention is able to cleave RNA substrates at a rate that is about $10^3$- to $10^7$-fold improved over "progenitor" species. In even more preferred embodiments, the enhanced or optimized ability to cleave RNA substrates is expressed as a $10^4$- to $10^6$-fold improvement over the progenitor species. One skilled in the art will appreciate that the enhanced or optimized ability of an enzymatic DNA molecule to cleave nucleic acid substrates may vary depending upon the selection constraints applied during the in vitro evolution procedure of the invention.

Various preferred methods of modifying deoxyribozymes and other enzymatic DNA molecules and nucleases of the present invention are further described in Examples 1-3 hereinbelow.

C. Nucleotide Analogs

As noted above, the term "nucleotide analog" as used herein generally refers to a purine or pyrimidine nucleotide that differs structurally from A, T, G, C, or U, but is sufficiently similar to substitute for such "normal" nucleotides in a nucleic acid molecule. As used herein, the term "nucleotide analog" encompasses altered bases, different (or unusual) sugars, altered phosphate backbones, or any combination of these alterations. Examples of nucleotide analogs useful according to the present invention include those listed in the following Table, most of which are found in the approved listing of modified bases at 37 CFR §1.822 (which is incorporated herein by reference).

TABLE 1

Nucleotide Analogs

| Abbreviation | Description |
|---|---|
| ac4c | 4-acetylcytidine |
| chm5u | 5-(carboxyhydroxylmethyl)uridine |
| cm | 2'-O-methylcytidine |
| cmnm5s2u | 5-carboxymethylaminomethyl-2-thiouridine |
| d | dihydrouridine |
| fm | 2'-O-methylpseudouridine |
| galq | β,D-galactosylqueosine |
| gm | 2'-O-methylguanosine |
| I | inosine |
| i6a | N6-isopentenyladenosine |
| m1a | 1-methyladenosine |
| m1f | 1-methylpseudouridine |
| m1g | 1-methylguanosine |
| m1I | 1-methylinosine |
| m22g | 2,2-dimethylguanosine |
| m2a | 2-methyladenosine |
| m2g | 2-methylguanosine |
| m3c | 3-methylcytidine |
| m5c | 5-methylcytidine |
| m6a | N6-methyladenosine |
| m7g | 7-methylguanosine |
| mam5u | 5-methylaminomethyluridine |
| mam5s2u | 5-methoxyaminomethyl-2-thiouridine |
| manq | β,D-mannosylmethyluridine |
| mcm5s2u | 5-methoxycarbonylmethyluridine |
| mo5u | 5-methoxyuridine |
| ms2i6a | 2-methylthio-N6-isopentenyladenosine |

TABLE 1-continued

Nucleotide Analogs

| Abbreviation | Description |
|---|---|
| ms2t6a | N-((9-β-D-ribofuranosyl-2-methylthiopurine-6-yl)carbamoyl)threonine |
| mt6a | N-((9-β-D-ribofuranosylpurine-6-yl)N-methyl-carbamoyl)threonine |
| mv | uridine-5-oxyacetic acid methylester |
| o5u | uridine-5-oxyacetic acid (v) |
| osyw | wybutoxosine |
| p | pseudouridine |
| q | queosine |
| s2c | 2-thiocytidine |
| s2t | 5-methyl-2-thiouridine |
| s2u | 2-thiouridine |
| s4u | 4-thiouridine |
| t | 5-methyluridine |
| t6a | N-((9-β-D-ribofuranosylpurine-6-yl)carbamoyl)threonine |
| tm | 2'-O-methyl-5-methyluridine |
| um | 2'-O-methyluridine |
| yw | wybutosine |
| x | 3-(3-amino-3-carboxypropyl)uridine, (acp3)u |
| araU | β,D-arabinosyl |
| araT | β,D-arabinosyl |

Other useful analogs include those described in published international application no. WO 92/20823 (the disclosures of which are incorporated herein by reference), or analogs made according to the methods disclosed therein. Analogs described in DeMesmaeker et al, *Angew. Chem. Int. Ed. Engl.*, 33:226-229, 1994; DeMesmaeker et al, *Synlett* 733-736 (Oct. 1993); Nielsen et al, *Science*, 254:1497-1500, 1991; and Idziak et al, *Tetrahedron Letters*, 34:5417-5420, 1993, are also useful according to the within-disclosed invention and said disclosures are incorporated by reference herein.

D. Methods of Engineering Enzymatic DNA Molecules

The present invention also contemplates methods of producing nucleic acid molecules having a predetermined activity. In one preferred embodiment, the nucleic acid molecule is an enzymatic DNA molecule. In another variation, the desired activity is a catalytic activity.

In one embodiment, the present invention contemplates methods of synthesizing enzymatic DNA molecules that may then be "engineered" to catalyze a specific or predetermined reaction. Methods of preparing enzymatic DNA molecules are described herein; see, e.g., Examples 1-3 hereinbelow. In other embodiments, an enzymatic DNA molecule of the present invention may be engineered to bind small molecules or ligands, such as adenosine triphosphate (ATP). (See Sassanfar et al, *Nature*, 364:550-553, 1993.)

In another embodiment, the present invention contemplates that a population of enzymatic DNA molecules may be subjected to mutagenizing conditions to produce a diverse population of mutant enzymatic DNA molecules (which may alternatively be called "deoxyribozymes" or "DNAzymes"). Thereafter, enzymatic DNA molecules having desired characteristics are selected and/or separated from the population and are subsequently amplified.

Alternatively, mutations may be introduced in the enzymatic DNA molecule by altering the length of the recognition domains of the enzymatic DNA molecule. The recognition domains of the enzymatic DNA molecule associate with a complementary sequence of bases within a substrate nucleic acid sequence. Methods of altering the length of the recognition domains are known in the art and include PCR, for example; useful techniques are described further in the Examples below.

Alteration of the length of the recognition domains of an enzymatic DNA molecule may have a desirable effect on the binding specificity of the enzymatic DNA molecule. For example, an increase in the length of the recognition domains may increase binding specificity between the enzymatic DNA molecule and the complementary base sequences of an oligonucleotide in a substrate, or may enhance recognition of a particular sequence in a hybrid substrate. In addition, an increase in the length of the recognition domains may also increase the affinity with which it binds to substrate. In various embodiments, these altered recognition domains in the enzymatic DNA molecule confer increased binding specificity and affinity between the enzymatic DNA molecule and its substrate.

It has recently been noted that certain oligonucleotides are able to recognize and bind molecules other than oligonucleotides with complementary sequences. These oligonucleotides are often given the name "aptamers". For example, Ellington et al describe RNA molecules that are able to bind a variety of organic dyes (*Nature*, 346:818-822, 1990), while Bock et al describe ssDNA molecules that bind human thrombin (*Nature*, 355:564-566, 1992). Similarly, Jellinek et al describe RNA ligands to basic fibroblast growth factor (*Proc. Natl. Acad. Sci. USA*, 90:11227-11231, 1993). Thus, it is further contemplated herein that the catalytically active DNA enzymes of the present invention may be engineered according to the within-described methods to display a variety of capabilities typically associated with aptamers.

One of skill in the art should thus appreciate that the enzymatic DNA molecules of this invention can be altered at any nucleotide sequence, such as the recognition domains, by various methods disclosed herein, including PCR and 3SR (self-sustained sequence replication—see Example 1 below). For example, additional nucleotides can be added to the 5' end of the enzymatic DNA molecule by including additional nucleotides in the primers.

Enzymatic DNA molecules of the present invention may also be prepared or engineered in a more non-random fashion via use of methods such as site-directed mutagenesis. For example, site-directed mutagenesis may be carried out essentially as described in Morinaga et al, *Biotechnology*, 2:636, 1984, modified as described herein, for application to deoxyribozymes. Useful methods of engineering enzymatic DNA molecules are further described in the Examples below.

In one disclosed embodiment, an enzymatic DNA molecule of the present invention comprises a conserved core flanked by two substrate binding (or recognition) domains or sequences that interact with the substrate through base-pairing interactions. In various embodiments, the conserved core comprises one or more conserved domains or sequences. In another variation, an enzymatic DNA molecule further comprises a "spacer" region (or sequence) between the regions (or sequences) involved in base pairing. In still another variation, the conserved core is "interrupted" at various intervals by one or more less-conserved variable or "spacer" nucleotides.

In various embodiments, the population of enzymatic DNA molecules is made up of at least 2 different types of deoxyribozyme molecules. For example, in one variation, the molecules have differing sequences. In another variation, the deoxyribozymes are nucleic acid molecules having a nucleic acid sequence defining a recognition domain that is contiguous or adjacent to the 5'-terminus of the nucleotide sequence. In various alternative embodiments, enzymatic DNA molecules of the present invention may further comprise one or more spacer regions located 3'-terminal to the recognition domains, one or more loops located 3'-terminal to the recognition domains and/or spacer regions. In other variations, a deoxyribozyme of the present invention may comprise one or more regions which are capable of hybridizing to other regions of the same molecule. Other characteristics of enzymatic DNA molecules produced according to the presently-disclosed methods are described elsewhere herein.

In other embodiments, mutagenizing conditions include conditions that introduce either defined or random nucleotide substitutions within an enzymatic DNA molecule. Examples of typical mutagenizing conditions include conditions disclosed in other parts of this specification and the methods described by Joyce et al, *Nucl. Acids Res.*, 17:711-722, 1989; Joyce, *Gene*, 82:83-87, 1989; and Beaudry et al, *Science*, 257:635-41, 1992.

In still other embodiments, a diverse population of mutant enzymatic nucleic acid molecules of the present invention is one that contains at least 2 nucleic acid molecules that do not have the exact same nucleotide sequence. In other variations, from such a diverse population, an enzymatic DNA molecule or other enzymatic nucleic acid having a predetermined activity is then selected on the basis of its ability to perform the predetermined activity. In various embodiments, the predetermined activity comprises, without limitation, enhanced catalytic activity, decreased $K_M$, enhanced substrate binding ability, altered substrate specificity, and the like.

Other parameters which may be considered aspects of enzyme performance include catalytic activity or capacity, substrate binding ability, enzyme turnover rate, enzyme sensitivity to feedback mechanisms, and the like. In certain aspects, substrate specificity may be considered an aspect of enzyme performance, particularly in situations in which an enzyme is able to recognize and bind two or more competing substrates, each of which affects the enzyme's performance with respect to the other substrate(s).

Substrate specificity, as used herein, may refer to the specificity of an enzymatic nucleic acid molecule as described herein for a particular substrate, such as one comprising ribonucleotides only, deoxyribonucleotides only, or a composite of both. Substrate molecules may also contain nucleotide analogs. In various embodiments, an enzymatic nucleic acid molecule of the present invention may preferentially bind to a particular region of a hybrid or non-hybrid substrate.

The term or parameter identified herein as "substrate specificity" may also include sequence specificity; i.e., an enzymatic nucleic acid molecule of the present invention may "recognize" and bind to a nucleic acid substrate having a particular nucleic acid sequence. For example, if the substrate recognition domains of an enzymatic nucleic acid molecule of the present invention will only bind to substrate molecules having a series of one or two ribonucleotides (e.g., rA) in a row, then the enzymatic nucleic acid molecule will tend not to recognize or bind nucleic acid substrate molecules lacking such a sequence.

With regard to the selection process, in various embodiments, selecting includes any means of physically separating the mutant enzymatic nucleic acids having a predetermined activity from the diverse population of mutant enzymatic nucleic acids. Often, selecting comprises separation by size, by the presence of a catalytic activity, or by hybridizing the mutant nucleic acid to another nucleic acid, to a peptide, or some other molecule that is either in solution or attached to a solid matrix.

In various embodiments, the predetermined activity is such that the mutant enzymatic nucleic acid having the predetermined activity becomes labeled in some fashion by virtue of the activity. For example, the predetermined activity may be an enzymatic DNA molecule activity whereby the activity of the mutant enzymatic nucleic acid upon its substrate causes the mutant enzymatic nucleic acid to become covalently linked to it. The mutant enzymatic nucleic acid is then selected by virtue of the covalent linkage.

In other embodiments, selecting a mutant enzymatic nucleic acid having a predetermined activity includes amplification of the mutant enzymatic nucleic acid (see Joyce, *Gene,* 82:83-87, 1989; Beaudry et al, *Science,* 257:635-41, 1992). Other methods of selecting an enzymatic nucleic acid molecule having a predetermined characteristic or activity are described in the Examples section.

E. Compositions

The invention also contemplates compositions containing one or more types or populations of enzymatic DNA molecules of the present invention; e.g., different types or populations may recognize and cleave different nucleotide sequences. Compositions may further include a ribonucleic acid-containing substrate. Compositions according to the present invention may further comprise lead ion, magnesium ion, or other divalent or monovalent cations, as discussed herein.

Preferably, the enzymatic DNA molecule is present at a concentration of about 0.05 μM to about 2 μM. Typically, the enzymatic DNA molecule is present at a concentration ratio of enzymatic DNA molecule to substrate of from about 1:5 to about 1:50. More preferably, the enzymatic DNA molecule is present in the composition at a concentration of about 0.1 μM to about 1 μM. Even more preferably, compositions contain the enzymatic DNA molecule at a concentration of about 0.1 μM to about 0.5 μM. Preferably, the substrate is present in the composition at a concentration of about 0.5 μM to about 1000 μM.

One skilled in the art will understand that there are many sources of nucleic acid-containing substrates including naturally-occurring and synthetic sources. Sources of suitable substrates include, without limitation, a variety of viral and retroviral agents, including HIV-1, HIV-2, HTLV-I, and HTLV-II.

Other suitable substrates include, without limitation, viral and retroviral agents including those comprising or produced by picornaviruses, hepadnaviridae (e.g., HBV, HCV), papillomaviruses (e.g., HPV), gammaherpesvirinae (e.g., EBV), lymphocryptoviruses, leukemia viruses (e.g., HTLV-I and -II), flaviviruses, togaviruses, herpesviruses (including alphaherpesviruses and betaherpesviruses), cytomegaloviruses (CMV), influenza viruses, and viruses and retroviruses contributing to immunodeficiency diseases and syndromes (e.g., HIV-1 and -2). In addition, suitable substrates include viral and retroviral agents which infect non-human primates and other animals including, without limitation, the simian and feline immunodeficiency viruses and bovine leukemia viruses.

Magnesium ion, lead ion, or another suitable monovalent or divalent cation, as described previously, may also be present in the composition, at a concentration ranging from about 1-100 mM. More preferably, the preselected ion is present in the composition at a concentration of about 2 mM to about 50 mM, with a concentration of about 5 mM being particularly preferred. One skilled in the art will understand that the ion concentration is only constrained by the limits of solubility of its source (e.g. magnesium) in aqueous solution and a desire to have the enzymatic DNA molecule present in the same composition in an active conformation.

The invention also contemplates compositions containing an enzymatic DNA molecule of the present invention, hybrid deoxyribonucleotide-ribonucleotide molecules, and magnesium or lead ion in concentrations as described hereinabove.

As noted previously, other monovalent or divalent ions (e.g., $Ca^{2+}$) may be used in place of magnesium.

Also contemplated by the present invention are compositions containing an enzymatic DNA molecule of the present invention, nucleic acid-containing substrate (e.g. RNA), and a preselected ion at a concentration of greater than about 1 millimolar, wherein said substrate is greater in length than the recognition domains present on the enzymatic DNA molecule.

In one variation, a composition comprises an enzymatic DNA molecule-substrate complex, wherein base pairing between an enzymatic DNA molecule and its substrate is contiguous. In another embodiment, base pairing between an enzymatic DNA molecule and its substrate is interrupted by one or more noncomplementary pairs. In a variety of alternative embodiments, a composition of the present invention may further comprise a monovalent cation, a divalent cation, or both.

In another variation, an enzymatic DNA molecule of the present invention is capable of functioning efficiently in the presence or absence of a divalent cation. In one variation, a divalent cation is present and comprises $Pb^{2+}$, $Mg^{2+}$, $Mn^{2+}$, $Zn^{2+}$, or $Ca^{2+}$. Alternatively, an enzymatic DNA molecule of the present invention is capable of functioning efficiently in the presence or absence of monovalent cations. It is anticipated that monovalent or divalent cation concentrations similar to those described herein for $Pb^{2+}$ or $Mg^{2+}$ will be useful as disclosed herein.

Optionally, monovalent cations may also be present in addition to, or as "alternatives" for, divalent cations. For example, monovalent cations such as sodium ($Na^+$) or potassium ($K^+$) may be present, either as dissociated ions or in the form of dissociable compounds such as NaCl or KCl.

In one embodiment, the concentration of monovalent cation present in the composition ranges from 0-1.0 M. In another embodiment, a monovalent cation is present in a concentration ranging from about 0-200 mM. In other embodiments, monovalent cations are present in a concentration ranging from about 1-100 mM. Alternatively, the concentration of monovalent cations ranges from about 2 mM-50 mM. In still other embodiments, the concentration ranges from about 2 mM-25 mM.

F. Methods of Using Enzymatic DNA Molecules

Methods for using enzymatic DNA molecules as disclosed herein cover many different utilities as are well known in the art for prior art enzymatic and/or antisense oligonucleotides. As discussed previously, molecules capable of cleaving the bonds linking neighboring nucleic acids (e.g., phosphoester bonds) have numerous uses encompassing a wide variety of applications. For example, enzymatic DNA molecules having the within-disclosed capabilities, structures, and/or functions are useful in pharmaceutical and medical products (e.g., for wound debridement, clot dissolution, etc.), as well as in household items (e.g., detergents, dental hygiene products, meat tenderizers). For inactivating target nucleic acid sequences, such as mRNA in vitro and in vivo. Industrial utility of the within-disclosed compounds, compositions and methods is also contemplated and well within the scope of the present invention.

The present invention also describes useful methods for cleaving any single-stranded, looped, partially or fully double-stranded nucleic acid; the majority of these methods employ the novel enzymatically active nucleic acid molecules of the present invention. In various embodiments, the single-stranded nucleic acid segment or portion of the substrate (or the entire substrate itself) comprises DNA, modified DNA, RNA, modified RNA, or composites thereof. Preferably, the nucleic acid substrate need only be single-stranded at or near the substrate cleavage sequence so that an enzymatic nucleic acid molecule of the present invention can hybridize to the substrate cleavage sequence by virtue of the enzyme's recognition sequence.

A nucleic acid substrate that can be cleaved by a method of this invention may be chemically synthesized or enzymatically produced, or it may be isolated from various sources such as phages, viruses, prokaryotic cells, or eukaryotic cells, including animal cells, plant cells, yeast cells and bacterial cells. Chemically synthesized single- and double-stranded nucleic acids are commercially available from many sources including, without limitation, Research Genetics (Huntsville, Ala.).

RNA substrates may also be synthesized using an Applied Biosystems (Foster City, Calif.) oligonucleotide synthesizer according to the manufacturer's instructions. Single-stranded phage are also a source of nucleic acid substrates. (See Messing et al, *Proc. Natl. Acad. Sci. USA,* 74:3642-3646, 1977, and Yanisch-Perron et al, *Gene,* 33:103-119, 1985). Bacterial cells containing single-stranded phage would also be a ready source of suitable single-stranded nucleic acid substrates.

Single-stranded RNA cleavable by a method of the present invention could be provided by any of the RNA viruses such as the picornaviruses, togaviruses, orthomyxoviruses, paramyxoviruses, rhabdoviruses, coronaviruses, arenaviruses or retroviruses. As noted previously, a wide variety of prokaryotic and eukaryotic cells may also be excellent sources of suitable nucleic acid substrates.

The methods of this invention may be used on single-stranded nucleic acids or single-stranded portions of looped or double-stranded nucleic acids that are present inside a cell, including eukaryotic, procaryotic, plant, animal, yeast or bacterial cells. Under these conditions an enzymatic nucleic acid molecule (e.g., an enzymatic DNA molecule or deoxyribozyme) of the present invention could act as an anti-viral agent or a regulator of gene expression. Examples of such uses of enzymatic DNA molecules of the present invention are described further hereinbelow.

In the majority of methods of the present invention, cleavage of single-stranded nucleic acids occurs at the 3'-terminus of a predetermined base sequence. This predetermined base sequence or substrate cleavage sequence typically contains from 1 to about 10 nucleotides. In other preferred embodiments, an enzymatic DNA molecule of the present invention is able to recognize nucleotides either upstream, or upstream and downstream of the cleavage site. In various embodiments, an enzymatic DNA molecule is able to recognize about 2-10 nucleotides upstream of the cleavage site; in other embodiments, an enzymatic DNA molecule is able to recognize about 2-10 nucleotides upstream and about 2-10 nucleotides downstream of the cleavage site. Other preferred embodiments contemplate an enzymatic DNA molecule that is capable of recognizing a nucleotide sequence up to about 30 nucleotides in length, with a length up to about 20 nucleotides being even more preferred.

The within-disclosed methods allow cleavage at any nucleotide sequence by altering the nucleotide sequence of the recognition domains of the enzymatic DNA molecule. This allows cleavage of single-stranded nucleic acid in the absence of a restriction endonuclease site at the selected position.

An enzymatic DNA molecule of the present invention may be separated from any portion of the single-stranded nucleic acid substrate that remains attached to the enzymatic DNA molecule by site-specific hydrolysis at the appropriate cleavage site. Separation of the enzymatic DNA molecule from the substrate (or "cleavage product") allows the enzymatic DNA molecule to carry out another cleavage reaction.

Generally, the nucleic acid substrate is treated under appropriate nucleic acid cleaving conditions—preferably, physiologic conditions—with an effective amount of an enzymatic DNA molecule of the present invention. If the nucleic acid substrate comprises DNA, cleaving conditions may include the presence of a divalent cation at a concentration of about 2-10 mM.

An effective amount of an enzymatic DNA molecule is the amount required to cleave a predetermined base sequence present within the single-stranded nucleic acid. Preferably, the enzymatic DNA molecule is present at a molar ratio of DNA molecule to substrate cleavage sites of 1 to 20. This ratio may vary depending on the length of treating and efficiency of the particular enzymatic DNA molecule under the particular nucleic acid cleavage conditions employed.

Thus, in one preferred embodiment, treating typically involves admixing, in aqueous solution, the RNA-containing substrate and the enzyme to form a cleavage admixture, and then maintaining the admixture thus formed under RNA cleaving conditions for a time period sufficient for the enzymatic DNA molecule to cleave the RNA substrate at any of the predetermined nucleotide sequences present in the RNA. In various embodiments, a source of ions is also provided—i.e. monovalent or divalent cations, or both.

In one embodiment of the present invention, the amount of time necessary for the enzymatic DNA molecule to cleave the single-stranded nucleic acid has been predetermined. The amount of time is from about 1 minute to about 24 hours and will vary depending upon the concentration of the reactants and the temperature of the reaction. Usually, this time period is from about 10 minutes to about 2 hours such that the enzymatic DNA molecule cleaves the single-stranded nucleic acid at any of the predetermined nucleotide sequences present.

The invention further contemplates that the nucleic acid cleaving conditions include the presence of a source of divalent cations (e.g., PbOAc) at a concentration of about 2-100 mM. Typically, the nucleic acid cleaving conditions include divalent cation at a concentration of about 2 mM to about 10 mM, with a concentration of about 5 mM being particularly preferred.

The optimal cationic concentration to include in the nucleic acid cleaving conditions can be easily determined by determining the amount of single-stranded nucleic acid cleaved at a given cation concentration. One skilled in the art will understand that the optimal concentration may vary depending on the particular enzymatic DNA molecule employed.

The present invention further contemplates that the nucleic acid cleaving conditions include a pH of about pH 6.0 to about pH 9.0. In one preferred embodiment, the pH ranges from about pH 6.5 to pH 8.0. In another preferred embodiment, the pH emulates physiological conditions, i.e., the pH is about 7.0-7.8, with a pH of about 7.5 being particularly preferred.

One skilled in the art will appreciate that the methods of the present invention will work over a wide pH range so long as the pH used for nucleic acid cleaving is such that the enzymatic DNA molecule is able to remain in an active conformation. An enzymatic DNA molecule in an active conformation is easily detected by its ability to cleave single-stranded nucleic acid at a predetermined nucleotide sequence.

In various embodiments, the nucleic acid cleaving conditions also include a variety of temperature ranges. As noted previously, temperature ranges consistent with physiological conditions are especially preferred, although temperature ranges consistent with industrial applications are also contemplated herein. In one embodiment, the temperature ranges from about 15° C. to about 60° C. In another variation, the nucleic acid cleaving conditions include a temperature ranging from about 30° C. to about 56° C. In yet another variation, nucleic acid cleavage conditions include a temperature from about 35° C. to about 50° C. In a preferred embodiment, nucleic acid cleavage conditions comprise a temperature range of about 37° C. to about 42° C. The temperature ranges consistent with nucleic acid cleaving conditions are constrained only by the desired cleavage rate and the stability of that particular enzymatic DNA molecule at that particular temperature.

In various methods, the present invention contemplates nucleic acid cleaving conditions including the presence of a polyamine. Polyamines useful for practicing the present invention include spermidine, putrescine, spermine and the like. In one variation, the polyamine is present at a concentration of about 0.01 mM to about 10 mM. In another variation, the polyamine is present at a concentration of about 1 mM to about 10 mM. Nucleic acid cleavage conditions may also include the presence of polyamine at a concentration of about 2 mM to about 5 mM. In various preferred embodiments, the polyamine is spermidine.

G. Vectors

The present invention also features expression vectors including a nucleic acid segment encoding an enzymatic DNA molecule of the present invention situated within the vector, preferably in a manner which allows expression of that enzymatic DNA molecule within a target cell (e.g., a plant or animal cell).

Thus, in general, a vector according to the present invention preferably includes a plasmid, cosmid, phagemid, virus, or phage vector. Preferably, suitable vectors comprise single-stranded DNA (ssDNA)—e.g., circular phagemid ssDNA. It should also be appreciated that useful vectors according to the present invention need not be circular.

In one variation, nucleotide sequences flanking each of the additional enzymatic DNA molecule-encoding sequences are preferably provided, which sequences may be recognized by the first enzymatic DNA molecule. The intervening or flanking sequences preferably comprise at least 1 nucleotide; more preferably, intervening or flanking sequences are about 2-20 nucleotides in length, with sequences of about 5-10 nucleotides in length being particularly preferred.

The addition of polynucleotide tails may also be useful to protect the 3' end of an enzymatic DNA molecule according to the present invention. These may be provided by attaching a polymeric sequence by employing the enzyme terminal transferase.

A vector according to the present invention includes two or more enzymatic DNA molecules. In one embodiment, a first enzymatic DNA molecule has intramolecular cleaving activity and is able to recognize and cleave nucleotide sequences to release other enzymatic DNA sequences; i.e., it is able to function to "release" other enzymatic DNA molecules from the vector. For example, a vector is preferably constructed so that when the first enzymatic DNA molecule is expressed, that first molecule is able to cleave nucleotide sequences flanking additional nucleotide sequences encoding a second enzymatic DNA molecule, a third enzymatic DNA molecule, and so forth. Presuming said first enzymatic DNA molecule (i.e., the "releasing" molecule) is able to cleave oligonucleotide sequences intramolecularly, the additional (e.g. second, third, and so on) enzymatic DNA molecules (i.e., the "released" molecules) need not possess characteristics identical to the "releasing" molecule. For example, in one embodiment, the "released" (i.e., the second, third, etc.) enzymatic DNA molecules are able to cleave specific RNA sequences, while the first ("releasing") enzymatic DNA molecule has nuclease activity allowing it to liberate the "released" molecules. In another embodiment, the "released" enzymatic DNA molecule has amide bond-cleaving activity, while the first ("releasing") enzymatic DNA molecule has nuclease activity.

Alternatively, the first enzymatic DNA molecule may be encoded on a separate vector from the second (and third, fourth, etc.) enzymatic DNA molecules) and may have intermolecular cleaving activity. As noted herein, the first enzymatic DNA molecule can be a self-cleaving enzymatic DNA molecule (e.g., a deoxyribozyme), and the second enzymatic DNA molecule may be any desired type of enzymatic DNA molecule. When a vector is caused to express DNA from these nucleic acid sequences, that DNA has the ability under appropriate conditions to cleave each of the flanking regions, thereby releasing one or more copies of the second enzymatic DNA molecule. If desired, several different second enzymatic DNA molecules can be placed in the same cell or carrier to produce different deoxyribozymes. It is also contemplated that any one or more vectors may comprise one or more ribozymes or deoxyribozymes in any combination of "releasing" and "released" enzymatic nucleic acid molecules, as long as such a combination achieves the desired result: the release of enzymatic nucleic acid molecules that are capable of cleaving predetermined nucleic acid sequences.

Methods of isolating and purifying enzymatic DNA molecules of the present invention are also contemplated. In addition to the methods described herein, various purification methods (e.g. those using HPLC) and chromatographic isolation techniques are available in the art. See, e.g., the methods described in published international application no. WO 93/23569, the disclosures of which are incorporated herein by reference.

It should also be understood that various combinations of the embodiments described herein are included within the scope of the present invention. Other features and advantages of the present invention will be apparent from the descriptions hereinabove, from the Examples to follow, and from the claims.

EXAMPLES

The following examples illustrate, but do not limit, the present invention.

1. In Vitro Evolution of Enzymatic DNA Molecules: An Overview

In vitro selection and in vitro evolution techniques allow new catalysts to be isolated without a priori knowledge of their composition or structure. Such methods have been used to obtain RNA enzymes with novel catalytic properties. For example, ribozymes that undergo autolytic cleavage with lead cation have been derived from a randomized pool of tRNA$^{Phe}$ molecules (Pan et al, *Biochemistry*, 31:3887-3895, 1992). Group I ribozyme variants have been isolated that can cleave DNA (Beaudry et al, *Science*, 257:635-641, 1992) or that have altered metal dependence (Lehman et al, *Nature*, 361: 182-185, 1993). Starting with a pool of random RNA sequences, molecules have been obtained that catalyze a polymerase-like reaction (Bartel et al, *Science*, 261:1411-1418, 1993). In the present example, refinement of specific catalytic properties of an evolved enzyme via alteration of the selection constraints during an in vitro evolution procedure is described.

Darwinian evolution requires the repeated operation of three processes: (a) introduction of genetic variation; (b) selection of individuals on the basis of some fitness criterion; and (c) amplification of the selected individuals. Each of these processes can be realized in vitro (Joyce, *Gene*, 82:83, 1989). A gene can be mutagenized by chemical modification, incorporation of randomized mutagenic oligodeoxynucleotides, or inaccurate copying by a polymerase. (See Cadwell et al, *PCR Methods and Applications*, 2:28-33, 1992); Cadwell et al, *PCR Methods and Applications*, 3(Suppl.):S136-S140, 1994; Chu et al, *Virology*, 98:168, 1979; Shortle et al, *Meth. Enzymol.*, 100:457, 1983; Myers et al, *Science*, 229:242, 1985; Matteucci et al, *Nucleic Acids Res.*, 11:3113, 1983; Wells et al, *Gene*, 34:315, 1985; McNeil et al, *Mol. Cell. Biol.*, 5:3545, 1985; Hutchison et al, *Proc. Natl. Acad. Sci. USA*, 83:710, 1986; Derbyshire et al, *Gene*, 46:145, 1986; Zakour et al, *Nature*, 295:708, 1982; Lehtovaara et al, *Protein Eng.*, 2:63, 1988; Leung et al, *Technique*, 1:11, 1989; Zhou et al, *Nucl. Acids Res.*, 19:6052, 1991).

The gene product can be selected, for example, by its ability to bind a ligand or to carry out a chemical reaction. (See, e.g., Joyce, *Id.*, 1989; Robertson et al, *Nature*, 344:467, 1990; Tuerk et al, *Science*, 249:505, 1990). The gene that corresponds to the selected gene product can be amplified by a reciprocal primer method, such as the polymerase chain reaction (PCR). (See Saiki et al, *Science*, 230:1350-54, 1985; Saiki et al, *Science*, 239:487-491, 1988).

Alternatively, nucleic acid amplification may be carried out using self-sustained sequence replication (3SR). (See Guatelli et al, *Proc. Natl. Acad. Sci USA*, 87:1874, 1990, the disclosures of which are incorporated by reference herein.) According to the 3SR method, target nucleic acid sequences may be amplified (replicated) exponentially in vitro under isothermal conditions by using three enzymatic activities essential to retroviral replication: (1) reverse transcriptase, (2) RNase H, and (3) a DNA-dependent RNA polymerase. By mimicking the retroviral strategy of RNA replication by means of cDNA intermediates, this reaction accumulates cDNA and RNA copies of the original target.

In summary, if one is contemplating the evolution of a population of enzymatic DNA molecules, a continuous series of reverse transcription and transcription reactions replicates an RNA target sequence by means of cDNA intermediates. The crucial elements of this design are (a) the oligonucleotide primers both specify the target and contain 5' extensions encoding the T7 RNA polymerase binding site, so that the resultant cDNAs are competent transcription templates; (b) cDNA synthesis can proceed to completion of both strands due to the degradation of template RNA in the intermediate RNA-DNA hybrid by RNase H; and (c) the reaction products (cDNA and RNA) can function as templates for subsequent steps, enabling exponential replication.

If one is evolving enzymatic DNA molecules, various critical elements of this design are somewhat different, as disclosed in these Examples. For instance, (1) the oligonucleotide primers specify the target and are preferably "marked" or labeled in some fashion—e.g., via biotinylation—so the resultant competent template strands are easily identified; and (2) the in vitro selection procedure used preferably depends upon the identification of the most favorable release mechanism.

A major obstacle to realizing Darwinian evolution in vitro is the need to integrate mutation and amplification, both of which are genotype-related, with selection, which is phenotype-related. In the case of nucleic acid enzymes, for which genotype and phenotype are embodied in the same molecule, the task is simplified.

A. Design of Enzymatic DNA Molecules

It is well known that single-stranded DNA can assume interesting tertiary structures. The structure of a "tDNA", for example, closely resembles that of the corresponding tRNA. (See Paquette et al, *Eur. J. Biochem.*, 189:259-265, 1990). Furthermore, it has been possible to replace as many as 31 of 35 ribonucleotides within a hammerhead ribozyme, while retaining at least some catalytic activity. (See Perreault et al, *Nature*, 344:565-567, 1990; Williams et al, Proc. *Natl. Acad. Sci. USA*, 89:918-921, 1992; Yang et al, *Biochemistry*, 31:5005-5009, 1992).

In vitro selection techniques have been applied to large populations of random-sequence DNAs, leading to the recovery of specific DNA "aptamers" that bind a target ligand with high affinity (Bock et al, *Nature*, 355:564-566, 1992); Ellington et al *Nature*, 355:850-852, 1992; Wyatt et al, *Proc. Natl. Acad. Sci. USA*, 91:1356-1360, 1994). Recently, two groups carried out the first NMR structural determination of an aptamer, a 15mer DNA that forms a G-quartet structure and binds the protein thrombin with high affinity (Wang et al, *Biochemistry*, 32:1899-1904, 1993; Macaya et al, *Proc. Natl. Acad. Sci. USA*, 90:3745-3749, 1993). These findings were corroborated by an X-ray crystallographic analysis (Padmanabhan et al, *J. Biol. Chem.*, 268:17651-17654, 1993).

The ability to bind a substrate molecule with high affinity and specificity is a prerequisite of a good enzyme. In addition, an enzyme must make use of well-positioned functional groups, either within itself or a cofactor, to promote a particular chemical transformation. Furthermore, the enzyme must remain unchanged over the course of the reaction and be capable of operating with catalytic turnover. Some would add the requirement that it be an informational macromolecule, comprised of subunits whose specific ordering is responsible for catalytic activity. While these criteria are open to debate on both semantic and chemical grounds, they serve to distinguish phenomena of chemical rate enhancement that range from simple solvent effects to biological enzymes operating at the limit of substrate diffusion (Albery et al, *Biochemistry*, 15:5631-5640, 1976).

As described in greater detail hereinbelow, we sought to develop a general method for rapidly obtaining DNA catalysts and DNA enzymes, starting from random sequences. As an initial target, we chose a reaction that we felt was well within the capability of DNA: the hydrolytic cleavage of an RNA phosphodiester, assisted by a divalent metal cofactor. This is the same reaction that is carried out by a variety of naturally-occurring RNA enzymes, including the hammerhead and hairpin motifs. (See, e.g., Forster et al, *Cell*, 49:211-220, 1987; Uhlenbeck, *Nature*, 328:596-600, 1987; Hampel et al, *Biochemistry*, 28:4929-4933, 1989).

It has recently been shown that, beginning with a randomized library of tRNA molecules, one can obtain ribozymes that have $Pb^{2+}$-dependent, site-specific RNA phosphoesterase activity at neutral pH (Pan et al, *Biochemistry*, 31:3887-3895, 1992; Pan et al, *Nature*, 358:560-563, 1992). This is analogous to the fortuitous self-cleavage reaction of yeast $tRNA^{Phe}$ (Dirheimer et al, *Biochimie*, 54:127-144, 1972), which depends on specific coordination of a $Pb^{2+}$ ion at a defined site within the tRNA. (See Rubin et al, *J. Biomol. Struct. Dyn.*, 1:639-646, 1983; Brown et al, *Biochemistry*, 24:4785-4801, 1985).

As disclosed herein, our goals included the development of DNAs that could carry out $Pb^{2+}$-dependent cleavage of a particular RNA phosphoester, initially presented within a short leader sequence attached to the 5' end of the DNA, and ultimately located within a separate molecule that could be cleaved in an intermolecular fashion with rapid catalytic turnover. These goals were successfully achieved, as described further below.

No assumptions were made as to how the DNA would interact with the target phosphoester and surrounding nucleotides. Beginning with a pool of approximately $10^{14}$ random 50mer sequences, in vitro selection was allowed to run its course. After five rounds of selection carried out over four days, the population as a whole had attained the ability to cleave the target phosphoester in the presence of 1 mM $Pb^{2+}$ at a rate of about 0.2 $min^{-1}$. This is an approximately $10^5$-fold increase compared to the spontaneous rate of cleavage under the same reaction conditions.

Individuals were isolated from the population, sequenced, and assayed for catalytic activity. Based on this information, the reaction was converted to an intermolecular format and then simplified to allow site-specific cleavage of a 19mer substrate by a 38mer DNA enzyme, in a reaction that proceeds with a turnover rate of 1 $min^{-1}$ at 23° C. and pH 7.0 in the presence of 1 mM PbOAc.

B. In Vitro Selection Scheme

Figure 1:
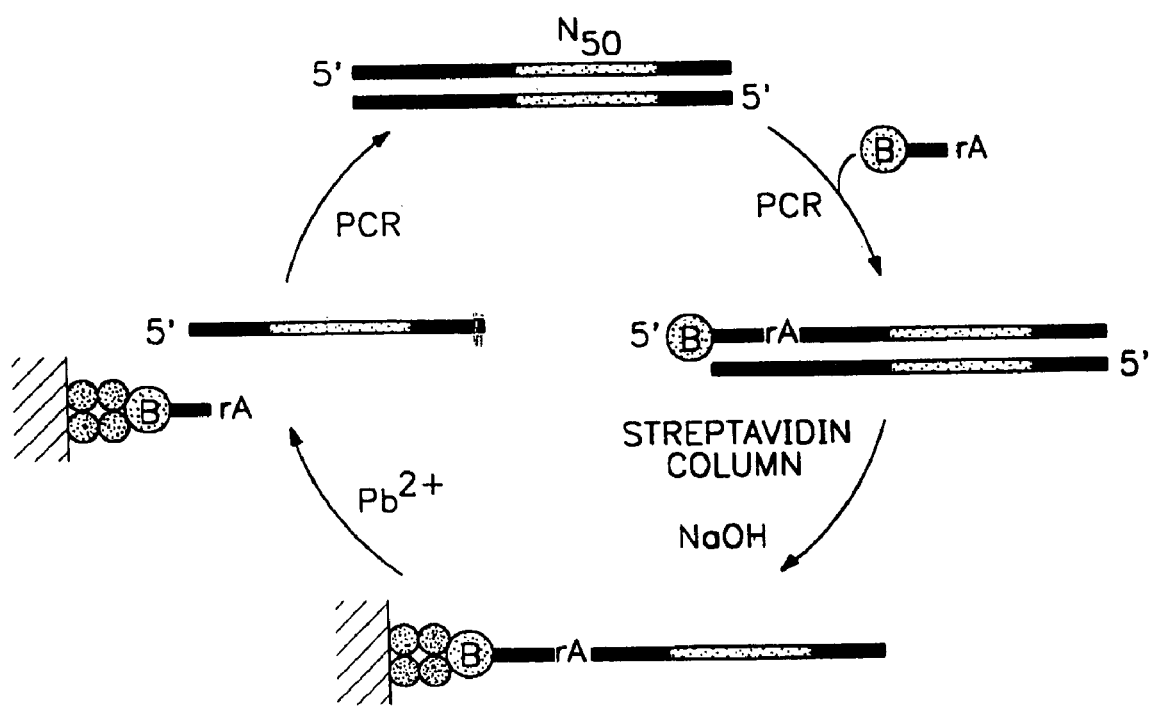
FIG. 1 illustrates a selective amplification scheme for isolation of DNAs that cleave a target RNA phosphoester. As shown, double-stranded DNA that contains a stretch of 50 random nucleotides (the molecule with "$N_{50}$" (SEQ ID NO 146) indicated above it) is amplified by PCR, employing a 5'-biotinylated DNA primer that is terminated at the 3' end by an adenosine ribonucleotide (rA). (The biotin label is indicated via the encircled letter "B".) This primer is extended by Taq polymerase to yield a DNA product that contains a single embedded ribonucleotide. The resulting double-stranded DNA is immobilized on a streptavidin matrix and the unbiotinylated DNA strand is removed by washing with 0.2 N NaOH. After re-equilibrating the column with a buffered solution, the column is washed with the same solution with added 1 mM PbOAc. DNAs that undergo $Pb^{2+}$-dependent self-cleavage are released from the column, collected in the eluant, and amplified by PCR. The PCR products are then used to initiate the next round of selective amplification.

A starting pool of approximately $10^{14}$ single-stranded DNA molecules was generated, all of which contain a 5' biotin moiety, followed successively by a fixed domain that includes a single ribonucleotide, a potential catalytic domain comprised of 50 random deoxyribonucleotides, and a second fixed domain that lay at the 3' terminus (FIG. 1).

The pool was constructed by a nested PCR (polymerase chain reaction) technique, beginning with synthetic DNA that contained 50 random nucleotides flanked by primer binding sites. The nested PCR primer was a 5'-biotinylated synthetic oligodeoxynucleotide with a 3'-terminal adenosine ribonucleotide. Ribonucleotide-terminated oligonucleotides efficiently prime template-directed elongation in the context of the PCR, in this case giving rise to an extension product that contains a single embedded ribonucleotide.

FIG. 1 illustrates a selective amplification scheme for isolation of DNAs that cleave a target RNA phosphoester. Double-stranded DNA containing a stretch of 50 random nucleotides is amplified via PCR, employing a 5'-biotinylated DNA primer (e.g., primer 3—3a or 3b) terminated at the 3' end by an adenosine ribonucleotide (represented by the symbol "N" or "rA", wherein both N and rA represent an adenosine ribonucleotide). This primer is extended by Taq polymerase to yield a DNA product that contains a single embedded ribonucleotide. The resulting double-stranded DNA is immobilized on a streptavidin matrix and the unbiotinylated DNA strand is removed by washing with 0.2 N NaOH. After re-equilibrating the column with a buffered solution, the column is washed with the same solution with added 1 mM PbOAc. DNAs that undergo $Pb^{2+}$-dependent self-cleavage are released from the column, collected in the eluant, and amplified by PCR. The PCR products are then used to initiate the next round of selective amplification.

The PCR products were passed over a streptavidin affinity matrix, resulting in noncovalent attachment of the 5'-biotinylated strand of the duplex DNA. The nonbiotinylated strand was removed by brief washing with 0.2 N NaOH, and the bound strand was equilibrated in a buffer containing 0.5 M NaCl, 0.5 M KCl, 50 mM $MgCl_2$, and 50 mM HEPES (pH 7.0) at 23° C. Next, 1 mM PbOAc was provided in the same buffer, allowing $Pb^{2+}$-dependent cleavage to occur at the target phosphoester, thereby releasing a subset of the DNAs from the streptavidin matrix. In principle, an individual DNA might facilitate its own release by various means, such as disruption of the interaction between biotin and streptavidin or cleavage of one of the deoxyribonucleotide linkages. It was felt that cleavage of the ribonucleoside 3'-O—P bond would be the most likely mechanism for release, based on the relative lability of this linkage, and that $Pb^{2+}$-dependent hydrolytic cleavage would allow release to occur most rapidly. In principle, however, the in vitro selection procedure should identify the most favorable release mechanism as well as those individuals best able to carry out that mechanism.

DNA molecules released from the matrix upon addition of $Pb^{2+}$ were collected in the eluant, concentrated by precipitation with ethanol, and subjected to nested PCR amplification. As in the construction of the starting pool of molecules, the first PCR amplification utilized primers that flank the random region (primers 1 and 2) and the second utilized a 5'-biotinylated primer (primer 3b) that has a 3'-terminal riboadenylate, thereby reintroducing the target RNA phosphoester. The entire selective amplification procedure requires 3-4 hours to perform.

The molecules are purified in three ways during each round of this procedure: first, following PCR amplification, by extracting twice with phenol and once with chloroform/isoamyl alcohol, then precipitating with ethanol; second, following attachment of the DNA to streptavidin, by washing away all the nonbiotinylated molecules under strongly denaturing conditions; and third, following elution with $Pb^{2+}$, by precipitating with ethanol. There is no gel electrophoresis purification step, and thus no selection pressure constraining the molecules to a particular length.

C. Selection of Catalytic DNA

Five successive rounds of in vitro selection were carried out, progressively decreasing the reaction time following addition of $Pb^{2+}$ in order to progressively increase the stringency of selection. During rounds 1 though 3, the reaction time was 1 hour; during round 4, the reaction time was 20 minutes; and during round 5, it was 1 minute. The starting pool of single-stranded DNAS, together with the population of molecules obtained after each round of selection, was assayed for self-cleavage activity under conditions identical to those employed during in vitro selection (see FIG. 2).

For this assay, the molecules were prepared with a 5'-$^{32}$P rather than a 5'-biotin moiety, allowing detection of both the starting material and the 5' cleavage product. Following a 5-minute incubation, there was no detectable activity in the initial pool (G0) or in the population obtained after the first and second rounds of selection. DNAs obtained after the third round (G3) exhibited a modest level of activity; this activity increased steadily, reaching approximately 50% self-cleavage for the DNAs obtained after the fifth round of selection (G5). Cleavage was detected only at the target phosphoester, even after long incubation times. This activity was lost if $Pb^{2+}$ was omitted from the reaction mixture.

Figure 2:
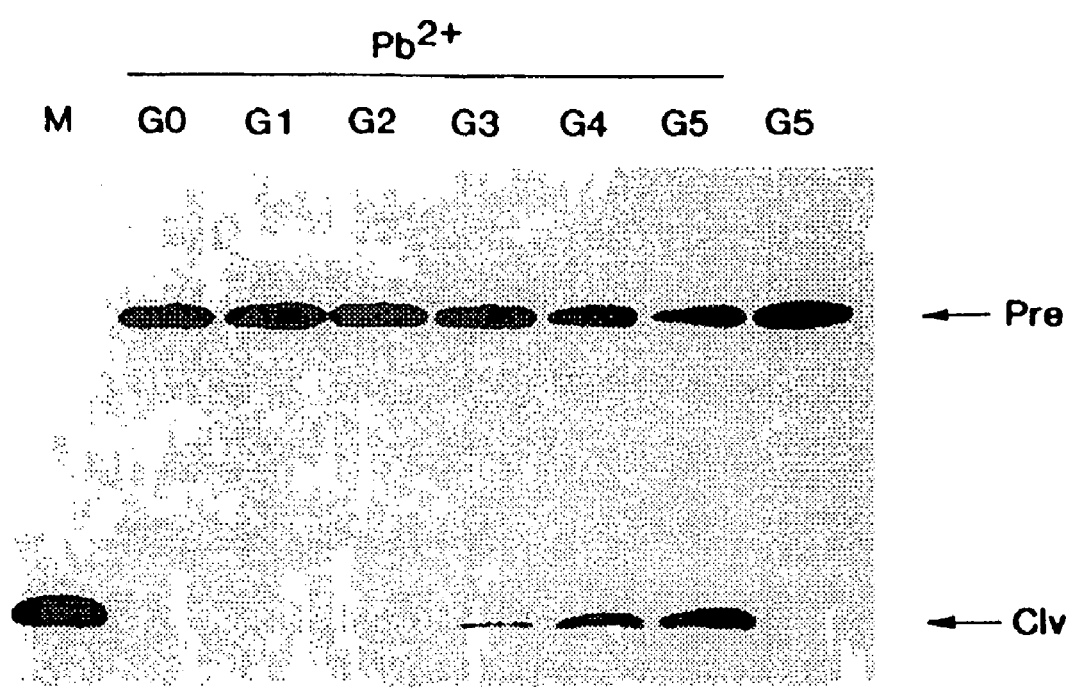
FIG. 2 illustrates self-cleavage activity of the starting pool of DNA (G0) and populations obtained after the first through fifth rounds of selection (G1-G5), in the presence of lead cation ($Pb^{2+}$). The symbol Pre represents 108-nucleotide precursor DNA (SEQ ID NO 4); Clv, 28-nucleotide 5'-cleavage product (SEQ ID NO 5); and M, primer 3a (SEQ ID NO 6), which corresponds in length to the 5'-cleavage product.

FIG. 2 illustrates the self-cleavage activity of the starting pool of DNA (G0) and populations obtained after the first through fifth rounds of selection (G1-G5). Reaction mixtures contained 50 mM $MgCl_2$, 0.5 M NaCl, 0.5 M KCl, 50 mM HEPES (pH 7.0 at 23° C.), and 3 nM [5'-$^{32}$P]-labeled DNA, incubated at 23° C. for 5 min either in the presence or in the absence of 1 mM PbOAc. The symbol Pre represents 108-nucleotide precursor DNA (SEQ ID NO 4); Clv, 28-nucleotide 5'-cleavage product (SEQ ID NO 5); and M, primer 3a (SEQ ID NO 6), corresponding in length to the 5'-cleavage product.

The 28-nucleotide 5' cleavage product (Clv) illustrated preferably has the sequence 5'-GGGACGAATTCTAATAC-GACTCACTATN-3', wherein "N" represents adenosine ribonucleotide with an additional 2',3'-cyclic phosphate on the 3' end (SEQ ID NO 5). In alternative embodiments, "N" represents adenosine ribonucleotide with an additional 2' or 3' phosphate on the 3' end of the molecule.

In FIG. 2, the "G0" lane "Pre" band comprises a sampling of 108-nucleotide precursor DNAs that each include 50 random nucleotides. Therefore, any given "Pre" sampling will contain a wide variety of precursor DNAs, and each sampling will likely differ from previous and subsequent samplings. The "G1" through "G5" lanes contain "Pre" bands that are increasingly enriched for catalytic DNA molecules, but still contain a large number of different DNA sequences (i.e., differing in the 50 nucleotide randomized domain). A sample of these different sequences from "G5 Pre" DNA is provided in FIG. 3.

Figure 3:
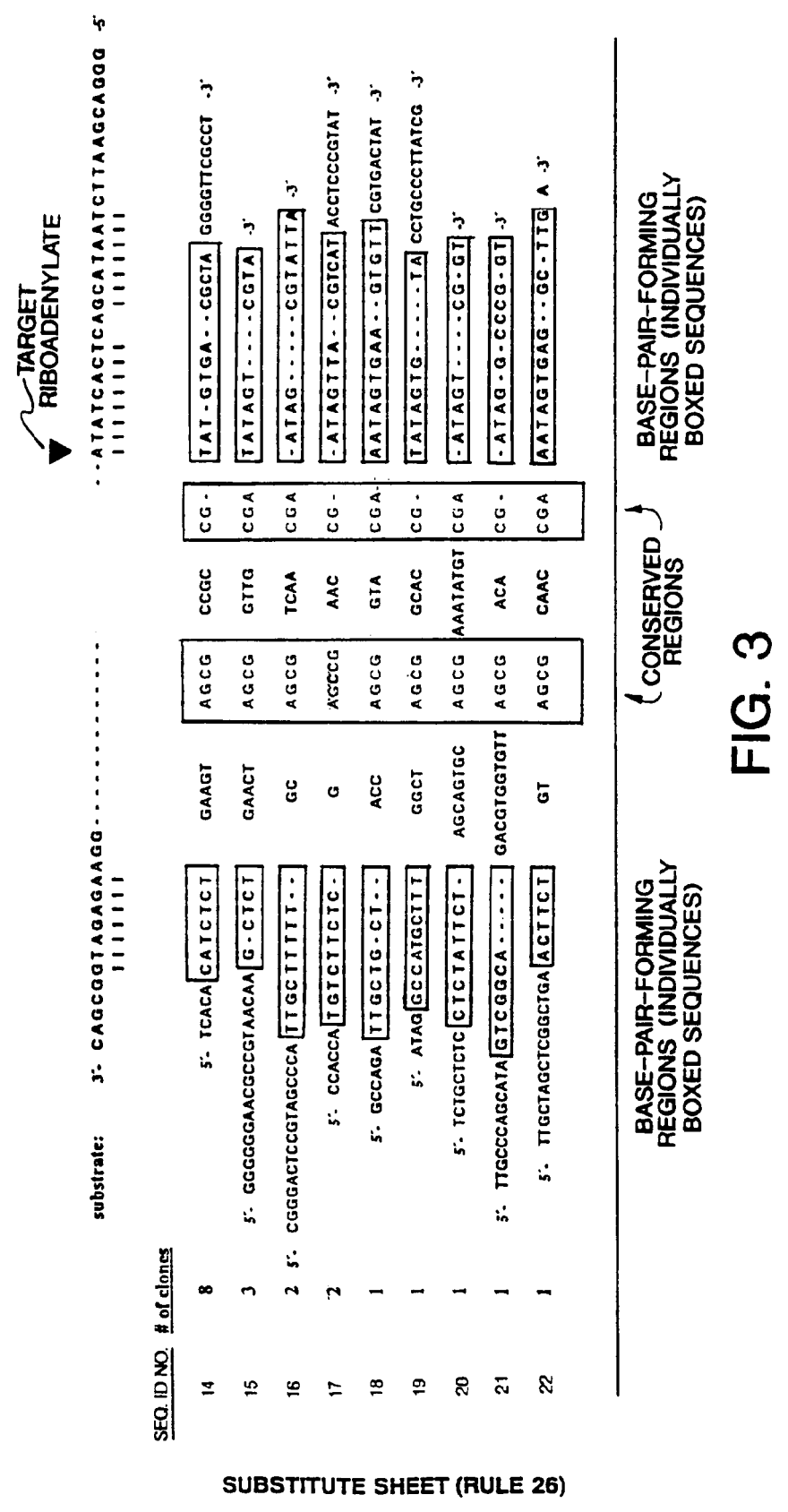

Shotgun cloning techniques were employed to isolate individuals from the G5 population; the complete nucleotide sequences of 20 of these subclones were then determined (see FIG. 3). (Also see Cadwell et al, *PCR Methods and Applications,* 2:28-33, 1992); and Cadwell et al, *PCR Methods and Applications,* 3(Suppl.):S136-S140, 1994). Of the 20 sequences, five were unique, two occurred twice, one occurred three times, and one occurred eight times. All of the individual variants share common sequence elements within the 50-nucleotide region that had been randomized in the starting pool of DNA. They all contain two presumed template regions, one with complementarity to a stretch of nucleotides that lies just upstream from the cleavage site and the other with complementarity to nucleotides that lie at least four nucleotides downstream. Between these two presumed template regions lies a variable domain of 1-11 nucleotides, followed by the fixed sequence 5'-AGCG-3', then a second variable domain of 3-8 nucleotides, and finally the fixed sequence 5'-CG-3' or 5'-CGA-3'. Nucleotides that lie outside of the two presumed template regions are highly variable in both sequence and length. In all of the sequenced subclones, the region corresponding to the 50 initially-randomized nucleotides remains a total of 50 nucleotides in length.

FIG. 3 illustrates the sequence alignment of individual variants isolated from the population after five rounds of selection. The fixed substrate domain (5'-GGGACGAAT-TCTAATACGACTCACTATxAGGAAGAGATGGCGAC-3' (SEQ ID NO:13), or 5'-GGGACGAATTCTAATACGACT-CACTATNGGAAGAGATGGCGAC-3', where N represents adenosine ribonucleotide) (SEQ ID NO 13) is shown at the top, with the target riboadenylate identified with an inverted triangle. Substrate nucleotides that are commonly involved in presumed base-pairing interactions are indicated by a vertical bar. Sequences corresponding to the 50 initially-randomized nucleotides are aligned antiparallel to the substrate domain. All of the variants are 3'-terminated by the fixed sequence 5'-CGGTAAGCTTGGCAC-3' (SEQ ID NO 1) ("primer site"; not shown). Nucleotides within the initially-randomized region that are presumed to form base pairs with the substrate domain are indicated on the right and left sides of the Figure; the putative base-pair-forming (or substrate binding) regions of the enzymatic DNA molecules are individually boxed in each sequence shown. The highly-conserved nucleotides within the putative catalytic domain are illustrated in the two boxed columns.

While it is anticipated that additional data will be helpful in constructing a meaningful secondary structural model of the catalytic domain, we note that, like the hammerhead and hairpin ribozymes, the catalytic domain of our enzymatic DNA molecules appears to contain a conserved core flanked by two substrate binding regions (or recognition domains) that interact with the substrate through base-pairing interactions. Similar to the hammerhead and hairpin ribozymes, catalytic DNAs also appear to require a short stretch of unpaired substrate nucleotides—in this case 5'-GGA-3'—between the two regions that are involved in base pairing.

It was also interesting to note that each of the nine distinct variants exhibited a different pattern of presumed complementarity with the substrate domain. In some cases, base pairing was contiguous, while in others it was interrupted by one or more noncomplementary pairs. The general tendency seems to be to form tighter interaction with the nucleotides that lie upstream from the cleavage site compared to those that lie downstream. Binding studies and site-directed mutagenesis analysis should enable us to gain further insights and to further substantiate this conjecture.

In order to gain further insight into the sequence requirements for catalytic function, the self-cleavage activity of six of the nine variants was tested and evaluated under the within-described selection conditions (see FIG. 3). Not surprisingly, the sequence that occurred in eight of the 20 subclones proved to be the most reactive, with a first-order rate constant of 1.4 $min^{-1}$. All of the studied variants were active in the self-cleavage assay and all gave rise to a single 5'-labeled product corresponding to cleavage at the target RNA phosphoester.

The dominant subclone was further analyzed under a variety of reaction conditions. Its self-cleavage activity was dependent on $Pb^{2+}$ but was unaffected if $Mg^{2+}$ was omitted from the reaction mixture. There was a requirement for a monovalent cation as well, which can be met by either $Na^+$ or $K^+$. The reaction rate increased linearly with increasing concentration of monovalent cation over the range of 0-1.0 M (r=0.998). Other variables that may affect the reaction, such as pH, temperature, and the presence of other divalent metals, are in the process of being evaluated further.

2. Materials and Methods

A. Oligonucleotides and Oligonucleotide Analogs

Synthetic DNAs and DNA analogs were purchased from Operon Technologies. The 19-nucleotide substrate, 5'-pT-CACTATrAGGAAGAGATGG-3' (SEQ ID NO:7) (or 5'-pT-CACTATNGGAAGAGATGG-3', wherein "N" represents adenosine ribonucleotide) (SEQ ID NO 7), was prepared by reverse-transcriptase catalyzed extension of 5'-pTCAC-TATrA-3' (SEQ ID NO:8) (or 5'-pTCACTATN-3', wherein "N" represents adenosine ribonucleotide) (SEQ ID NO 8), as previously described (Breaker et al, *Biochemistry,* 33:11980-11986, 1994), using the template 5'-CCATCTCTTCCTAT-AGTGAGTCCGGCTGCA-3' (SEQ ID NO 9). Primer 3, 5'-GGGACGAATTCTAATACGACTCACTATrA-3' (SEQ ID NO:6) (or 5'-GGGACGAATTCTAATACGACTCAC-TATN-3', wherein "N" represents adenosine ribonucleotide) (SEQ ID NO 6), was either 5'-labeled with [$\gamma$-$^{32}$P]ATP and T4 polynucleotide kinase (primer 3a) or 5'-thiophosphorylated with [$\gamma$-S]ATP and T4 polynucleotide kinase and subsequently biotinylated with N-iodoacetyl-N'-biotinylhexylenediamine (primer 3b).

B. DNA Pool Preparation

The starting pool of DNA was prepared by PCR using the synthetic oligomer 5'-GTGCCAAGCTTACCG-$N_5$'-GTCGCCATCTCTTCC-3' (SEQ ID NO 4), where N is an equimolar mixture of G, A, T and C. A 2-ml PCR, containing 500 pmoles of the randomized oligomer, 1,000 pmoles primer 1 (5'-GTGCCAAGCTTACCG-3', SEQ ID NO 10), 500 pmoles primer 2 (5'-CTGCAGAATTCTAATACGACTCAC-TATAGGAAGAGATGGCGAC-3', SEQ ID NO 11), 500 pmoles primer 3b, 10 µCi [$\alpha$-$^{32}$P]dATP, and 0.2 U µl$^{-1}$ Taq DNA polymerase, was incubated in the presence of 50 mM KCl, 1.5 mM $MgCl_2$, 10 mM Tris-HCl (pH 8.3 at 23° C.), 0.01% gelatin, and 0.2 mM of each dNTP for 1 min at 92° C., 1 min at 50° C., and 2 min at 72° C., then 5 cycles of 1 min at 92° C., 1 min at 50° C., and 1 min at 72° C. The resulting mixture was extracted twice with phenol and once with chloroform/isoamyl alcohol, and the DNA was isolated by precipitation with ethanol.

C. In Vitro Selection

The starting pool of DNA was resuspended in 500 μL of buffer A (1 M NaCl and 50 mM HEPES (pH 7.0 at 23° C.)) and was passed repeatedly over a streptavidin column (AffiniTip Strep 20, Genosys, The Woodlands, Tex.). The column was washed with five 100-μl volumes of buffer A, followed by five 100-μl volumes of 0.2 N NaOH, then equilibrated with five 100-μl volumes of buffer B (0.5 M NaCl, 0.5 M KCl, 50 mM $MgCl_2$, and 50 mM HEPES (pH 7.0 at 23° C.)). The immobilized single-stranded DNA was eluted over the course of 1 hr with three 20-μl volumes of buffer B with added 1 mM PbOAc. The entire immobilization and elution process was conducted at 23° C. The eluant was collected in an equal volume of buffer C (50 mM HEPES (pH 7.0 at 23° C.) and 80 mM EDTA) and the DNA was precipitated with ethanol.

The resulting DNA was amplified in a 100-μL PCR containing 20 pmoles primer 1, 20 pmoles primer 2, 0.05 U μl$^{-1}$ Taq polymerase, 50 mM KCl, 1.5 mM $MgCl_2$, 10 mM Tris-HCl (pH 8.3 at 23° C.), 0.01% gelatin, and 0.2 mM of each dNTP for 30 cycles of 10 sec at 92° C., 30 sec at 50° C., and 30 sec at 72° C. The reaction products were extracted twice with phenol and once with chloroform/isoamyl alcohol, and the DNA was recovered by precipitation with ethanol. Approximately 4 pmoles of the amplified DNA was added to a second, nested PCR containing 100 pmoles primer 1, 100 pmoles primer 3b, 20 μCi [α-$^{32}$P]dATP, and 0.1 μl$^{-1}$ Taq polymerase, in a total volume of 200 μL that was amplified for 10 cycles of 1 min at 92° C., 1 min at 50° C., and 1 min at 72° C. The PCR products were once more extracted and precipitated, and the resulting DNA was resuspended in 50 μL buffer A, then used to begin the next round of selection.

The second and third rounds were carried out as above, except that the nested PCR at the end of the third round was performed in a 100-μl volume. During the fourth round, the elution time following addition of Pb$^{2+}$ was reduced to 20 min (two 20-μL elution volumes) and only half of the recovered DNA was used in the first PCR, which involved only 15 temperature cycles. During the fifth round, the elution time was reduced to 1 min (two 20-μL elution volumes) and only one-fourth of the recovered DNA was used in the first PCR, which involved 15 temperature cycles. DNA obtained after the fifth round of selection was subcloned and sequenced, as described previously (Tsang et al, *Biochemistry*, 33:5966-5973, 1994).

D. Kinetic Analysis of Catalytic DNAs

Populations of DNA and various subcloned individuals were prepared with a 5'-$^{32}$P label by asymmetric PCR in a 25-μl reaction mixture containing 10 pmoles primer 3a, 0.5 pmoles input DNA, and 0.1 U μl$^{-1}$ Taq polymerase, under conditions as described above, for 10 cycles of 1 min at 92° C., 1 min at 50° C., and 1 min at 72° C. The resulting [5'-$^{32}$P]-labeled amplification products were purified by electrophoresis in a 10% polyacrylamide/8 M gel.

Self-cleavage assays were carried out following preincubation of the DNA in buffer B for 10 min. Reactions were initiated by addition of PbOAc to 1 mM final concentration and were terminated by addition of an equal volume of buffer C. Reaction products were separated by electrophoresis in a 10% polyacrylamide/8 M gel. Kinetic assays under multiple-turnover conditions were carried out in buffer B that included 50 μg ml$^{-1}$ BSA to prevent adherence of material to the vessel walls. Substrate and enzyme molecules were preincubated separately for 5 min in reaction buffer that lacked Pb$^{2+}$, then combined, and the reaction was initiated by addition of PbOAc to a final concentration of 1 mM.

3. Evolution of Deoxyribozymes that Cleave Intermolecularly

A. Conversion to an Intermolecular Format

Based on the variable pattern of presumed base-pairing interactions between the catalytic and substrate domains of the studied variants, it was felt that it would be reasonably straightforward to convert the DNA-catalyzed reaction to an intermolecular format. In doing so, we wished to simplify the two substrate-binding regions of the catalyst so that each would form an uninterrupted stretch of 7-8 base pairs with the substrate. In addition, we wished to provide a minimal substrate, limited to the two base-pairing regions and the intervening sequence 5'-GGA-3' (FIG. 4A).

Figure 4A:
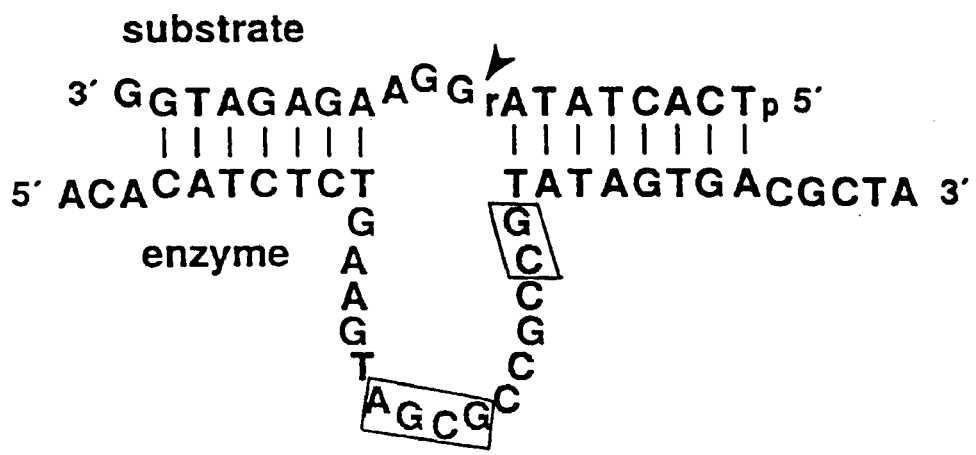
FIGS. 4A and 4B illustrate DNA-catalyzed cleavage of an RNA phosphoester in an intermolecular reaction that proceeds with catalytic turnover.
Figure 4B:
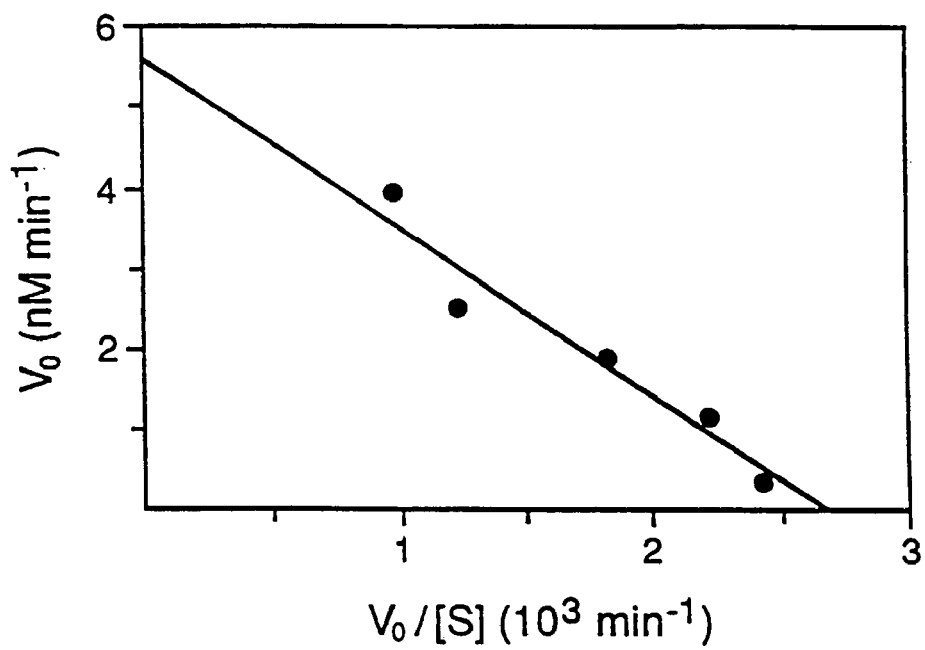

FIGS. 4A and 4B illustrate DNA-catalyzed cleavage of an RNA phosphoester in an intermolecular reaction that proceeds with catalytic turnover. FIG. 4A is a diagrammatic representation of the complex formed between the 19mer substrate and 38mer DNA enzyme. The substrate contains a single adenosine ribonucleotide ("rA" or "N", adjacent to the arrow), flanked by deoxyribonucleotides. The synthetic DNA enzyme is a 38-nucleotide portion of the most frequently occurring variant shown in FIG. 3. Highly-conserved nucleotides located within the putative catalytic domain are "boxed". As illustrated, one conserved sequence is "AGCG", while another is "CG" (reading in the 5'-3' direction).

FIG. 4B shows an Eadie-Hofstee plot used to determine $K_m$ (negative slope) and $V_{max}$ (y-intercept) for DNA-catalyzed cleavage of [5'-$^{32}$P]-labeled substrate under conditions identical to those employed during in vitro selection. Initial rates of cleavage were determined for reactions involving 5 nM DNA enzyme and either 0.125, 0.5, 1, 2, or 4 μM substrate.

In designing the catalytic domain, we relied heavily on the composition of the most reactive variant, truncating by two nucleotides at the 5' end and 11 nucleotides at the 3' end. The 15 nucleotides that lay between the two template regions were left unchanged and a single nucleotide was inserted into the 3' template region to form a continuous stretch of nucleotides capable of forming base pairs with the substrate. The substrate was simplified to the sequence 5'-<u>TCACTATrA</u>●<u>GGA AGAGATGG</u>-3' (SEQ ID NO:12) (or 5'-<u>TCACTATN</u>●<u>GGA AGAGATGG</u>-3', wherein "N" represents adenosine ribonucleotide) (SEQ ID NO 12), where the underlined nucleotides correspond to the two regions involved in base pairing with the catalytic DNA molecule.

The simplified reaction system, employing a 38mer catalytic DNA molecule (catalyst) comprised entirely of deoxyribonucleotides and a 19mer substrate containing a single ribonucleotide embedded within an otherwise all-DNA sequence, allows efficient DNA-catalyzed phosphoester cleavage with rapid turnover. Over a 90-minute incubation in the presence of 0.01 μM catalyst and 1 μM substrate, 46% of the substrate is cleaved, corresponding to 46 turnovers of the catalyst. A preliminary kinetic analysis of this reaction was carried out, evaluated under multiple-turnover conditions. The DNA catalyst exhibits Michaelis-Menten kinetics, with values for $k_{cat}$ and $K_m$ of 1 min$^{-1}$ and 2 μM, respectively (see FIG. 4B). The value for $K_m$ is considerably greater than the expected dissociation constant between catalyst and substrate based on Watson-Crick interactions. The substrate was incubated under identical reaction conditions (but in the absence of the catalyst); a value for $k_{uncat}$ of $4 \times 10^{-6}$ min$^{-1}$ was obtained. This is consistent with the reported value of $5 \times 10^{-3}$ min$^{-1}$ for hydrolysis of the more labile 1-nitrophenyl-1,2-propanediol in the presence of 0.5 mM $Pb^{2+}$ at pH 7.0 and 37° C. (Breslow et al, *Proc. Natl. Acad. Sci. USA,* 88:4080-4083, 1991).

It is now presumed that the phosphoester cleavage reaction proceeds via a hydrolytic mechanism involving attack by the ribonucleoside 2'-hydroxyl on the vicinal phosphate, generating a 5' product with a terminal 2'(3')-cyclic phosphate and 3' product with a terminal 5'-hydroxyl. In support of this mechanism, the 3'-cleavage product is efficiently phosphorylated with T4 polynucleotide kinase and [γ-$^{32}$P]ATP, consistent with the availability of a free 5'-hydroxyl.

B. Discussion

After five rounds of in vitro selection, a population of single-stranded DNA molecules that catalyze efficient $Pb^{2+}$-dependent cleavage of a target RNA phosphoester was obtained. Based on the common features of representative individuals isolated from this population, a simplified version of both the catalytic and substrate domains was constructed, leading to a demonstration of rapid catalytic turnover in an intermolecular context. Thus the 38mer catalytic domain provides an example of a DNA enzyme, or what might be termed a "deoxyribozyme".

Referring to this molecule as an enzyme, based on the fact that it is an informational macromolecule capable of accelerating a chemical transformation in a reaction that proceeds with rapid turnover and obeys Michaelis-Menten kinetics, may not satisfy everyone's notion of what constitutes an enzyme. Some might insist that an enzyme, by definition, must be a polypeptide. If, however, one accepts the notion of an RNA enzyme, then it seems reasonable to adopt a similar view concerning DNA enzymes. Considering how quickly we were able to generate this molecule from a pool of random-sequence DNAs, we expect that many other examples of synthetic DNA enzymes will appear in the near future.

The $Pb^{2+}$-dependent cleavage of an RNA phosphoester was chosen as an initial target for DNA catalysis because it is a straightforward reaction that simply requires the proper positioning of a coordinated $Pb^{2+}$-hydroxyl to facilitate deprotonation of the 2' hydroxyl that lies adjacent to the cleavage site. (See Pan et al, in *The RNA World,* Gesteland & Atkins (eds.), pp. 271-302, Cold Spring Harbor Laboratory Press, Cold Spring Harbor, N.Y. (1993).) $Pb^{2+}$ is known to coordinate to the N7 position of purines, the O6 position of guanine, the O4 position of uracil, and the N3 position of cytosine (Brown et al, *Nature,* 303:543-546, 1993). Thus, the differences in sugar composition and conformation of DNA compared to RNA seemed unlikely to prevent DNA from forming a well-defined $Pb^{2+}$-binding pocket.

A substrate that contains a single ribonucleotide within an otherwise all-DNA sequence was chosen because it provided a uniquely favored site for cleavage and insured that any resulting catalytic activity would be attributable solely to DNA. Substrate recognition appears to depend on two regions of base-pairing interactions between the catalyst and substrate. However, the unpaired substrate nucleotides, 5'-GGA-3', that lie between these two regions may play an important role in substrate recognition, metal coordination, or other aspects of catalytic function.

It is further anticipated that an all-RNA molecule, other RNA-DNA composites, and molecules containing one or more nucleotide analogs may be acceptable substrates. As disclosed herein, the within-described in vitro evolution procedures may successfully be used to generate enzymatic DNA molecules having the desired specificities; further analyses along these lines are presently underway.

In addition, studies to determine whether the presumed base-pairing interactions between enzyme and substrate are generalizable with respect to sequence are in progress, using the presently-described methods. The within-disclosed $Pb^{2+}$-dependent deoxyribozymes may also be considered model compounds for exploring the structural and enzymatic properties of DNA.

The methods employed in the present disclosure for the rapid development of DNA catalysts will have considerable generality, allowing us to utilize other cofactors to trigger the cleavage of a target linkage attached to a potential catalytic domain. In this regard, the development of $Mg^{2+}$-dependent DNA enzymes that specifically cleave target RNAs under physiological conditions is of interest, as is the development of DNA enzymes that function in the presence of other cations (see Example 4). Such molecules will provide an alternative to traditional antisense and ribozyme approaches for the specific inactivation of target mRNAs.

DNA thus joins RNA and protein on the list of biological macromolecules that are capable of exhibiting enzymatic activity. The full extent of DNA's catalytic abilities remains to be explored, but these explorations should proceed rapidly based on in vitro selection methods such as those employed in this study.

DNA enzymes offer several important advantages compared to other macromolecular catalysts. First, they are easy to prepare, in an era when most laboratories have access to an automated DNA synthesizer and the cost of DNA phosphoramidites has become quite modest. Second, they are very stable compounds, especially compared to RNA, thus facilitating their use in biophysical studies. Third, we expect that they can be adapted to therapeutic applications that at present make use of antisense DNAs that lack RNA-cleavage activity. In vitro selection could be carried out with DNA analogs, including compounds that are nuclease resistant such as phosphorothioate-containing DNA, so long as these analogs can be prepared in the form of a deoxynucleoside 5'-triphosphate and are accepted as a substrate by a DNA-dependent DNA polymerase. Finally, DNA enzymes offer a new window on our understanding of the macromolecular basis of catalytic function. It will be interesting, for example, to carry out comparative analyses of protein-, RNA-, and DNA-based enzymes that catalyze the same chemical transformation.

4. Other Families of Catalytic DNAs

A starting pool of DNA was prepared by PCR essentially as described in Example 2.B. above, except that the starting pool of DNA comprised molecules containing 40 random nucleotides. Thus, the starting pool of DNA described herein was prepared by PCR using the synthetic oligomer 5 GGG ACG AAT TCT AAT ACG ACT CAC TAT rA GG AAG AGA TGG CGA CAT CTC $N_{40}$GT GAC GGT AAG CTT GGC AC 3 (SEQ ID NO 23), where N is an equimolar mixture of G, A, T and C, and where the DNA molecules were selected for the ability to cleave the phosphoester following the target rA. (See FIG. 6A, also.)

Figure 5:
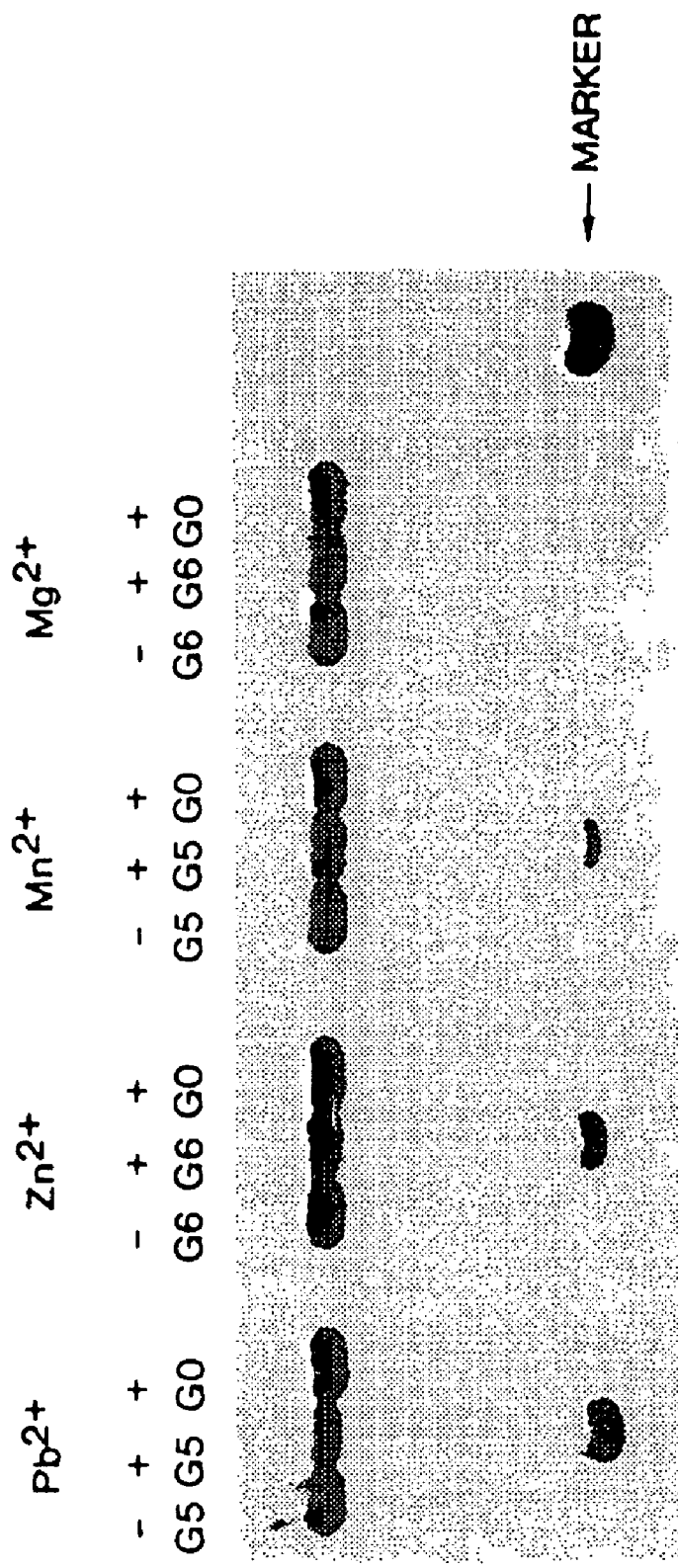
FIG. 5 is a photographic representation showing a polyacrylamide gel demonstrating specific endoribonuclease activity of four families of selected catalytic DNAs. Selection of a $Pb^{2+}$-dependent family of molecules was repeated in a side-by-side fashion as a control (first group). In the second group, $Zn^{2+}$ is used as the cation; in group three, the cation is $Mn^{2+}$; and in the fourth group, the cation is $Mg^{2+}$. A fifth site on the gel consists of the cleavage product alone, as a marker.

Selective amplification was carried out in the presence of either $Pb^{2+}$, $Zn^{2+}$, $Mn^{2+}$, or $Mg^{2+}$, thereby generating at least four "families" of catalytic DNA molecules. As illustrated in FIG. 5, catalytic DNA molecules demonstrating specific activity were generated in the presence of a variety of cations.

FIG. 5 is a photographic representation showing a polyacrylamide gel demonstrating specific endoribonuclease activity of four families of selected catalytic DNAs. Selection of a $Pb^{2+}$-dependent family of molecules was repeated in a side-by-side fashion as a control. In each group of three lanes, the first lane shows the lack of activity of the selected population in the absence of the metal cation, the second lane shows the observed activity in the presence of the metal cation, and the third lane shows the lack of activity of the starting pool (G0). At present, the order of reactivity is observed to be $Pb^{2+}>Zn^{2+}>Mn^{2+}>Mg^{2+}$, mirroring the $pK_a$ of the corresponding metal-hydroxide.

After either five (G5) or six (G6) rounds of selective amplification in the presence of the preselected divalent cation, the desired endonuclease activity was obtained. The following description of selective amplification in the presence of $Mg^{2+}$ is intended to be exemplary.

Six rounds of in vitro selective amplification were carried out, following the method described in Example 2 hereinabove, except that the divalent metal used was 1 mM $Mg^{2+}$ rather than 1 mM $Pb^{2+}$. (See also Breaker et al, *Chem. & Biol.,* 1:223-229, 1994), incorporated by reference herein, which describes essentially the same procedure.)

Individual clones were isolated following the sixth round, and the nucleotide sequence of 24 of these clones was determined. All of the sequences began with: 5' GGG ACG AAT TCT AAT ACG ACT CAC TAT rA GG AAG AGA TGG CGA CA (SEQ ID NO 139) and ended with: CGG TAA GCT TGG CAC 3' (SEQ ID NO 1).

The segment in the middle, corresponding to TCTC $N_{40}$ GTGA (SEQ ID NO 140) in the starting pool, varied as follows:

```
(13)  CCG CCC ACC TCT TTT ACG AGC CTG TAC GAA ATA
      GTG CTC TTG TTA GTA T
      (SEQ ID NO 24)

(5)   TCT CTT CAG CGA TGC ACG CTT GTT TTA ATG TTG
      CAC CCA TGT TAG TGA
      (SEQ ID NO 25)

(2)   TCT CAT CAG CGA TTG AAC CAC TTG GTG GAC AGA
      CCC ATG TTA GTG A
      (SEQ ID NO 26)

(1)   CCG CCC ACC TCT TTT ACG AGC CTG TAC GAA ATA
      GTG TTC TTG TTA GTA T
      (SEQ ID NO 27)

(1)   CCG CCC ACC TCT TTT ACG AGC CTG TAC GAA ATA
      GTG CTC TCG TTA GTA T
      (SEQ ID NO 28)

(1)   TCT CAG ACT TAG TCC ATC ACA CTC TGT GCA TAT
      GCC TGC TTG ATG TGA
      (SEQ ID NO 29)

(1)   -CT CTC ATC TGC TAG CAC GCT CGA ATA GTG TCA
      GTC GAT GTG A.
      (SEQ ID NO 30)
```

The initial number in parentheses indicates the number of clones having that particular sequence. Note that some mutations (highlighted in bold type) occurred at nucleotide positions other than those that were randomized initially.

The second sequence listed above (i.e., SEQ ID NO 25), which occurred in 5 of 24 clones, was chosen as a lead (i.e. principal) compound for further study. Its cleavage activity was measured in the presence of a 1 mM concentration of various divalent metals and 1 M NaCl at pH 7.0 and 23° C.:

| metal | $k_{obs}$ (min$^{-1}$) |
|---|---|
| none | n.d. |
| $Mg^{2+}$ | $2.3 \times 10^{-3}$ |
| $Mn^{2+}$ | $6.8 \times 10^{-3}$ |
| $Zn^{2+}$ | $4.2 \times 10^{-2}$ |
| $Pb^{2+}$ | $1.1 \times 10^{-2}$ |

Thus, the lead compound is active in the presence of all four divalent metals, even though it was selected for activity in the presence of $Mg^{2+}$. Conversely, DNA molecules that were selected for activity in the presence of $Mn^{2+}$, $Zn^{2+}$, or $Pb^{2+}$ did not show any activity in the presence of $Mg^{2+}$.

In addition, the population of DNAs obtained after six rounds of in vitro selection in the presence of $Mg^{2+}$, when prepared as all-phosphorothioate-containing DNA analogs, showed $Mg^{2+}$-dependent cleavage activity at an observed rate of $\sim 10^{-3}$ min$^{-1}$. The phosphorothioate-containing analogs were prepared enzymatically so as to have an $R_p$ configuration at each stereocenter. Such compounds are relatively resistant to degradation by cellular nucleases compared to unmodified DNA.

The lead compound was re-randomized at 40 nucleotide positions (underlined), introducing mutations at a frequency of 15% (5% probability of each of the three possible base substitutions). The re-randomized population was subjected to seven additional rounds of in vitro selection. During the last four rounds, molecules that were reactive in the presence of 1 mM $Pb^{2+}$ were removed from the population before the remainder were challenged to react in the presence of 1 mM $Mg^{2+}$. Individual clones were isolated following the seventh round and the nucleotide sequence of 14 of these clones was determined. All of the sequences began with: 5' GGG ACG AAT TCT AAT ACG ACT CAC TAT rA GG AAG AGA TGG CGA CAT CTC (SEQ ID NO 141), and ended with: GTG ACG GTA AGC TTG GCA C 3' (SEQ ID NO 142).

The segment in the middle, corresponding to the 40 partially-randomized positions ($N_{40}$, SEQ ID NO 143), varied as follows:

```
(4) TAC AGC GAT TCA CCC TTG TTT AAG GGT TAC ACC CAT
    GTT A
    (SEQ ID NO 31)

(2) ATC AGC GAT TAA CGC TTG TTT CAA TGT TAC ACC CAT
    GTT A
    (SEQ ID NO 32)

(2) TTC AGC GAT TAA CGC TTA TTT TAG CGT TAC ACC CAT
    GTT A
    (SEQ ID NO 33)

(1) ATC AGC GAT TCA CCC TTG TTT TAA GGT TGC ACC CAT
    GTT A
    (SEQ ID NO 34)

(1) ATC AGC GAT TCA CCC TTC TTT AAG CGT TAC ACC CAT
    GTT G
    (SEQ ID NO 35)

(1) ATC AGC GAT TCA CCC TTG TTT TAA GGT TAC ACC CAT
    GTT A
    (SEQ ID NO 36)

(1) ATC AGC GAT TAA CGC TTA TTT TAG CGT TAC ACC CAT
    GTT A
    (SEQ ID NO 37)

(1) ATC AGC GAT TAA CGC TTG TTT TAG TGT TGC ACC CAT
    GTT A
    (SEQ ID NO 38)

(1) ATC AGC GAT TAA CGC TTA TTT TAG CAT TAC ACC CAT
    GTT A.
    (SEQ ID NO 39)
```

The number in parentheses indicates the number of clones having that particular sequence. Nucleotides shown in bold are those that differ compared to the lead compound.

Formal analysis of the cleavage activity of these clones is ongoing. The population as a whole exhibits $Mg^{2+}$-dependent cleavage activity at an observed rate of ~$10^{-2}$ min$^{-1}$, with a comparable level of activity in the presence of $Pb^{2+}$.

FIGS. 6A and 6B provide two-dimensional illustrations of a "progenitor" catalytic DNA molecule and one of several catalytic DNA molecules obtained via the selective amplification methods disclosed herein, respectively. FIG. 6A illustrates an exemplary molecule from the starting pool, showing the overall configuration of the molecules represented by SEQ ID NO 23. As illustrated, various complementary nucleotides flank the random ($N_{40}$) (SEQ ID NO 143) region.

FIG. 6B is a diagrammatic representation of one of the $Mg^{2+}$-dependent catalytic DNA molecules (or "DNAzymes") generated via the within-described procedures. The location of the ribonucleotide in the substrate nucleic acid is indicated via the arrow. (The illustrated molecule includes the sequence identified herein as SEQ ID NO 25, as well as "beginning" and "ending" sequences of SEQ ID NO 23.)

Endonuclease activity is continuing to be enhanced in each of the aforementioned "families" via in vitro evolution, as disclosed herein, so it is anticipated that enzymatic DNA molecules of increasingly desirable specificities may be generated successfully using the within-disclosed guidelines.

5. Cleavage of Larger RNA Sequences

As an extension of the foregoing, we have developed DNA enzymes that cleave an all-RNA substrate, rather than a single ribonucleotide embedded within an otherwise all-DNA substrate as demonstrated above. (Also see Breaker et al, *Chem. & Biol.*, 1:223-229, 1994); Breaker et al, *Chem. & Biol.*, 2:655-660, 1995). As a target sequence, we chose a stretch of 12 highly-conserved nucleotides within the U5 LTR region of HIV-1 RNA, having the sequence 5' GUAACUAGAGAU 3' (SEQ ID NO 49).

Following the methods described in the previous examples, we generated a pool of $10^{14}$ DNA molecules that have the following composition:

```
                                              (SEQ ID NO 50)
5'- GGAAAA r(GUAACUAGAGAU) GGAAGAGATGGCGAC N₅₀

CGGTAAGCTTGGCAC -3',
``` where N is an equimolar mixture of the deoxyribonucleotides G, A, T, and C, and where the sequence identified as "r(GUAACUAGAGAU)" is comprised of ribonucleotides. (Optionally, one may alter the initial 5' nucleotide sequence, e.g., by adding an additional dA residue to the sequence preceding the ribonucleotide portion at the 5' end, thus causing the initial sequence to read "GGAAAAA" and causing SEQ ID NO 50 to be 99 residues in length. Clearly, this is but one example of the modifications that may be made in order to engineer specific enzymatic DNA molecules, as disclosed in detail herein.)

The initial library was generated by template-directed extension of 50 pmols of 5'-biotin-d(GGAAAAA)r(GUAACUAGAGAU)d(GGAAGAGATGGCGAC)-3' (SEQ ID NO 144) on 100 pmols of 5'-GTGCCAAGCTTACCG-N50-GTCGCCATCTCTTCC-3' (SEQ ID NO 4) (N=G, A, T or C), in a 50-ul reaction mixture containing 10 U ul$^{-1}$ Superscript II reverse transcriptase (RT; Gibco BRL), 3 mM MgCl2, 75 mM KCl, 50 mM Tris*HCl (pH 8.3), and 0.2 mM of each dNTP. A trace amount of [5'-32P]-labeled primer was included in the reaction mixture to allow extension efficiency to be monitored. All components except RT were combined, incubated at 65° C. for 5 min, then cooled to 45° C. over 10 min. RT was added and the mixture was incubated at 45° C. for 45 min, then quenched by addition of Na2 EDTA. NaCl was added to a final concentration of 1 M and the extension products were immobilized by repeated passing through four streptavidin affinity columns (Genosys). The columns were washed with five 100-ul volumes of wash buffer (1 M NaCl, 50 mM Tris*HCl (pH 7.5), 0.1 mM Na2EDTA), followed by five 100-ul volumes of 0.1 N NaOH and five 100-ul volumes of wash buffer at 37° C., then eluted at 37° C. over 1 hr with three 20-ul aliquots of reaction buffer (10 mM MgCl2, 1 M NaCl, 50 mM Tris*HCl (pH 7.5)). Eluted molecules were recovered and amplified by the polymerase chain reaction (PCR) using the primers 5'-biotin-GGAAGAGATGGCGAC-3' (SEQ ID NO 145) and 5'-GTGCCAAGCTTACCG-3' (SEQ ID NO 10). The PCR products were immobilized on streptavidin columns, as above, which were washed with five 100-ul volumes of wash buffer and eluted with 40 ul of 0.1 N NaOH to obtain the non-biotinylated strand. The isolated DNAs were ethanol precipitated and used as templates in a primer extension reaction to begin the next round of selection. Rounds 2-10 were carried out as above, except that the reaction scale was reduced five-fold during the extension step and two-fold during PCR.

The enzymatic DNA molecules thus produced were selected for their ability to cleave a phosphoester that lies within the embedded RNA target sequence. Ten rounds of in vitro selective amplification were carried out, based on the enzymatic DNA molecules' activity in the presence of 10 mM $Mg^{2+}$ at pH 7.5 and 37° C. During the selection process, there was competition for "preferred" cleavage sites as well as for the "best" catalyst that cleaves at each such preferred site. Two sites and two families of catalysts emerged as possessing the most efficient cleavage capabilities (see FIG. 7).

FIG. 7 illustrates some of the results of ten rounds of in vitro selective amplification carried out essentially as described herein. As shown, two sites and two families of catalysts emerged as displaying the most efficient cleavage of the target sequence. Cleavage conditions were essentially as indicated in FIG. 7, namely, 10 mM $Mg^{2+}$, pH 7.5, and 37°; data collected after the reaction ran for 2 hours is shown. Cleavage (%) is shown plotted against the number of generations (here, 0 through 10). The number/prevalence of catalytic DNA molecules capable of cleaving the target sequence at the indicated sites in the substrate is illustrated via the vertical bars, with cleavage at G↓UAACUAGAGAU shown by the striped bars, and with cleavage at GUAACUA↓GAGAU illustrated via the open (lightly-shaded) bars. In FIG. 7, as herein, the arrow (↓) indicates the site between two neighboring nucleotides at which cleavage occurs.

Various individuals from the population obtained after the 8th and 10th rounds of selective amplification were cloned. The nucleotide sequences of 29 individuals from the 8th round and 32 individuals from the 10th round were then determined (see Tables 2 and 3, respectively).

Under the heading "Nucleotide Sequence" in each of Tables 2 and 3 is shown the portion of each identified clone that corresponds to the 50 nucleotides that were randomized in the starting pool (i.e., $N_{50}$ (SEQ ID NO 146)); thus, the entire nucleotide sequence of a given clone generally includes the nucleotide sequences preceding, following, and including the "$N_{50}$" (SEQ ID NO 146) segment, presuming the substrate sequence is attached and that self-cleavage has not occurred. For example, the entire sequence of a (non-self-cleaved) clone may generally comprise residue nos. 1-33 of SEQ ID NO 50, followed by the residues representing the randomized $N_{50}$ (SEQ ID NO 146) region, followed by residue nos. 84-98 of SEQ ID NO 50, or by residue nos. 1-34 of SEQ ID NO 51, followed by the residues representing the randomized $N_{50}$ (SEQ ID NO 146) region, followed by residue nos. 85-99 of SEQ ID NO 51. It is believed, however, that the $N_{50}$ (SEQ ID NO 146) (or $N_{40}$ (SEQ ID NO 143)) region—or a portion thereof—of each clone is particularly important in determining the specificity and/or activity of a particular enzymatic DNA molecule. This is particularly evident in reactions in which the substrate and the DNAzyme are separate molecules (see, e.g., FIGS. 8 and 9).

Clone numbers are designated as 8-x or 10-x for individuals obtained after the 8th or 10th rounds, respectively. SEQ ID NOS are also listed and correspond to the "$N_{50}$" (SEQ ID NO 146) region of each clone.

TABLE 2

Cloned Individuals from 8th Round of Amplification

| Clone No. | SEQ ID NO | "$N_{50}$" Nucleotide Sequence (5'→3') |
|---|---|---|
| 8-2 | 52 | CCA ATA GTG CTA CTG TGT ATC TCA ATG CTG GAA ACA CGG GTT ATC TCC CG |
| 8-4 | 53 | CCA AAA CAG TGG AGC ATT ATA TCT ACT CCA CAA AGA CCA CTT TTC TCC CG |
| 8-5[1] | 54 | ATC CGT ACT AGC ATG CAG ACA GTC TGT CTG CTT TTT CAT TAC TCA CTC CC |
| 8-14 | 55 | CAA TTC ATG ATG ACC AAC TCT GTC AAC ACG CGA ACT TTT AAC ACT GGC A |
| 8-17[2] | 56 | CTT CCA CCT TCC GAG CCG GAC GAA GTT ACT TTT TAT CAC ACT ACG TAT TG |
| 8-3 | 57 | GGC AAG AGA TGG CAT ATA TTC AGG TAA CTG TGG AGA TAC CCT GTC TGC CA |
| 8-6 | 58 | CTA GAC CAT TCA CGT TTA CCA AGC TAT GGT AAG AAC TAG AAT CAC GCG TA |
| 8-8 | 59 | CGT ACA CGT GGA AAA GCT ATA AGT CAA GTT CTC ATC ATG TAC CTG ACC GC |
| 8-10 | 60 | CAG TGA TAC ATG AGT GCA CCG CTA CGA CTA AGT CTG TAA CTT ATT CTA CC |
| 8-22 | 61 | ACC GAA TTA AAC TAC CGA ATA GTG TGG TTT CTA TGC TTC TTC TTC CCT GA |
| 8-11 | 62 | CAG GTA GAT ATA ATG CGT CAC CGT GCT TAC ACT CGT TTT ATT AGT ATG TC |
| 8-21 | 63 | CCC TAC AAC ACC ACT GGG CCC AAT TAG ATT AAC GCT ATT TTA TAA CTC G |
| 8-12 | 64 | CCA AAC GGT TAT AAG ACT GAA AAC TCA ATC AAT AGC CCA ATC CTC GCC C |
| 8-13 | 65 | CAC ATG TAT ACC TAA GAA ATT GGT CCC GTA GAC GTC ACA GAC TTA CGC CA |
| 8-23 | 66 | CAC AAC GAA AAC AAT CTT CCT TGG CAT ACT GGG GAG AAA GTC TGT TGT CC |
| 8-40 | 67 | CAC ACG AAC ATG TCC ATT AAA TGG CAT TCC GTT TTT CGT TCT AGA TAT GC |
| 8-24 | 68 | CAG AAC GAG GGT CTT GTA AGA CTA CAC CTC CTG AGT GAC AAT AAT CCT G |
| 8-26 | 69 | CAC TAC AGC CTG ATA TAT ATG AAG AAC AGG CAA CAA GCT TAT GCA CTG G |
| 8-27 | 70 | GGG TAC ATT TAT GAT TCT CTT ATA AAG AGA ATA TCG TAC TCT TTT CCC CA |

TABLE 2-continued

Cloned Individuals from 8th Round of Amplification

| Clone No. | SEQ ID NO | "$N_{50}$" Nucleotide Sequence (5'→3') |
|---|---|---|
| 8-28 | 71 | CCA AAG TAC ATT CCA ACC CCT TAT ACG TGA AAC TTC CAG TAG TTT CCT A |
| 8-29 | 72 | CTT GAA GAT CCT CAT AAG ACG ATT AAA CAA TCC ACT GGA TAT AAT CCG GA |
| 8-34 | 73 | CGA ATA GTG TCC ATG ATT ACA CCA ATA ACT GCC TGC CTA TCA TGT TTA TG |
| 8-35 | 74 | CCA AGA GAG TAT CGG ATA CAC TTG GAA CAT AGC TAA CTC GAA CTG TAC CA |
| 8-36 | 75 | CCA CTG ATA AAT AGG TAA CTG TCT CAT ATC TGC CAA TCA TAT GCC GTA |
| 8-37 | 76 | CCC AAA TTA TAA ACA ATT TAA CAC AAG CAA AAG GAG GTT CAT TGC TCC GC |
| 8-39 | 77 | CAA TAA ACT GGT GCT AAA CCT AAT ACC TTG TAT CCA AGT TAT CCT CCC CC |

[1]identical to 10-4, 10-40
[2]identical to 8-20, 8-32, 8-38, 10-1, 10-34; 1 mutation to 10-11; 3 mutations to 10-29

TABLE 3

Cloned Individuals from 10th Round of Amplification

| Clone No. | SEQ ID NO | "$N_{50}$" Nucleotide Sequence (5'→3') |
|---|---|---|
| 10-3[3] | 78 | CCG AAT GAC ATC CGT AGT GGA ACC TTG CTT TTG ACA CTA AGA AGC TAC AC |
| 10-10 | 79 | CCA TAA CAA ATA CCA TAG TAA AGA TCT GCA TTA TAT TAT ATC GGT TCA CC |
| 10-12 | 80 | CAG AAC AAA GAT CAG TAG CTA AAC ATA TGG TAC AAA CAT ACC ATC TCG CA |
| 10-14 | 81 | CCT TTA GTT AGG CTA GCT ACA ACG ATT TTT CCC TGC TTG GCA ACG ACA C |
| 10-15 | 82 | CTC CCT ACG TTA CAC CAG CGG TAC GAA TTT TCC ACG AGA GGT AAT CCG CA |
| 10-19 | 83 | CGG CAC CTC TAG TTA GAC ACT CCG GAA TTT TTC CCC |
| 10-39 | 84 | CGG CAC CTC TAG TTA GAC ACT CCG GAA TTT TAG CCT ACC ATA GTC CGG T |
| 10-23 | 85 | CCC TTT GGT TAG GCT AGC TAC AAC GAT TTT TCC CTG CTT GAA TTG TA |
| 10-27[4] | 86 | CCC TTT GGT TAG GCT AGC TAC AAC GAT TTT TCC CTG CTT GAC CTG TTA CGA |
| 10-31 | 87 | CCT TTA GTT AGG CTA GCT ACA ACG ATT TTT CCC TGC TTG GAA CGA CAC |
| 10-18 | 88 | CAT GGC TTA ATC ATC CTC AAT AGA AGA CTA CAA GTC GAA TAT GTC CCC CC |
| 10-20 | 89 | CAA CAG AGC GAG TAT CAC CCC CTG TCA ATA GTC GTA TGA AAC ATT GGG CC |
| 10-6 | 90 | TAC CGA CAA GGG GAA TTA AAA GCT AGC TGG TTA TGC AAC CCT TTT CGC A |

TABLE 3-continued

Cloned Individuals from 10th Round of Amplification

| Clone No. | SEQ ID NO | "N$_{50}$" Nucleotide Sequence (5'→3') |
|---|---|---|
| 10-7 | 91 | CTC GAA ACA GTG ATA TTC TGA ACA AAC GGG TAC TAC GTG TTC AGC CCC C |
| 10-8 | 92 | CCA ATA ACG TAA CCC GGT TAG ATA AGC ACT TAG CTA AGA TGT TTA TCC TG |
| 10-16 | 93 | CAA TAC AAT CGG TAC GAA TCC AGA AAC ATA ACG TTG TTT CAG AAT GGT CC |
| 10-21 | 94 | GCA ACA ACA AGA ACC AAG TTA CAT ACA CGT TCA TCT ATA CTG AAC CCC CA |
| 10-24 | 95 | CCT TTG AGT TCC TAA ATG CCG CAC GGT AAG CTT GGC ACA CTT TGA CTG TA |
| 10-28 | 96 | CAA AGA TCT CAC TTT GGA AAT GCG AAA TAT GTA TAT TCG CCC TGT CTG C |
| 10-33 | 97 | CCA CGT AGA ATT ATC TGA TTT ATA ACA TAA CGC AGG ATA ACT CTC GCC CA |
| 10-35 | 98 | CAC AAG AAA GTG TCG TCT CCA GAT ATT TGA GTA CAA GGA ACT ACG CCC |
| 10-36 | 99 | CAT GAA GAA ATA GGA CAT TCT ACA GGC TGG ACC GTT ACT ATG CCT GTA GG |
| 10-37 | 100 | CAT AGG ATA ATC ATG GCG ATG CTT ATG ACG TGT ACA TCT ATA CCT T |
| 10-38 | 101 | CAG ATG ATC TTC CTT TAA AGA CTA CCC TTT AAA GAA ACA TAA GGT ACC CC |

[3]1 mutation to 10-5
[4]1 mutation to 10-30

The self-cleavage activity of various clones was subsequently measured. Clones 8-5, 8-17, and 10-3 were found to cleave efficiently at the site 5' GUAACU↓AGAGAU 3' (SEQ ID NO 49), while clones 10-14, 10-19 and 10-27 were found to cleave efficiently at the site 5' G↓UAACUAGAGAU 3' (SEQ ID NO 49). When the RNA portion of the molecule was extended to the sequence 5' GGAAAAAGUAACUA-GAGAUGGAAG 3' (SEQ ID NO 135), clones 8-17, 10-14, and 10-27 retained full activity, while clones 8-5, 10-3, and 10-19 showed diminished activity. Subsequently, clone 10-23 was found to exhibit a high level of activity in the self-cleavage reaction involving the extended RNA domain.

It should also be noted, in the event one of skill in the relevant art does not appreciate same, that the nucleotide sequences preceding and following the "N$_{50}$" (SEQ ID NO 146) segments of the polynucleotide molecules engineered according to the teachings of the present invention disclosure, i.e, the substrate binding regions flanking the "N$_{50}$" (SEQ ID NO 146) region, may be altered in a variety of ways in order to generate enzymatic DNA molecules of particular specificities, such as by length, nucleotide sequence, type of nucleic acid, and the like. For example, while residue nos. 1-24 of SEQ ID NO 51 are described herein as RNA nucleotides, they may alternatively comprise DNA, RNA, or composites thereof. (Thus, for example, SEQ ID NO 51 could easily be altered so that nucleic acid residue nos. 1-7 would comprise DNA, residue nos. 8-19 would comprise RNA, residue nos. 20-99 would comprise DNA, and so on.) Similarly, the nucleotides following the "N$_{50}$" (SEQ ID NO 146) region may comprise RNA, DNA, or composites thereof. The length of the regions preceding and following the "N$_{50}$" (SEQ ID NO 146) (or "N$_{40}$" (SEQ ID NO 143)—see Example 4) region(s) may also be varied, as disclosed herein. Further, sequences preceding and/or following N$_{50}$ (SEQ ID NO 146) or N$_{40}$ (SEQ ID NO 143) regions may be shortened, expanded, or deleted in their entirety.

Moreover, as noted above, we selected a specific region of HIV-1 RNA as the target sequence in the methods described in this Example; such a sequence is not the only sequence one may use as a target. Clearly, one of skill in the relevant art may follow our teachings herein to engineer and design enzymatic DNA molecules with specificity for other target sequences. As disclosed herein, such target sequences may be constructed or inserted into larger sequences comprising DNA, RNA, or composites thereof, as illustrated by SEQ ID NOS 50 and 51.

The self-cleavage reaction was easily converted to an intermolecular cleavage reaction by dividing the enzyme and substrate domains into separate molecules. Clones 8-17 and 10-23 were chosen as prototype molecules. Both were shown to act as DNA enzymes in the cleavage of a separate all-RNA substrate in a reaction that proceeds with multiple turnover (FIG. 8). The substrate binding arms were subsequently reduced to 7 base-pairs on each side of the unpaired nucleotide that demarcates the cleavage site (FIG. 9).

FIG. 8 illustrates the nucleotide sequences, cleavage sites, and turnover rates of two catalytic DNA molecules of the present invention, clones 8-17 and 10-23. Reaction conditions were as shown, namely, 10 mM $Mg^{2+}$, pH 7.5, and 37° C. The DNAzyme identified as clone 8-17 is illustrated on the left, with the site of cleavage of the RNA substrate indicated by the arrow. The substrate sequence (5'-GGAAAAAGUAACUAGAGAUGGAAG-3' (SEQ ID NO 135)—which is separate from the DNAzyme (i.e., intermolecular cleavage is shown)—is labeled as such. Similarly, the DNAzyme identified herein as 10-23 is shown on the right, with the site of cleavage of the RNA substrate indicated by the arrow. Again, the substrate sequence is indicated. For the 8-17 enzyme, the turnover rate was approximately 0.6 $hr^{-1}$; for the 10-23 enzyme, the turnover rate was approximately 1 $hr^{-1}$.

As illustrated in FIG. 8, the nucleotide sequence of the clone 8-17 catalytic DNA molecule capable of cleaving a separate substrate molecule was as follows: 5'-CTTCCAC-CTTCCGAGCCGGACGAAGTTACTTTTT-3' (SEQ ID NO 134). In that same figure, the nucleotide sequence of the clone 10-23 catalytic DNA molecule capable of cleaving a separate substrate molecule was as follows: 5'-CTTTGGTTAG-GCTAGCTACAACGATTTTTCC-3' (SEQ ID NO 136).

FIG. 9 further illustrates the nucleotide sequences, cleavage sites, and turnover rates of two catalytic DNA molecules of the present invention, clones 8-17 and 10-23. Reaction conditions were as shown, namely, 10 mM $Mg^{2+}$, pH 7.5, and 37° C. As in FIG. 8, the DNAzyme identified as clone 8-17 is illustrated on the left, with the site of cleavage of the RNA substrate indicated by the arrow. The substrate sequence (5'-GGAAAAAGUAACUAGAGAUGGAAG-3' (SEQ ID NO 135))—which is separate from the DNAzyme (i.e., intermolecular cleavage is shown)—is labeled as such. Similarly, the DNAzyme identified herein as 10-23 is shown on the right, with the site of cleavage of the RNA substrate indicated by the arrow. Again, the substrate sequence is indicated. For the 8-17 enzyme, $k_{obs}$ was approximately 0.002 $min^{-1}$; for the 10-23 enzyme, the value of $k_{obs}$ was approximately 0.01 $min^{-1}$.

As illustrated in FIG. 9, the nucleotide sequence of the clone 8-17 catalytic DNA molecule capable of cleaving a separate substrate molecule was as follows: 5'-CCACCTTC-CGAGCCGGACGAAGTTACT-3' (SEQ ID NO 138). In that same figure, the nucleotide sequence of the clone 10-23 catalytic DNA molecule capable of cleaving a separate substrate molecule was as follows: 5'-CTAGTTAGGCTAGCTA-CAACGATTTTTCC-3' (SEQ ID NO 137) (residue nos. 5-33 of SEQ ID NO 85, with "CTA" substituted for "TTG" at the 5' end).

The catalytic rate of the RNA-cleaving DNA enzymes has yet to be fully optimized. As disclosed above and as reported in previous studies, we have been able to improve the catalytic rate by partially randomizing the prototype molecule and carrying out additional rounds of selective amplification. We have found, however, that the $K_m$ for $Mg^{2+}$ is approximately 5 mM and 2 mM for the 8-17 and 10-23 DNA enzymes, respectively, measured at pH 7.5 and 37° C.; this is certainly compatible with intracellular conditions.

6. Preparation of a Universal Substrate Enzyme

The foregoing has shown that an enzyme of the present invention has the ability to catalytically cleave target nucleic acids having preselected sequences. Furthermore, an enzyme is shown to cleave a nucleic acid which is all DNA, or which has a ribonucleotide (i.e., an RNA component) imbedded within a deoxyribonucleotide (i.e., DNA) sequence, or which is entirely DNA. In addition, it is seen that the substrate can be altered and an enzyme is prepared which can cleave that substrate.

By the present invention, an enzyme is provided that can cleave any targeted substrate, i.e., one containing a preselected nucleotide sequence in the length range of about 10-30 nucleotides, in a kinetic manner that is efficient and specific under physiological conditions. This enzyme is easy to manufacture and inexpensive, and is useful for inactivation of target RNA, particularly messenger RNA (mRNA), for probing the structure of RNA and for the manipulation of recombinant RNA, such as a sequence-specific endoribonuclease.

For inactivation of RNAs, the enzyme is particularly useful for inactivation of target cellular RNAs, such as an "antisense" oligodeoxynucleotide can be used, to block mRNA function. However, the present enzyme is superior to an antisense reagent because the present enzyme provides both target recognition and cleavage, and can function with catalytic turnover, whereas an antisense molecule only provides recognition in a equimolar manner (i.e. non-catalytic), and must rely upon other cellular enzymes for the RNA inactivation reactions.

The following section describes the preparation of improved enzymes based on the "10-23" and the "8-17" motifs described above. These improved enzymes are generic enzymes which can cleave any preselected target sequence, and that target specificity depends solely on the sequence of the substrate binding regions of the enzyme, as described further herein.

As described in Example 5, above, two motifs, designate "10-23" and "8-17", were identified during sequential rounds of selective amplification and recast into an intermolecular cleavage reaction, and shown to perform efficiently in this manner.

Further studies were conducted using a reaction that yielded site-specific catalytic cleavage of the separate substrate molecule shown in FIG. 9 (i.e, intermolecular cleavage) under simulated physiological conditions of 2 mM MgCl2, 150 mM KCl, pH 7.5, 37 C, for a rate of about $k_{cat}$=0.01 $min^{-1}$.

Cleavage occurred following an unpaired purine nucleotide of the substrate that was flanked by oligonucleotides complementary to the enzyme. The 5' and 3' cleavage products bore a 2'(3') phosphate and 5' hydroxyl, respectively, indicative of a reaction mechanism involving attack by a 2-| hydroxyl on an adjacent phosphate. For both the 8-17 and 10-23 motif enzymes, the sequence of the substrate can be changed without loss of catalytic activity, so long as the substrate-binding arms of the enzyme were changed in a complementary manner. The 8-17 enzyme had a special requirement for a rG-dT "wobble" pair located immediately downstream from the cleavage site. Substitution of a Watson-Crick pair at this position eliminated catalytic activity. The substrate-binding arms of the 10-23 enzyme interacted with the substrate entirely through standard Watson-Crick pairing. The catalytic core of the 8-17 and 10-23 motif enzymes, located between the two substrate-binding arms, contained 13 and 15 deoxynucleotides, respectively.

In order to define more precisely the sequence requirements of the catalytic core, a library of $10^{14}$ variants of each motif was generated, introducing random mutations at a frequency of 25% per nucleotide position throughout the core. Each library was subjected to six different in vitro selection protocols, involving a total of 52 rounds of selective amplification. The method and stringency of selection were varied in order to conduct a thorough examination of sequences related to the two prototype molecules. Individuals from the selected populations were cloned, sequenced, and tested for catalytic activity. This procedure was carried out as follows.

The re-selections based on the 8-17 and 10-23 molecules involved six different lineages for each motif. Each lineage entailed 5-21 rounds of in vitro selection, differing with respect to the selection protocol and reaction times. All cleavage reactions were carried out in 2 mM MgCl2, 150 mM NaCl, and 50 mM Tris*HCl (pH 7.5) at 37 C. Reaction times varied from 60 min in early rounds to 1 min in later rounds. Each starting pool of templates was based on a sequence complementary to the prototype, with fixed binding arms of seven nucleotides each and a catalytic core randomized to 25% degeneracy at each nucleotide position. For the 8-17 and 10-23 motifs, the templates had the sequence 5'-gtgccaagct-taccgagtaactTCG-TCCGGCTCGGRagatgggtcgtctgtc-cttccATCT CTAGTTACTTTTTC-3' (SEQ ID NO 124) and 5'-gttgccaagcttaccg-ggaaaaaTCGTTGTAGCTAGCCtaac-taggtcgtctgtccttccA TCTCTAGT TACTTTTTC-3' (SEQ ID NO 125), respectively (PCR primer sites in lower case; substrate-binding arms underlined; randomized positions italicized). The primer used in the template-directed extensions had the sequence 5'-biotin-r(GGAAAAA-GUAACUA-GAGAUGG)d(AAGAGATGGCGAC)-3' (SEQ ID NO 132). The PCR primers for the 8-17-based selections were 5'-GT-GCCAAGCTTACCGAGTAACT-3' (SEQ ID NO 147) and 5'-d(GGAAGGACAGACGACC-CATC)rU (SEQ ID NO 148) and for the 10-23-based selections were 5'-GTGC-CAAGCTTACCGGGAAAAA-3' (SEQ ID NO 127) and 5'-d (GGAAGGACAGACGACCTAGTT)rA (SEQ ID NO 149). The PCR primers encompassed the binding arms, thus fixing these sequences. One of the PCR primers in each set contained a 3'-terminal ribonucleotide, allowing isolation of the template strand from the double-stranded PCR products by alkaline hydrolysis of the non-template strand and subsequent purification by polyacrylamide gel electrophoresis. A gel-based selection scheme was employed in some of the lineages. In those cases, the PCR primers were 5'-biotin-GTGCCAAGCTTACCG-3' (SEQ ID NO 10) and 5'-GAAAAAGTAACTAG-AGATGGAAGGACAGAC-GACC-3' (SEQ ID NO 129) and the extension reactions were carried out on the solid support using the primer 5'-r (GGAAAAAGUAACUAGAGAUGGAAG)-3' (SEQ ID NO 135). A trace amount of [a-32P]-dATP was included in the mixture to label the extension products, which were eluted with alkali, purified by denaturing polyacrylamide gel purification, and recovered by electroelution. The molecules then were reacted and those that underwent cleavage were isolated by gel electrophoresis.

Following the eighth and tenth rounds of the initial selection, individual molecules were cloned and sequenced, as described above. The 17th clone from round eight (8-17) and 23rd clone from round ten (10-23) had the sequence 5'-cacg-gttcga-atggcGTTATGCATCACAC-TATTTTTCATTGAAGCAGGCCGAGCCTT CCACCT-TCcagcggtag-agaagg-3' (SEQ ID NO 130) and 5'-cacggttcgaatggcATGTTAAGT-TCGTCCCTTTTTAGCAACATCGATCGGATT-GGTTTCC Ccagcggtagagaagg-3', (SEQ ID NO 131) respectively (primer sites in lower case; substrate-binding arms underlined). For the intermolecular reaction, synthetic oligodeoxynucleotides were prepared based on the cloned sequences but lacking the regions outside of the substrate-binding arms. These were used to cleave an all-RNA substrate having the same sequence as the primer used to construct the initial library (see above). Subsequently, the substrate-binding arms of the DNA enzyme were reduced to seven nucleotides each and made perfectly complementary to the RNA substrate.

In the case of the 8-17 enzyme, sequence variation among the cloned individuals suggested that the catalytic core consisted of a short internal stem-loop followed by an unpaired region of 4-5 nucleotides (FIG. 10). The stem always contained three base-pairs, at least two of which were G-C. The loop was invariant, having the sequence 5'-AGC-3'. Synthetic constructs in which the stem was lengthened or the sequence of the loop was altered did not exhibit catalytic activity. The unpaired region, connecting the 3' half of the stem to the downstream substrate-binding domain, had the sequence 5'-WCGR-3' or 5'-WCGAA-3'(W=A or T; R=A or G). Variants having the sequence 5'-TCGAA-3' in this region exhibited the highest level of catalytic activity, but this enhancement relative to the 8-17 enzyme was not generalizable to other substrate sequences.

The eighth nucleotide position of the catalytic core of the 10-23 enzyme motif allows variation as either T, C, or A, although a T at this position (as in the prototype) provided the highest level of activity. A survey of numerous different combinations of RNA substrate and corresponding complementary DNA enzyme in the substrate binding region revealed that the 10-23 motif was generalizable with respect to any substrate sequence.

Catalytic activities for the 10-23 and 8-17 motif variants were then measured using multiple-turnover reactions, typically exhibiting <20% variation for identical experiments performed on different days. Kinetic values obtained in single- and multiple-turnover experiments were similar; values obtained with synthetic RNA substrates were slightly less favorable than those obtained with in vitro transcribed substrates. Reported kcat and Km values were determined from the y-intercept and negative slope, respectively, of the best-fit line to a modified Eadie-Hofstee plot of kobs vs. kobs/[S]. Each plot consisted of ten data points for a range of [S] that spanned Km, with [S] in a 10-fold excess over [E]. kobs values were typically based on five data points obtained over the first 10% of the reaction. Substrate and enzyme molecules were preincubated separately for 10 min in reaction buffer, then combined to initiate the reaction. All reactions were carried out in the presence of 0.01% sodium dodecyl sulfate to prevent adherence of material to the vessel walls. The pH was maintained by addition of 50 mM 4-(2-hydroxyethyl)-piperazine-1-propanesulfonic acid. Kinetic values did not depend on the identity of the buffer. Reaction products were separated by electrophoresis in a denaturing 20% polyacrylamide gel and quantitated using a phosphorimager.

Cleavage occurred on the 3' side of a single unpaired nucleotide, preferably a purine, that was followed by a pyrimidine. Target sites surrounded by A and U were cleaved most efficiently, with a catalytic rate of approximately 0.1 min−1 under simulated physiological conditions.

A DNA enzyme that cleaves RNA at an A*U site can be used to target any mRNA start codon (A*UG). As a test case, both synthetic and in vitro transcribed versions of a 17mer RNA corresponding to the translation initiation region of HIV-1 gag/pol mRNA (5'-GGAGAGAGA*UGGGUGCG-3') were prepared. Both versions of the substrate were cleaved at the expected position by the corresponding 10-23 DNA enzyme, in a reaction that proceeded with a kcat of 0.15 min−1 and Km of 0.47 nM under simulated physiological conditions (catalytic efficiency, kcat/Km=3.2×10$^8$ M−1 min−1) (FIG. 11). The catalytic rate increased with increasing $MgCl_2$ concentration range of 1-250 mM, with an apparent Km for $Mg^{2+}$ of 180 mM at pH 7.5 and 37°C. The catalytic rate increased in a roughly log-linear fashion with increasing pH over the range 7.0-8.5 consistent with a reaction mechanism involving deprotonation of the 2'-hydroxyl that lies adjacent to the cleaved phosphoester. In the presence of 50 mM $MgCl_2$ at pH 8.0 and 37°C, conditions that are useful in the laboratory manipulation of RNA, kcat was 3.4 min−1 and Km was 0.76 nM. The catalytic efficiency of the 10-23 DNA enzyme, under both physiological and laboratory conditions, compares favorably with that of known RNA-cleaving RNA enzymes. Compared to the protein enzyme ribonuclease A, the DNA enzyme has ~10$^4$-fold lower kcat but ~10$^5$-fold more favorable Km.

The 10-23 enzyme can be used to cleave a variety of biologically relevant RNAs. We prepared synthetic RNA substrates corresponding to 15-17 nucleotides surrounding the translation initiation site of HIV-1 gag/pol, env, vpr, tat, nef IGF-R and E100 ligase mRNA. Each was cleaved at the expected position by a synthetic DNA enzyme that contained the 10-23 catalytic core flanked by substrate-binding arms of 7 to 12 nucleotides each (Table 4). In all cases the catalytic rate was about 0.1 min−1 under simulated physiological conditions. The value for Km, however, varied with the nucleotide composition of the substrate. For the guanosine-rich gag/pol substrate, Km was <1 nM when either the 7- or 8-nucleotide substrate-binding arms were employed. The env and vpr substrates were cleaved with a much less favorable Km when the 7-nucleotide binding arms were used, but Km improved substantially when the arms were increased to 8 nucleotides each.

TABLE 4

DNA-catalyzed cleavage of various RNA substrates under simulated physiological conditions

| Gene | SEQ ID NO | Target Sequence | Arm length | kcat (min-1) | Km (nM) |
|---|---|---|---|---|---|
| HIV-1 | | | | | |
| gag | 102 | GGAGAGAGA*UGGGUGCG | 8 + 8 | 0.1 | 0.7 |
| gag | 103 | GAGAGAGA*UGGGUGC | 7 + 7 | 0.1 | 0.9 |
| env | 104 | CAGUGGCAA*UGAGAGUG | 8 + 8 | 0.04 | 9 |
| env | 105 | AGUGGCAA*UGAGAGU | 7 + 7 | 0.03 | 900 |
| vpr | 106 | GAGGAUAGA*UGGAACAA | 8 + 8 | 0.1 | 20 |
| vpr | 107 | AGGAUAGA*UGGAACA | 7 + 7 | 0.08 | 500 |
| tat | 108 | GCAAGAAA*UGGAGCC | 7 + 7 | 0.04 | 300 |
| nef | 109 | CUAUAAGA*UGGGUGA | 7 + 7 | 0.05 | 900 |
| FIV | | | | | |
| gag | 110 | UACAGCAACA*UGGGGAAUGG | 9 + 10 | 0.005 | 8 |
| gag | 111 | CAUGGGGAA*UGGACAGGG | 8 + 9 | 0.006 | 5 |
| IGF-R | | | | | |
| | 112 | CAAAUAAAAGGGA*UGAAGUCUGG | 12 + 10 | 0.02 | 20 |
| | 113 | AAGGAAUGAAG*UCUGGCUCCG | 10 + 10 | 0.3 | 50 |
| | 114 | AUACCGCAAAG*UCUUUGAGAAUU | 10 + 12 | 0.1 | 30 |
| | 115 | AAGUCUUUGAGAG*UUUCCUGCAC | 12 + 10 | 0.05 | 21 |
| | 116 | AACACCACCA*UGUCCAGCC | 9 + 9 | 0.06 | 2 |
| | 117 | GGCCUUUCACA*UUGUACCGC | 10 + 9 | 0.1 | 10 |
| | 118 | UUGUACCGCA*UCGAUAUCCAC | 9 + 11 | 0.06 | 1 |
| E100 ligase | | | | | |
| | 119 | GAACAUUACAUUA*UAGUGACCAG | 12 + 10 | 1.0 | 80 |

Kinetic values measured and shown in Table 4 were obtained under multiple-turnover conditions, with synthetic RNA substrate in >10-fold excess over synthetic DNA enzyme, using the reaction conditions: 2 mM MgCl2, 150 mM NaCl, pH 7.5, 37 C, obtained at 25 mM MgCl2.

As a further demonstration of the variation to the substrate binding region (arms) that a DNA enzyme of the present invention can support, the length of the arms was systematically varied from 4 to 13 nucleotide residues using the HIV-1 gag gene start codon target nucleotide sequence shown in Table 4. The reaction was run separately for each DNA enzyme construct prepared as described above except that the arm length was varied as shown in FIG. 13. The kinetic properties of the catalytic DNA enzyme was measured as before under the conditions of 2 mM Mg+2, 150 mM NaCl, pH 7.5, 37 C and measuring multiple turnover of enzyme. Both $k_{cat}$ (min$^{-1}$) and $K_m$ (nM) was measured, and is shown in FIG. 13 using the 10-23 motif modified for complementary binding to the HIV-1 gag gene.

The results show that useful catalytic rates are observed over the full range of from 5 to 13 nucleotides per arm per substrate binding region, with a preferred range of from 7 to 10 nucleotides being particularly efficient. The results also show that the effective concentration of enzyme for half maximal catalysis ($K_m$) is in the range of 1000 to 0.05 nanomolar (nM) for arms of a 5 to 13 nucleotide length, with lengths of 7 to 13 particularly preferred.

A variety of modifications were incorporated into the 10-23 DNA enzyme and tested for stability in 10% fetal bovine serum (FIG. 13). These modifications included: 1) an "inverted" (3',3'-linked) thymidylate at the 3' end of the DNA; 2) five 2'-O-methyl residues at the distal end of both substrate-binding arms; 3) 2'-O-methyl residues at all positions in both substrate-binding arms; 4) phosphorothioate residues at the five pyrimidine-pyrimidine sites within the catalytic core; 5) three phosphorothioate residues at the distal end of both substrate-binding arms. The best protection was afforded by the inverted thymidylate (t1/2>60 min). All of the other modifications resulted in enhanced serum stability compared to the unmodified DNA, with the exception of the five P=S substitutions in the core. All of the modified DNA enzymes retained catalytic activity.

Thus, the invention describes a catalytic DNA molecule having site-specific endonuclease activity which can be designed to cleave any preselected substrate nucleic acid sequence. The DNA molecule (enzyme) has first and second substrate binding regions (arms) flanking a core region, and each arm has a sequence complementary to a portion of the target substrate nucleic acid sequence, such that together, the first and second arms define the substrate nucleic acid sequence to be cleaved. By complementary is meant that the substrate binding regions bind to the target sequence using conventional Watson-Crick base pairing.

The arms can be any of a variety of lengths. However, because it is seen that the length affects the catalytic rate ($k_{cat}$) and effective concentration ($K_m$) of the enzyme (see FIG. 12), the preferred arm lengths are from 5 to 13 nucleotides of complementarity each, preferably about 6 to 11 nucleotides, and more preferably about 7 to 10 nucleotides in length.

The core region can have a variety of sequences based on the formula:

(I.) T(stem) 'AGC (stem) "Z, wherein said (stem)' and (stem)" are each three sequential nucleotides which when hybridized as a (stem)':(stem)" pair comprise three base pairs including at least two G:C pairs and wherein said Z=WCGR or WCGAA, and W=A or T and R=A or G. This stem structure is shown in FIG. 10 and illustrates three complementary nucleotide pairs. Particularly preferred is the prototype structure of the core region of motif 8-17, "TCCGAGCCGGACGA" (SEQ ID NO 120) shown in FIG. 10.

In another embodiment, the core region can have a sequence according to the formula:

(II.) RGGCTAGCXACAACGA, (SEQ ID NO 122)

wherein said X=T, C or A, and R=A or G. Particularly preferred is the prototype structure of the core region of motif 10-23, "RGGCTAGCTACAACGA" (SEQ ID NO 121) shown in FIG. 10.

A DNA enzyme of the above design can exhibit a range of useful catalytic rates and effective catalytic concentrations depending upon the arm length as noted in FIG. 12. A DNA enzyme of this invention according to the 8-17 or 10-23 motif typically has a catalytic turnover rate ($k_{cat}$) of about 0.005 to 0.1 min$^{-1}$, preferably about 0.01 to 0.1 min$^{-1}$, and more preferably about 0.03 to 0.1 min$^{-1}$, under physiological conditions. A particularly preferred enzyme has a rate of about 0.1 min$^{-1}$. A DNA enzyme of this invention according to the 8-17 or 10-23 motif typically also has a catalytic half maximal effective concentration ($K_m$) of about 0.05 to 1000 nanomolar (nM), preferably about 0.7 to 900 nM, more preferably less than about 1.0 micromolar (uM), and most preferably about 0.1 (uM), under physiological conditions.

The foregoing also demonstrates that a preferred DNA enzyme has nucleotide modifications which stabilize the DNA enzyme for use under physiological conditions. Any of a variety of modifications can be utilized so long as the Enzyme retains its catalytic activity as defined and measured herein, and therefore the invention need not be so limited to a particular stabilitation modification. Preferred modifications render a subject DNA molecule less susceptible to exo or endo nucleolytic digestion. In one embodiment the modification comprises incorporation of one or more nucleoside phosphorothioate residues, such as is described by Zhang et al, *Biochem. Pharmacol.*, 50:545-556 (1995) or by Stein, C. A., *Trends Biotechnol.*, 14:147-149 (1996). The phosphorothioate residue can be in the arms or in the core, and in one embodiment can comprise a residue on a dipyrimidine within the core. Another modification comprises the substitution of an O-methyl group onto the 2' position of the ribose or deoxyribose component of the sugar nucleotide, to form a 2'O-methyl ribonucleotide, as well known and described by Zhang et al., above. An additional modification is to attach an inverted terminal nucleotide onto the 3' end of the DNA molecule, such that the 3' end is blocked, appearing as a free 5' end. This structure blocks 3'endonucleases, and is produced by forming a 3'-3' linked nucleotide at the 3' end (i.e, an inverted nucleotide). The preparation of a 3' inverted nucleotide at the 3' end is well known, and is prepared using a modified solid support in oligonucleotide synthesis having the terminal 3' residue inverted as a starting material. A preferred solid support material for this purpose is dT-5'-CPG 500, available from Glen Research (Sterling, Va.) and is a modified controlled pore glass resin having the modified residue.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A catalytic DNA molecule having site-specific endonuclease activity specific for a nucleotide sequence defining a cleavage site in a preselected substrate nucleic acid sequence,
  said molecule having first and second substrate binding regions flanking a core region,
  wherein said first substrate binding region has a sequence complementary to a first portion of said preselected substrate nucleic acid sequence,
  said second substrate binding region has a sequence complementary to a second portion of said preselected substrate nucleic acid sequence, and
  said core region having a sequence according to the formula:

(I.) T(stem)'AGC(stem)"Z, wherein said (stem)' and (stem)" are each three sequential nucleotides which when hybridized as a (stem)':(stem)" pair comprise three base pairs including at least two G:C pairs and wherein said Z=WCGR or WCGAA, and W=A or T and R=A or G.

2. An isolated catalytic DNA molecule having sequence-specific endonuclease activity, wherein said molecule comprises a conserved core, wherein said conserved core comprises the sequence CCGAGCCGGACGA (SEQ ID NO:151), or wherein said conserved core comprises the sequence CCGAGCCGGACGA (SEQ ID NO:151) having one to three residues substituted by G, A, T, or C.

3. The catalytic DNA molecule of claim 2, wherein said molecule further comprises first and second substrate binding regions flanking the conserved core.

4. The catalytic DNA molecule of claim 3, wherein said first and second substrate binding regions are from 5 to 13 nucleotides in length.

5. The catalytic DNA molecule of claim 2 comprising a deoxyribonucleotide, a modified DNA, a nucleotide analog, or any combination thereof.

6. The catalytic DNA molecule of claim 2, wherein the molecule consists of deoxyribonucleotides.

7. The catalytic DNA molecule of claim 2, wherein the conserved core consists of deoxyribonucleotides.

8. The catalytic DNA molecule of claim 2 comprising a 5' terminus and a 3' terminus, wherein said 5' terminus or said 3' terminus is modified with an exonuclease-resistant nucleotide or wherein both said 5' terminus and said 3' terminus are modified with an exonuclease-resistant nucleotide.

9. The catalytic DNA molecule of claim 2 comprising one or more phosphorothioate nucleotides.

10. The catalytic DNA molecule of claim 2 comprising a 3' terminus comprising an inverted nucleotide.

11. The catalytic DNA molecule of claim 2, wherein said molecule has a $k_{cat}$ of about 0.005 to 0.1 min$^{-1}$.

12. An isolated catalytic nucleic acid molecule having sequence-specific endonuclease activity, said molecule comprising first and second substrate binding regions flanking a conserved core, wherein said conserved core comprises the sequence CCGAGCCGGACGA (SEQ ID NO:151), or wherein said conserved core comprises CCGAGCCGGACGA (SEQ ID NO:151) having one to three residues substituted by G, A, T, C.

13. The catalytic nucleic acid molecule of claim 12, wherein said first and second substrate binding regions are from 5 to 13 nucleotides in length.

14. The catalytic nucleic acid molecule of claim 12 comprising a deoxyribonucleotide, a modified DNA, a nucleotide analog, or any combination thereof.

15. The catalytic nucleic acid molecule of claim 12, wherein the molecule consists of deoxyribonucleotides.

16. The catalytic DNA molecule of claim 12, wherein the conserved core consists of deoxyribonucleotides.

17. The catalytic nucleic acid molecule of claim 12 comprising a 5' terminus and a 3' terminus, wherein said 5' terminus or said 3' terminus is modified with an exonuclease-resistant nucleotide or wherein both said 5' terminus and said 3' terminus are modified with an exonuclease-resistant nucleotide.

18. The catalytic nucleic acid molecule of claim 12 comprising one or more phosphorothioate nucleotides.

19. The catalytic nucleic acid molecule of claim 12 comprising a 3' terminus comprising an inverted nucleotide.

20. The catalytic nucleic acid molecule of claim 12, wherein said molecule has a $k_{cat}$ of about 0.005 to 0.1 min$^{-1}$.

21. The catalytic nucleic acid molecule of claim 12 comprising a 2' O-methyl ribonucleotide.

22. The catalytic nucleic acid molecule of claim 12 comprising one or more ribonucleotides.

23. The catalytic nucleic acid molecule of claim 12, wherein the conserved core comprises a deoxyribonucleotide, a modified DNA, a nucleotide analog, or any combination thereof.

24. The catalytic nucleic acid molecule of claim 12, wherein said conserved core comprises the sequence CCGAGCCGGACGA (SEQ ID NO:151).

25. The catalytic nucleic acid molecule of claim 12, having one residue substituted by G, A, T, C, or U.

26. The catalytic nucleic acid molecule of claim 12, having two residues substituted by G, A, T, C, or U.

27. The catalytic nucleic acid molecule of claim 12, having three residues substituted by G, A, T, C, or U.

28. A method of sequence-specifically cleaving a substrate nucleic acid molecule, comprising:
  a) admixing the substrate nucleic acid molecule with a catalytic DNA molecule of claim 1 that hybridizes with the substrate nucleic acid molecule at a sequence-specific cleavage site, to form an admixture; and
  b) maintaining said admixture under reaction conditions sufficient to allow said catalytic DNA molecule to sequence-specifically cleave said substrate nucleic acid molecule.

29. The method of claim 28, wherein said catalytic DNA molecule comprises first and second substrate binding regions flanking a conserved core.

30. The method of claim 29, wherein said conserved core comprises the sequence CCGAGCCGGACGA (SEQ ID NO:151), or wherein said conserved core comprises CCGAGCCGGACGA (SEQ ID NO:151) having one to three residues substituted by G, A, T, C, or U.

31. The method of claim 28, wherein said catalytic DNA molecule comprises a deoxyribonucleotide, a modified DNA, a nucleotide analog, or any combination thereof.

32. The method of claim 28, wherein the molecule consists of deoxyribonucleotides.

33. A method of sequence-specifically cleaving a substrate nucleic acid molecule, comprising:
- c) admixing the substrate nucleic acid molecule with the catalytic nucleic acid molecule of claim 12, wherein said catalytic nucleic acid molecule site-specifically hybridizes with said substrate nucleic acid molecule at a sequence-specific cleavage site, to form an admixture; and
- d) maintaining said admixture under reaction conditions sufficient to allow said catalytic nucleic acid molecule to sequence-specifically cleave said substrate nucleic acid molecule.

34. The method of claim 33, wherein said first and second substrate binding regions are from 5 to 13 nucleotides in length.

35. The method of claim 33, wherein said conserved core comprises the sequence CCGAGCCGGACGA (SEQ ID NO:151).

36. The method of claim 33, wherein said catalytic nucleic acid molecule comprises a deoxyribonucleotide, a modified DNA, a nucleotide analog, or any combination thereof.

37. The method of claim 33, wherein the molecule comprises one or more ribonucleotides.

38. The method of claim 33, wherein said conserved core consists of deoxyribonucleotides.

* * * * *

UNITED STATES PATENT AND TRADEMARK OFFICE
CERTIFICATE OF CORRECTION

| | |
|---|---|
| PATENT NO. | : 7,807,817 B2 |
| APPLICATION NO. | : 11/605177 |
| DATED | : October 5, 2010 |
| INVENTOR(S) | : Gerald F. Joyce and Ronald R. Breaker |

It is certified that error appears in the above-identified patent and that said Letters Patent is hereby corrected as shown below:

At column 1, line 20, add the following paragraph:

STATEMENT OF GOVERNMENT SUPPORT

-- This invention was made with government support under Contract No. AI030882 awarded by the National Institutes of Health. The government has certain rights in the invention. --

Signed and Sealed this
Seventh Day of June, 2011

David J. Kappos
*Director of the United States Patent and Trademark Office*

SEQUENCE LISTING

<160> NUMBER OF SEQ ID NOS: 155

<210> SEQ ID NO 1
<211> LENGTH: 15
<212> TYPE: DNA
<213> ORGANISM: Artificial Sequence
<220> FEATURE:
<223> OTHER INFORMATION: Synthesized

<400> SEQUENCE: 1
cggtaagctt ggcac                                                15

<210> SEQ ID NO 2
<211> LENGTH: 19
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: 8
<223> OTHER INFORMATION: N = Adenosine Ribonucleotide

<400> SEQUENCE: 2
tcactatngg aagagatgg                                            19

<210> SEQ ID NO 3
<211> LENGTH: 38

```
<212> TYPE: DNA
<213> ORGANISM: Artificial Sequence
<220> FEATURE:
<223> OTHER INFORMATION: Synthesized

<400> SEQUENCE: 3
acacatctct gaagtagcgc cgccgtatag tgacgcta                              38

<210> SEQ ID NO 4
<211> LENGTH: 80
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (16)...(65)
<223> OTHER INFORMATION: n = a, g, t, or c

<400> SEQUENCE: 4
gtgccaagct taccgnnnnn nnnnnnnnnn nnnnnnnnnn nnnnnnnnnn nnnnnnnnnn      60
nnnnngtcgc catctcttcc                                                 80

<210> SEQ ID NO 5
<211> LENGTH: 28
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: 28
<223> OTHER INFORMATION: N = Adenosine Ribonucleotide
<220> FEATURE:
<221> NAME/KEY: misc_feature
<222> LOCATION: 28
<223> OTHER INFORMATION: 2' 3' cyclic phosphate

<400> SEQUENCE: 5
gggacgaatt ctaatacgac tcactatn                                        28

<210> SEQ ID NO 6
<211> LENGTH: 28
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: 28
<223> OTHER INFORMATION: N = Adenosine Ribonucleotide
<220> FEATURE:
<221> NAME/KEY: misc_feature
<222> LOCATION: 1
<223> OTHER INFORMATION: Optional 5 prime biotinylation

<400> SEQUENCE: 6
gggacgaatt ctaatacgac tcactatn                                        28

<210> SEQ ID NO 7
<211> LENGTH: 19
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: 8
<223> OTHER INFORMATION: N = Adenosine Ribonucleotide
```

-continued

```
<400> SEQUENCE: 7
tcactatngg aagagatgg                                                    19

<210> SEQ ID NO 8
<211> LENGTH: 8
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: 8
<223> OTHER INFORMATION: N = Adenosine Ribonucleotide

<400> SEQUENCE: 8 tcactatn                                                                 8

<210> SEQ ID NO 9
<211> LENGTH: 30
<212> TYPE: DNA
<213> ORGANISM: Artificial Sequence
<220> FEATURE:
<223> OTHER INFORMATION: Synthesized

<400> SEQUENCE: 9
ccatctcttc ctatagtgag tccggctgca                                        30

<210> SEQ ID NO 10
<211> LENGTH: 15
<212> TYPE: DNA
<213> ORGANISM: Artificial Sequence
<220> FEATURE:
<223> OTHER INFORMATION: Synthesized

<400> SEQUENCE: 10
gtgccaagct taccg                                                        15

<210> SEQ ID NO 11
<211> LENGTH: 43
<212> TYPE: DNA
<213> ORGANISM: Artificial Sequence
<220> FEATURE:
<223> OTHER INFORMATION: Synthesized

<400> SEQUENCE: 11
ctgcagaatt ctaatacgac tcactatagg aagagatggc gac                         43

<210> SEQ ID NO 12
<211> LENGTH: 19
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: 8
<223> OTHER INFORMATION: N = Adenosine Ribonucleotide

<400> SEQUENCE: 12
tcactatngg aagagatgg                                                    19

<210> SEQ ID NO 13
<211> LENGTH: 43
<212> TYPE: DNA
<213> ORGANISM: Artificial Sequence
<220> FEATURE:
<223> OTHER INFORMATION: Synthesized
```

```
<220> FEATURE:
<221> NAME/KEY: misc_feature
<222> LOCATION: 28
<223> OTHER INFORMATION: N = Adenosine Ribonucleotide

<400> SEQUENCE: 13
gggacgaatt ctaatacgac tcactatngg aagagatggc gac                    43

<210> SEQ ID NO 14
<211> LENGTH: 50
<212> TYPE: DNA
<213> ORGANISM: Artificial Sequence
<220> FEATURE:
<223> OTHER INFORMATION: Synthesized

<400> SEQUENCE: 14
tcacacatct ctgaagtagc gccgccgtat gtgacgctag gggttcgcct             50

<210> SEQ ID NO 15
<211> LENGTH: 50
<212> TYPE: DNA
<213> ORGANISM: Artificial Sequence
<220> FEATURE:
<223> OTHER INFORMATION: Synthesized

<400> SEQUENCE: 15 gggggggaacg ccgtaacaag ctctgaacta gcggttgcga tatagtcgta            50

<210> SEQ ID NO 16
<211> LENGTH: 50
<212> TYPE: DNA
<213> ORGANISM: Artificial Sequence
<220> FEATURE:
<223> OTHER INFORMATION: Synthesized

<400> SEQUENCE: 16
cgggactccg tagcccattg cttttttgcag cgtcaacgaa tagcgtatta            50

<210> SEQ ID NO 17
<211> LENGTH: 50
<212> TYPE: DNA
<213> ORGANISM: Artificial Sequence
<220> FEATURE:
<223> OTHER INFORMATION: Synthesized

<400> SEQUENCE: 17
ccaccatgtc ttctcgagcc gaaccgatag ttacgtcata cctcccgtat             50

<210> SEQ ID NO 18
<211> LENGTH: 50
<212> TYPE: DNA
<213> ORGANISM: Artificial Sequence
<220> FEATURE:
<223> OTHER INFORMATION: Synthesized

<400> SEQUENCE: 18
gccagattgc tgctaccagc ggtacgaaat agtgaagtgt tcgtgactat             50

<210> SEQ ID NO 19
<211> LENGTH: 50
<212> TYPE: DNA
<213> ORGANISM: Artificial Sequence
<220> FEATURE:
<223> OTHER INFORMATION: Synthesized

<400> SEQUENCE: 19
```
ataggccatg ctttggctag cggcaccgta tagtgtacct gcccttatcg                50

<210> SEQ ID NO 20
<211> LENGTH: 50
<212> TYPE: DNA
<213> ORGANISM: Artificial Sequence
<220> FEATURE:
<223> OTHER INFORMATION: Synthesized

<400> SEQUENCE: 20
tctgctctcc tctattctag cagtgcagcg aaatatgtcg aatagtcggt                50

<210> SEQ ID NO 21
<211> LENGTH: 50
<212> TYPE: DNA
<213> ORGANISM: Artificial Sequence
<220> FEATURE:
<223> OTHER INFORMATION: Synthesized

<400> SEQUENCE: 21
ttgcccagca tagtcggcag acgtggtgtt agcgacacga taggcccggt                50

<210> SEQ ID NO 22
<211> LENGTH: 50
<212> TYPE: DNA
<213> ORGANISM: Artificial Sequence
<220> FEATURE:
<223> OTHER INFORMATION: Synthesized

<400> SEQUENCE: 22
ttgctagctc ggctgaactt ctgtagcgca accgaaatag tgaggcttga                50

<210> SEQ ID NO 23
<211> LENGTH: 107
<212> TYPE: DNA
<213> ORGANISM: Artificial Sequence
<220> FEATURE:
<223> OTHER INFORMATION: Synthesized
<220> FEATURE:
<221> NAME/KEY: misc_difference
<222> LOCATION: 28
<223> OTHER INFORMATION: N = Adenosine Ribonucleotide
<220> FEATURE:
<221> NAME/KEY: misc_feature
<222> LOCATION: (49)...(88)
<223> OTHER INFORMATION: N = A, G, C, or T

<400> SEQUENCE: 23
gggacgaatt ctaatacgac tcactatngg aagagatggc gacatctcnn nnnnnnnnn     60 nnnnnnnnnn nnnnnnnnnn nnnnnnnngt gacggtaagc ttggcac                  107

<210> SEQ ID NO 24
<211> LENGTH: 49
<212> TYPE: DNA
<213> ORGANISM: Artificial Sequence
<220> FEATURE:
<223> OTHER INFORMATION: Synthesized

<400> SEQUENCE: 24
ccgcccacct cttttacgag cctgtacgaa atagtgctct tgttagtat                 49

<210> SEQ ID NO 25
<211> LENGTH: 48
<212> TYPE: DNA
<213> ORGANISM: Artificial Sequence
<220> FEATURE:
<223> OTHER INFORMATION: Synthesized

<400> SEQUENCE: 25
tctcttcagc gatgcacgct tgttttaatg ttgcacccat gttagtga    48

<210> SEQ ID NO 26
<211> LENGTH: 46
<212> TYPE: DNA
<213> ORGANISM: Artificial Sequence
<220> FEATURE:
<223> OTHER INFORMATION: Synthesized

<400> SEQUENCE: 26
tctcatcagc gattgaacca cttggtggac agacccatgt tagtga    46

<210> SEQ ID NO 27
<211> LENGTH: 49
<212> TYPE: DNA
<213> ORGANISM: Artificial Sequence
<220> FEATURE:
<223> OTHER INFORMATION: Synthesized

<400> SEQUENCE: 27
ccgcccacct cttttacgag cctgtacgaa atagtgttct tgttagtat    49

<210> SEQ ID NO 28
<211> LENGTH: 49
<212> TYPE: DNA
<213> ORGANISM: Artificial Sequence
<220> FEATURE:
<223> OTHER INFORMATION: Synthesized

<400> SEQUENCE: 28
ccgcccacct cttttacgag cctgtacgaa atagtgctct cgttagtat    49

<210> SEQ ID NO 29
<211> LENGTH: 48
<212> TYPE: DNA
<213> ORGANISM: Artificial Sequence
<220> FEATURE:
<223> OTHER INFORMATION: Synthesized

<400> SEQUENCE: 29
tctcagactt agtccatcac actctgtgca tatgcctgct tgatgtga    48

<210> SEQ ID NO 30
<211> LENGTH: 42
<212> TYPE: DNA
<213> ORGANISM: Artificial Sequence
<220> FEATURE:
<223> OTHER INFORMATION: Synthesized

<400> SEQUENCE: 30
ctctcatctg ctagcacgct cgaatagtgt cagtcgatgt ga    42

<210> SEQ ID NO 31
<211> LENGTH: 40
<212> TYPE: DNA
<213> ORGANISM: Artificial Sequence
<220> FEATURE:
<223> OTHER INFORMATION: Synthesized

<400> SEQUENCE: 31
tacagcgatt cacccttgtt taagggttac acccatgtta    40

<210> SEQ ID NO 32

```
<211> LENGTH: 40
<212> TYPE: DNA
<213> ORGANISM: Artificial Sequence
<220> FEATURE:
<223> OTHER INFORMATION: Synthesized

<400> SEQUENCE: 32
atcagcgatt aacgcttgtt tcaatgttac acccatgtta                            40

<210> SEQ ID NO 33
<211> LENGTH: 40
<212> TYPE: DNA
<213> ORGANISM: Artificial Sequence
<220> FEATURE:
<223> OTHER INFORMATION: Synthesized

<400> SEQUENCE: 33
ttcagcgatt aacgcttatt ttagcgttac acccatgtta                            40

<210> SEQ ID NO 34
<211> LENGTH: 40
<212> TYPE: DNA
<213> ORGANISM: Artificial Sequence
<220> FEATURE:
<223> OTHER INFORMATION: Synthesized

<400> SEQUENCE: 34
atcagcgatt caccottgtt ttaaggttgc acccatgtta                            40

<210> SEQ ID NO 35
<211> LENGTH: 40
<212> TYPE: DNA
<213> ORGANISM: Artificial Sequence
<220> FEATURE:
<223> OTHER INFORMATION: Synthesized

<400> SEQUENCE: 35
atcagcgatt caccottgtt taagcgttac acccatgttg                            40

<210> SEQ ID NO 36
<211> LENGTH: 40
<212> TYPE: DNA
<213> ORGANISM: Artificial Sequence
<220> FEATURE:
<223> OTHER INFORMATION: Synthesized

<400> SEQUENCE: 36
atcagcgatt caccottgtt ttaaggttac acccatgtta                            40

<210> SEQ ID NO 37
<211> LENGTH: 40
<212> TYPE: DNA
<213> ORGANISM: Artificial Sequence
<220> FEATURE:
<223> OTHER INFORMATION: Synthesized

<400> SEQUENCE: 37
atcagcgatt aacgcttatt ttagcgttac acccatgtta                            40

<210> SEQ ID NO 38
<211> LENGTH: 40
<212> TYPE: DNA
<213> ORGANISM: Artificial Sequence
<220> FEATURE:
<223> OTHER INFORMATION: Synthesized

<400> SEQUENCE: 38
```

```
atcagcgatt aacgcttgtt ttagtgttgc acccatgtta                    40

<210> SEQ ID NO 39
<211> LENGTH: 40
<212> TYPE: DNA
<213> ORGANISM: Artificial Sequence
<220> FEATURE:
<223> OTHER INFORMATION: Synthesized

<400> SEQUENCE: 39
atcagcgatt aacgcttatt ttagcattac acccatgtta                    40

<210> SEQ ID NO 40
<211> LENGTH: 10
<212> TYPE: DNA
<213> ORGANISM: Artificial Sequence
<220> FEATURE:
<223> OTHER INFORMATION: Synthesized

<400> SEQUENCE: 40
gccatgcttt                                                     10

<210> SEQ ID NO 41
<211> LENGTH: 10
<212> TYPE: DNA
<213> ORGANISM: Artificial Sequence
<220> FEATURE:
<223> OTHER INFORMATION: Synthesized

<400> SEQUENCE: 41
ctctatttct                                                     10

<210> SEQ ID NO 42
<211> LENGTH: 12
<212> TYPE: DNA
<213> ORGANISM: Artificial Sequence
<220> FEATURE:
<223> OTHER INFORMATION: Synthesized

<400> SEQUENCE: 42
tatgtgacgc ta                                                  12

<210> SEQ ID NO 43
<211> LENGTH: 10
<212> TYPE: DNA
<213> ORGANISM: Artificial Sequence
<220> FEATURE:
<223> OTHER INFORMATION: Synthesized

<400> SEQUENCE: 43
tatagtcgta                                                     10

<210> SEQ ID NO 44
<211> LENGTH: 11
<212> TYPE: DNA
<213> ORGANISM: Artificial Sequence
<220> FEATURE:
<223> OTHER INFORMATION: Synthesized

<400> SEQUENCE: 44
atagcgtatt a                                                   11

<210> SEQ ID NO 45
<211> LENGTH: 13
<212> TYPE: DNA
```

```
<213> ORGANISM: Artificial Sequence
<220> FEATURE:
<223> OTHER INFORMATION: Synthesized

<400> SEQUENCE: 45
atagttacgt cat                                                    13

<210> SEQ ID NO 46
<211> LENGTH: 14
<212> TYPE: DNA
<213> ORGANISM: Artificial Sequence
<220> FEATURE:
<223> OTHER INFORMATION: Synthesized

<400> SEQUENCE: 46
aatagtgaag tgtt                                                   14

<210> SEQ ID NO 47
<211> LENGTH: 11
<212> TYPE: DNA
<213> ORGANISM: Artificial Sequence
<220> FEATURE:
<223> OTHER INFORMATION: Synthesized

<400> SEQUENCE: 47
ataggcccgg t                                                      11

<210> SEQ ID NO 48
<211> LENGTH: 14
<212> TYPE: DNA
<213> ORGANISM: Artificial Sequence
<220> FEATURE:
<223> OTHER INFORMATION: Synthesized

<400> SEQUENCE: 48
aatagtgagg cttg                                                   14

<210> SEQ ID NO 49
<211> LENGTH: 12
<212> TYPE: RNA
<213> ORGANISM: Human Immunodeficiency Virus Type I

<400> SEQUENCE: 49
guaacuagag au                                                     12

<210> SEQ ID NO 50
<211> LENGTH: 98
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (7)...(18)
<223> OTHER INFORMATION: Positions 7-18 is RNA; the remainder of the
      sequence is DNA
<220> FEATURE:
<221> NAME/KEY: misc_feature
<222> LOCATION: (34)...(83)
<223> OTHER INFORMATION: N = A, T, G, or C

<400> SEQUENCE: 50
ggaaaaguaa cuagagaugg aagagatggc gacnnnnnnn nnnnnnnnnn nnnnnnnnnn   60
nnnnnnnnnn nnnnnnnnnn nnncggtaag cttggcac                          98

<210> SEQ ID NO 51
```

```
<211> LENGTH: 99
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)...(24)
<223> OTHER INFORMATION: 1-24 is RNA; the remainder of the sequence is
      DNA
<220> FEATURE:
<221> NAME/KEY: misc_feature
<222> LOCATION: (35)...(84)
<223> OTHER INFORMATION: N = A, T, G, or C

<400> SEQUENCE: 51
ggaaaaagua acuagagaug gaagagaugg cgacnnnnnn nnnnnnnnnn nnnnnnnnnn      60
nnnnnnnnnn nnnnnnnnnn nnnncggtaa gcttggcac                            99

<210> SEQ ID NO 52
<211> LENGTH: 50
<212> TYPE: DNA
<213> ORGANISM: Artificial Sequence
<220> FEATURE:
<223> OTHER INFORMATION: Synthesized

<400> SEQUENCE: 52
ccaatagtgc tactgtgtat ctcaatgctg gaaacacggg ttatctcccg                50

<210> SEQ ID NO 53
<211> LENGTH: 50
<212> TYPE: DNA
<213> ORGANISM: Artificial Sequence
<220> FEATURE:
<223> OTHER INFORMATION: Synthesized

<400> SEQUENCE: 53
ccaaaacagt ggagcattat atctactcca caaagaccac ttttctcccg                50

<210> SEQ ID NO 54
<211> LENGTH: 50
<212> TYPE: DNA
<213> ORGANISM: Artificial Sequence
<220> FEATURE:
<223> OTHER INFORMATION: Synthesized

<400> SEQUENCE: 54
atccgtacta gcatgcagac agtctgtctg cttttttcatt actcactccc               50

<210> SEQ ID NO 55
<211> LENGTH: 49
<212> TYPE: DNA
<213> ORGANISM: Artificial Sequence
<220> FEATURE:
<223> OTHER INFORMATION: Synthesized

<400> SEQUENCE: 55
caattcatga tgaccaactc tgtcaacacg cgaactttta acactggca                 49

<210> SEQ ID NO 56
<211> LENGTH: 50
<212> TYPE: DNA
<213> ORGANISM: Artificial Sequence
<220> FEATURE:
<223> OTHER INFORMATION: Synthesized

<400> SEQUENCE: 56
```

```
cttccacctt ccgagccgga cgaagttact tttatcaca ctacgtattg          50

<210> SEQ ID NO 57
<211> LENGTH: 50
<212> TYPE: DNA
<213> ORGANISM: Artificial Sequence
<220> FEATURE:
<223> OTHER INFORMATION: Synthesized

<400> SEQUENCE: 57
ggcaagagat ggcatatatt caggtaactg tggagatacc ctgtctgcca          50

<210> SEQ ID NO 58
<211> LENGTH: 50
<212> TYPE: DNA
<213> ORGANISM: Artificial Sequence
<220> FEATURE:
<223> OTHER INFORMATION: Synthesized

<400> SEQUENCE: 58
ctagaccatt cacgtttacc aagctatggt aagaactaga atcacgcgta          50

<210> SEQ ID NO 59
<211> LENGTH: 50
<212> TYPE: DNA
<213> ORGANISM: Artificial Sequence
<220> FEATURE:
<223> OTHER INFORMATION: Synthesized

<400> SEQUENCE: 59
cgtacacgtg gaaaagctat aagtcaagtt ctcatcatgt acctgaccgc          50

<210> SEQ ID NO 60
<211> LENGTH: 50
<212> TYPE: DNA
<213> ORGANISM: Artificial Sequence
<220> FEATURE:
<223> OTHER INFORMATION: Synthesized

<400> SEQUENCE: 60
cagtgataca tgagtgcacc gctacgacta agtctgtaac ttattctacc          50

<210> SEQ ID NO 61
<211> LENGTH: 50
<212> TYPE: DNA
<213> ORGANISM: Artificial Sequence
<220> FEATURE:
<223> OTHER INFORMATION: Synthesized

<400> SEQUENCE: 61
accgaattaa actaccgaat agtgtggttt ctatgcttct tcttccctga          50

<210> SEQ ID NO 62
<211> LENGTH: 50
<212> TYPE: DNA
<213> ORGANISM: Artificial Sequence
<220> FEATURE:
<223> OTHER INFORMATION: Synthesized

<400> SEQUENCE: 62
caggtagata taatgcgtca ccgtgcttac actcgtttta ttagtatgtc          50

<210> SEQ ID NO 63
<211> LENGTH: 49
<212> TYPE: DNA
<213> ORGANISM: Artificial Sequence
```

-continued

<220> FEATURE:
<223> OTHER INFORMATION: Synthesized

<400> SEQUENCE: 63
ccctacaaca ccactgggcc caattagatt aacgctattt tataactcg         49

<210> SEQ ID NO 64
<211> LENGTH: 49
<212> TYPE: DNA
<213> ORGANISM: Artificial Sequence
<220> FEATURE:
<223> OTHER INFORMATION: Synthesized

<400> SEQUENCE: 64
ccaaacggtt ataagactga aaactcaatc aatagcccaa tcctcgccc          49

<210> SEQ ID NO 65
<211> LENGTH: 50
<212> TYPE: DNA
<213> ORGANISM: Artificial Sequence
<220> FEATURE:
<223> OTHER INFORMATION: Synthesized

<400> SEQUENCE: 65
cacatgtata cctaagaaat tggtcccgta gacgtcacag acttacgcca         50

<210> SEQ ID NO 66
<211> LENGTH: 50
<212> TYPE: DNA
<213> ORGANISM: Artificial Sequence
<220> FEATURE:
<223> OTHER INFORMATION: Synthesized

<400> SEQUENCE: 66
cacaacgaaa acaatcttcc ttggcatact ggggagaaag tctgttgtcc         50

<210> SEQ ID NO 67
<211> LENGTH: 50
<212> TYPE: DNA
<213> ORGANISM: Artificial Sequence
<220> FEATURE:
<223> OTHER INFORMATION: Synthesized

<400> SEQUENCE: 67
cacacgaaca tgtccattaa atggcattcc gtttttcgtt ctacatatgc         50

<210> SEQ ID NO 68
<211> LENGTH: 49
<212> TYPE: DNA
<213> ORGANISM: Artificial Sequence
<220> FEATURE:
<223> OTHER INFORMATION: Synthesized

<400> SEQUENCE: 68
cagaacgagg gtcttgtaag actacacctc ctcagtgaca ataatcctg          49

<210> SEQ ID NO 69
<211> LENGTH: 49
<212> TYPE: DNA
<213> ORGANISM: Artificial Sequence
<220> FEATURE:
<223> OTHER INFORMATION: Synthesized

<400> SEQUENCE: 69
cactacagcc tgatatatat gaagaacagg caacaagctt atgcactgg          49

<210> SEQ ID NO 70
<211> LENGTH: 50
<212> TYPE: DNA
<213> ORGANISM: Artificial Sequence
<220> FEATURE:
<223> OTHER INFORMATION: Synthesized

<400> SEQUENCE: 70
gggtacattt atgattctct tataaagaga atatcgtact cttttcccca            50

<210> SEQ ID NO 71
<211> LENGTH: 49
<212> TYPE: DNA
<213> ORGANISM: Artificial Sequence
<220> FEATURE:
<223> OTHER INFORMATION: Synthesized

<400> SEQUENCE: 71
ccaaagtaca ttccaacccc ttatacgtga aacttccagt agtttccta             49

<210> SEQ ID NO 72
<211> LENGTH: 50
<212> TYPE: DNA
<213> ORGANISM: Artificial Sequence
<220> FEATURE:
<223> OTHER INFORMATION: Synthesized

<400> SEQUENCE: 72
cttgaagatc ctcataagac gattaaacaa tccactggat ataatccgga            50

<210> SEQ ID NO 73
<211> LENGTH: 50
<212> TYPE: DNA
<213> ORGANISM: Artificial Sequence
<220> FEATURE:
<223> OTHER INFORMATION: Synthesized

<400> SEQUENCE: 73
cgaatagtgt ccatgattac accaataact gcctgcctat catgtttatg            50

<210> SEQ ID NO 74
<211> LENGTH: 50
<212> TYPE: DNA
<213> ORGANISM: Artificial Sequence
<220> FEATURE:
<223> OTHER INFORMATION: Synthesized

<400> SEQUENCE: 74
ccaagagagt atcggataca cttggaacat agctaactcg aactgtacca            50

<210> SEQ ID NO 75
<211> LENGTH: 48
<212> TYPE: DNA
<213> ORGANISM: Artificial Sequence
<220> FEATURE:
<223> OTHER INFORMATION: Synthesized

<400> SEQUENCE: 75
ccactgataa ataggtaact gtctcatatc tgccaatcat atgccgta              48

<210> SEQ ID NO 76
<211> LENGTH: 50
<212> TYPE: DNA
<213> ORGANISM: Artificial Sequence
<220> FEATURE:
<223> OTHER INFORMATION: Synthesized

<400> SEQUENCE: 76
cccaaattat aaacaattta acacaagcaa aaggaggttc attgctccgc          50

<210> SEQ ID NO 77
<211> LENGTH: 50
<212> TYPE: DNA
<213> ORGANISM: Artificial Sequence
<220> FEATURE:
<223> OTHER INFORMATION: Synthesized

<400> SEQUENCE: 77
caataaactg gtgctaaacc taataccttg tatccaagtt atcctccccc          50

<210> SEQ ID NO 78
<211> LENGTH: 50
<212> TYPE: DNA
<213> ORGANISM: Artificial Sequence
<220> FEATURE:
<223> OTHER INFORMATION: Synthesized

<400> SEQUENCE: 78
ccgaatgaca tccgtagtgg aaccttgctt ttgacactaa gaagctacac          50

<210> SEQ ID NO 79
<211> LENGTH: 50
<212> TYPE: DNA
<213> ORGANISM: Artificial Sequence
<220> FEATURE:
<223> OTHER INFORMATION: Synthesized

<400> SEQUENCE: 79
ccataacaaa taccatagta aagatctgca ttatattata tcggtccacc          50

<210> SEQ ID NO 80
<211> LENGTH: 50
<212> TYPE: DNA
<213> ORGANISM: Artificial Sequence
<220> FEATURE:
<223> OTHER INFORMATION: Synthesized

<400> SEQUENCE: 80
cagaacaaag atcagtagct aaacatatgg tacaaacata ccatctcgca          50

<210> SEQ ID NO 81
<211> LENGTH: 49
<212> TYPE: DNA
<213> ORGANISM: Artificial Sequence
<220> FEATURE:
<223> OTHER INFORMATION: Synthesized

<400> SEQUENCE: 81
cctttagtta ggctagctac aacgattttt ccctgcttgg caacgacac          49

<210> SEQ ID NO 82
<211> LENGTH: 50
<212> TYPE: DNA
<213> ORGANISM: Artificial Sequence
<220> FEATURE:
<223> OTHER INFORMATION: Synthesized

<400> SEQUENCE: 82
ctccctacgt tacaccagcg gtacgaattt tccacgagag gtaatccgca          50

<210> SEQ ID NO 83

```
<211> LENGTH: 36
<212> TYPE: DNA
<213> ORGANISM: Artificial Sequence
<220> FEATURE:
<223> OTHER INFORMATION: Synthesized

<400> SEQUENCE: 83
cggcacctct agttagacac tccggaatttt ttcccc                              36

<210> SEQ ID NO 84
<211> LENGTH: 49
<212> TYPE: DNA
<213> ORGANISM: Artificial Sequence
<220> FEATURE:
<223> OTHER INFORMATION: Synthesized

<400> SEQUENCE: 84
cggcacctct agttagacac tccggaatttt tagcctacca tagtccggt               49

<210> SEQ ID NO 85
<211> LENGTH: 47
<212> TYPE: DNA
<213> ORGANISM: Artificial Sequence
<220> FEATURE:
<223> OTHER INFORMATION: Synthesized

<400> SEQUENCE: 85 cccttttggtt aggctagcta caacgatttt tccctgcttg aattgta                 47

<210> SEQ ID NO 86
<211> LENGTH: 51
<212> TYPE: DNA
<213> ORGANISM: Artificial Sequence
<220> FEATURE:
<223> OTHER INFORMATION: Synthesized

<400> SEQUENCE: 86 cccttttggtt aggctagcta caacgatttt tccctgcttg acctgttacg a            51

<210> SEQ ID NO 87
<211> LENGTH: 48
<212> TYPE: DNA
<213> ORGANISM: Artificial Sequence
<220> FEATURE:
<223> OTHER INFORMATION: Synthesized

<400> SEQUENCE: 87
cctttagtta ggctagctac aacgattttt ccctgcttgg aacgacac                 48

<210> SEQ ID NO 88
<211> LENGTH: 50
<212> TYPE: DNA
<213> ORGANISM: Artificial Sequence
<220> FEATURE:
<223> OTHER INFORMATION: Synthesized

<400> SEQUENCE: 88
catggcttaa tcatcctcaa tagaagacta caagtcgaat atgtcccccc               50

<210> SEQ ID NO 89
<211> LENGTH: 50
<212> TYPE: DNA
<213> ORGANISM: Artificial Sequence
<220> FEATURE:
<223> OTHER INFORMATION: Synthesized

<400> SEQUENCE: 89
```
caacagagcg agtatcaccc cctgtcaata gtcgtatgaa acattgggcc                50

<210> SEQ ID NO 90
<211> LENGTH: 49
<212> TYPE: DNA
<213> ORGANISM: Artificial Sequence
<220> FEATURE:
<223> OTHER INFORMATION: Synthesized

<400> SEQUENCE: 90
taccgacaag gggaattaaa agctagctgg ttatgcaacc cttttcgca                49

<210> SEQ ID NO 91
<211> LENGTH: 49
<212> TYPE: DNA
<213> ORGANISM: Artificial Sequence
<220> FEATURE:
<223> OTHER INFORMATION: Synthesized

<400> SEQUENCE: 91
ctcgaaacag tgatattctg aacaaacggg tactacgtgt tcagccccc                49

<210> SEQ ID NO 92
<211> LENGTH: 50
<212> TYPE: DNA
<213> ORGANISM: Artificial Sequence
<220> FEATURE:
<223> OTHER INFORMATION: Synthesized

<400> SEQUENCE: 92
ccaataacgt aacccggtta gataagcact tagctaagat gtttatcctg                50

<210> SEQ ID NO 93
<211> LENGTH: 50
<212> TYPE: DNA
<213> ORGANISM: Artificial Sequence
<220> FEATURE:
<223> OTHER INFORMATION: Synthesized

<400> SEQUENCE: 93
caatacaatc ggtacgaatc cagaaacata acgttgtttc agaatggtcc                50

<210> SEQ ID NO 94
<211> LENGTH: 50
<212> TYPE: DNA
<213> ORGANISM: Artificial Sequence
<220> FEATURE:
<223> OTHER INFORMATION: Synthesized

<400> SEQUENCE: 94
gcaacaacaa gaaccaagtt acatacacgt tcatctatac tgaaccccca                50

<210> SEQ ID NO 95
<211> LENGTH: 50
<212> TYPE: DNA
<213> ORGANISM: Artificial Sequence
<220> FEATURE:
<223> OTHER INFORMATION: Synthesized

<400> SEQUENCE: 95
cctttgagtt cctaaatgcc gcacggtaag cttggcacac tttgactgta                50

<210> SEQ ID NO 96
<211> LENGTH: 49
<212> TYPE: DNA

```
<213> ORGANISM: Artificial Sequence
<220> FEATURE:
<223> OTHER INFORMATION: Synthesized

<400> SEQUENCE: 96
caaagatctc actttggaaa tgcgaaatat gtatattcgc cctgtctgc            49

<210> SEQ ID NO 97
<211> LENGTH: 50
<212> TYPE: DNA
<213> ORGANISM: Artificial Sequence
<220> FEATURE:
<223> OTHER INFORMATION: Synthesized

<400> SEQUENCE: 97
ccacgtagaa ttatctgatt tataacataa cgcaggataa ctctcgccca           50

<210> SEQ ID NO 98
<211> LENGTH: 48
<212> TYPE: DNA
<213> ORGANISM: Artificial Sequence
<220> FEATURE:
<223> OTHER INFORMATION: Synthesized

<400> SEQUENCE: 98
cacaagaaag tgtcgtctcc agatatttga gtacaaggaa ctacgccc             48

<210> SEQ ID NO 99
<211> LENGTH: 50
<212> TYPE: DNA
<213> ORGANISM: Artificial Sequence
<220> FEATURE:
<223> OTHER INFORMATION: Synthesized

<400> SEQUENCE: 99
catgaagaaa taggacattc tacaggctgg accgttacta tgcctgtagg           50

<210> SEQ ID NO 100
<211> LENGTH: 46
<212> TYPE: DNA
<213> ORGANISM: Artificial Sequence
<220> FEATURE:
<223> OTHER INFORMATION: Synthesized

<400> SEQUENCE: 100
cataggataa tcatggcgat gcttatgacg tgtacatcta tacctt              46

<210> SEQ ID NO 101
<211> LENGTH: 50
<212> TYPE: DNA
<213> ORGANISM: Artificial Sequence
<220> FEATURE:
<223> OTHER INFORMATION: Synthesized

<400> SEQUENCE: 101
cagatgatct tcctttaaag actacccttt aaagaaacat aaggtacccc           50

<210> SEQ ID NO 102
<211> LENGTH: 17
<212> TYPE: RNA
<213> ORGANISM: Human Immunodeficiency Virus

<400> SEQUENCE: 102
ggagagagau gggugcg                                               17
```

```
<210> SEQ ID NO 103
<211> LENGTH: 15
<212> TYPE: RNA
<213> ORGANISM: Human Immunodeficiency Virus

<400> SEQUENCE: 103
gagagagaug ggugc                                                    15

<210> SEQ ID NO 104
<211> LENGTH: 17
<212> TYPE: RNA
<213> ORGANISM: Human Immunodeficiency Virus

<400> SEQUENCE: 104
caguggcaau gagagug                                                  17

<210> SEQ ID NO 105
<211> LENGTH: 15
<212> TYPE: RNA
<213> ORGANISM: Human Immunodeficiency Virus

<400> SEQUENCE: 105
aguggcaaug agagu                                                    15

<210> SEQ ID NO 106
<211> LENGTH: 17
<212> TYPE: RNA
<213> ORGANISM: Human Immunodeficiency Virus

<400> SEQUENCE: 106
gaggauagau ggaacaa                                                  17

<210> SEQ ID NO 107
<211> LENGTH: 15
<212> TYPE: RNA
<213> ORGANISM: Human Immunodeficiency Virus

<400> SEQUENCE: 107
aggauagaug gaaca                                                    15

<210> SEQ ID NO 108
<211> LENGTH: 15
<212> TYPE: RNA
<213> ORGANISM: Human Immunodeficiency Virus

<400> SEQUENCE: 108
gcaagaaaug gagcc                                                    15

<210> SEQ ID NO 109
<211> LENGTH: 15
<212> TYPE: RNA
<213> ORGANISM: Human Immunodeficiency Virus

<400> SEQUENCE: 109
cuauaagaug gguga                                                    15

<210> SEQ ID NO 110
<211> LENGTH: 20
<212> TYPE: RNA
<213> ORGANISM: Feline infectious peritonitis virus

<400> SEQUENCE: 110
uacagcaaca ugggggaaugg                                              20
```

<210> SEQ ID NO 111
<211> LENGTH: 18
<212> TYPE: RNA
<213> ORGANISM: Feline infectious peritonitis virus

<400> SEQUENCE: 111 caugggggaau ggacaggg 18

<210> SEQ ID NO 112
<211> LENGTH: 23
<212> TYPE: RNA
<213> ORGANISM: Artificial Sequence
<220> FEATURE:
<223> OTHER INFORMATION: Synthesized

<400> SEQUENCE: 112
caaauaaaag ggaugaaguc ugg 23

<210> SEQ ID NO 113
<211> LENGTH: 21
<212> TYPE: RNA
<213> ORGANISM: Artificial Sequence
<220> FEATURE:
<223> OTHER INFORMATION: Synthesized

<400> SEQUENCE: 113
aaggaaugaa gucuggcucc g 21

<210> SEQ ID NO 114
<211> LENGTH: 23
<212> TYPE: RNA
<213> ORGANISM: Artificial Sequence
<220> FEATURE:
<223> OTHER INFORMATION: Synthesized

<400> SEQUENCE: 114
auaccgcaaa gucuuugaga auu 23

<210> SEQ ID NO 115
<211> LENGTH: 23
<212> TYPE: RNA
<213> ORGANISM: Artificial Sequence
<220> FEATURE:
<223> OTHER INFORMATION: Synthesized

<400> SEQUENCE: 115
aagucuuuga gaguuuccug cac 23

<210> SEQ ID NO 116
<211> LENGTH: 19
<212> TYPE: RNA
<213> ORGANISM: Artificial Sequence
<220> FEATURE:
<223> OTHER INFORMATION: Synthesized

<400> SEQUENCE: 116
aacaccacca uguccagcc 19

<210> SEQ ID NO 117
<211> LENGTH: 20
<212> TYPE: RNA
<213> ORGANISM: Artificial Sequence
<220> FEATURE:
<223> OTHER INFORMATION: Synthesized

<400> SEQUENCE: 117
ggccuuucac auuguaccgc 20

<210> SEQ ID NO 118
<211> LENGTH: 21
<212> TYPE: RNA
<213> ORGANISM: Artificial Sequence
<220> FEATURE:
<223> OTHER INFORMATION: Synthesized

<400> SEQUENCE: 118
uuguaccgca ucgauaucca c 21

<210> SEQ ID NO 119
<211> LENGTH: 23
<212> TYPE: RNA
<213> ORGANISM: Artificial Sequence
<220> FEATURE:
<223> OTHER INFORMATION: Synthesized

<400> SEQUENCE: 119
gaacauuaca uuauagugac cag 23

<210> SEQ ID NO 120
<211> LENGTH: 14
<212> TYPE: DNA
<213> ORGANISM: Artificial Sequence
<220> FEATURE:
<223> OTHER INFORMATION: Synthesized

<400> SEQUENCE: 120
tccgagccgg acga 14

<210> SEQ ID NO 121
<211> LENGTH: 16
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: 1
<223> OTHER INFORMATION: R = A or G

<400> SEQUENCE: 121
rggctagcta caacga 16

<210> SEQ ID NO 122
<211> LENGTH: 16
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: 1
<223> OTHER INFORMATION: R = A or G
<220> FEATURE:
<221> NAME/KEY: misc_feature
<222> LOCATION: 9
<223> OTHER INFORMATION: H = A, C, or T

<400> SEQUENCE: 122
rggctagcha caacga 16

<210> SEQ ID NO 123
<211> LENGTH: 79
<212> TYPE: DNA

```
<213> ORGANISM: Artificial Sequence
<220> FEATURE:
<223> OTHER INFORMATION: Synthesized
<220> FEATURE:
<221> NAME/KEY: misc_difference
<222> LOCATION: 18
<223> OTHER INFORMATION: N = Adenosine Ribonucleotide

<400> SEQUENCE: 123
ctaatacgac tcactatngg aagagatggc gacatctctt cagcgatgca cgcttgtttt    60
aatgttgcac ccatgttag                                                 79

<210> SEQ ID NO 124
<211> LENGTH: 75
<212> TYPE: DNA
<213> ORGANISM: Artificial Sequence
<220> FEATURE:
<223> OTHER INFORMATION: Synthesized

<400> SEQUENCE: 124
gtgccaagct taccgagtaa cttcgtccgg ctcggragat gggtcgtctg tccttccatc    60
tctagttact ttttc                                                     75

<210> SEQ ID NO 125
<211> LENGTH: 78
<212> TYPE: DNA
<213> ORGANISM: Artificial Sequence
<220> FEATURE:
<223> OTHER INFORMATION: Synthesized

<400> SEQUENCE: 125
gttgccaagc ttaccgggaa aaatcgttgt agctagccta actaggtcgt ctgtccttcc    60
atctctagtt acttttc                                                   78

<210> SEQ ID NO 126
<211> LENGTH: 20
<212> TYPE: DNA
<213> ORGANISM: Artificial Sequence
<220> FEATURE:
<223> OTHER INFORMATION: Synthesized

<400> SEQUENCE: 126
ggaaggacag acgacccatc                                                20

<210> SEQ ID NO 127
<211> LENGTH: 22
<212> TYPE: DNA
<213> ORGANISM: Artificial Sequence
<220> FEATURE:
<223> OTHER INFORMATION: Synthesized

<400> SEQUENCE: 127
gtgccaagct taccgggaaa aa                                             22

<210> SEQ ID NO 128
<211> LENGTH: 22
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: 22
<223> OTHER INFORMATION: N = Adenosine Ribonucleotide

<400> SEQUENCE: 128
```

```
ggaaggacag acgacctagt tn                                              22
```

<210> SEQ ID NO 129
<211> LENGTH: 34
<212> TYPE: DNA
<213> ORGANISM: Artificial Sequence
<220> FEATURE:
<223> OTHER INFORMATION: Synthesized
<400> SEQUENCE: 129

```
gaaaaagtaa ctagagatgg aaggacagac gacc                                 34
```

<210> SEQ ID NO 130
<211> LENGTH: 80
<212> TYPE: DNA
<213> ORGANISM: Artificial Sequence
<220> FEATURE:
<223> OTHER INFORMATION: Synthesized
<400> SEQUENCE: 130

```
cacggttcga atggcgttat gcatcacact attttcatt gaagcaggcc gagccttcca      60
ccttccagcg gtagagaagg                                                 80
```

<210> SEQ ID NO 131
<211> LENGTH: 77
<212> TYPE: DNA
<213> ORGANISM: Artificial Sequence
<220> FEATURE:
<223> OTHER INFORMATION: Synthesized
<400> SEQUENCE: 131

```
cacggttcga atggcatgtt aagttcgtcc cttttagca acatcgatcg gattggtttc      60
cccagcggta gagaagg                                                    77
```

<210> SEQ ID NO 132
<211> LENGTH: 34
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)...(21)
<223> OTHER INFORMATION: Positions 1 to 21 are RNA; the rest of the
      molecule is DNA
<220> FEATURE:
<221> NAME/KEY: misc_feature
<222> LOCATION: 1
<223> OTHER INFORMATION: Optional 5 prime biotinylation
<400> SEQUENCE: 132

```
ggaaaaagua acuagagaug gaagagatgg cgac                                 34
```

<210> SEQ ID NO 133
<211> LENGTH: 72
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (29)...(68)
<223> OTHER INFORMATION: N = A, G, T, or C
<220> FEATURE:
<221> NAME/KEY: misc_difference
<222> LOCATION: 8
<223> OTHER INFORMATION: The "A" at position 8 is a ribonucleotide

<400> SEQUENCE: 133
tcactatagg aagagatggc gacatctcnn nnnnnnnnnn nnnnnnnnnn nnnnnnnnnn    60
nnnnnnnngt ga                                                        72

<210> SEQ ID NO 134
<211> LENGTH: 34
<212> TYPE: DNA
<213> ORGANISM: Artificial Sequence
<220> FEATURE:
<223> OTHER INFORMATION: Synthesized

<400> SEQUENCE: 134
cttccacctt ccgagccgga cgaagttact tttt                                34

<210> SEQ ID NO 135
<211> LENGTH: 24
<212> TYPE: RNA
<213> ORGANISM: Artificial Sequence
<220> FEATURE:
<223> OTHER INFORMATION: Synthesized

<400> SEQUENCE: 135
ggaaaaagua acuagagaug gaag                                           24

<210> SEQ ID NO 136
<211> LENGTH: 31
<212> TYPE: DNA
<213> ORGANISM: Artificial Sequence
<220> FEATURE:
<223> OTHER INFORMATION: Synthesized

<400> SEQUENCE: 136
ctttggttag gctagctaca acgattttc c                                    31

<210> SEQ ID NO 137
<211> LENGTH: 29
<212> TYPE: DNA
<213> ORGANISM: Artificial Sequence
<220> FEATURE:
<223> OTHER INFORMATION: Synthesized

<400> SEQUENCE: 137
ctagttaggc tagctacaac gattttcc                                       29

<210> SEQ ID NO 138
<211> LENGTH: 27
<212> TYPE: DNA
<213> ORGANISM: Artificial Sequence
<220> FEATURE:
<223> OTHER INFORMATION: Synthesized

<400> SEQUENCE: 138
ccaccttccg agccggacga agttact                                        27

<210> SEQ ID NO 139
<211> LENGTH: 44
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: 28
<223> OTHER INFORMATION: N = Adenosine Ribonucleotide

```
<400> SEQUENCE: 139
gggacgaatt ctaatacgac tcactatngg aagagatggc gaca                44

<210> SEQ ID NO 140
<211> LENGTH: 48
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (5)...(44)
<223> OTHER INFORMATION: N = A, G, T, or C

<400> SEQUENCE: 140
tctcnnnnnn nnnnnnnnnn nnnnnnnnnn nnnnnnnnnn nnnngtga         48

<210> SEQ ID NO 141
<211> LENGTH: 48
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: 28
<223> OTHER INFORMATION: N = Adenosine Ribonucleotide

<400> SEQUENCE: 141
gggacgaatt ctaatacgac tcactatngg aagagatggc gacatctc          48

<210> SEQ ID NO 142
<211> LENGTH: 19
<212> TYPE: DNA
<213> ORGANISM: Artificial Sequence
<220> FEATURE:
<223> OTHER INFORMATION: Synthesized

<400> SEQUENCE: 142
gtgacggtaa gcttggcac                                          19

<210> SEQ ID NO 143
<211> LENGTH: 40
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)...(40)
<223> OTHER INFORMATION: N = A, G, T, or C

<400> SEQUENCE: 143
nnnnnnnnnn nnnnnnnnnn nnnnnnnnnn nnnnnnnnnn                   40

<210> SEQ ID NO 144
<211> LENGTH: 34
<212> TYPE: DNA
<213> ORGANISM: Artificial Sequence
<220> FEATURE:
<223> OTHER INFORMATION: Synthesized
<220> FEATURE:
<221> NAME/KEY: misc_RNA
<222> LOCATION: (8)...(19)
<223> OTHER INFORMATION: Positions 8 to 19 are RNA, the remainder of the
      molecule is DNA
<220> FEATURE:
<221> NAME/KEY: misc_feature
<222> LOCATION: 1
```

<223> OTHER INFORMATION: Optional 5 prime biotinylation

<400> SEQUENCE: 144
ggaaaaagua acuagagaug gaagagaugg cgac                          34

<210> SEQ ID NO 145
<211> LENGTH: 15
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: 1
<223> OTHER INFORMATION: Optional 5 prime biotinylation

<400> SEQUENCE: 145
ggaagagatg gcgac                                               15

<210> SEQ ID NO 146
<211> LENGTH: 50
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)...(50)
<223> OTHER INFORMATION: N = A, G, T, or C

<400> SEQUENCE: 146
nnnnnnnnnn nnnnnnnnnn nnnnnnnnnn nnnnnnnnnn nnnnnnnnnn         50

<210> SEQ ID NO 147
<211> LENGTH: 22
<212> TYPE: DNA
<213> ORGANISM: Artificial Sequence
<220> FEATURE:
<223> OTHER INFORMATION: Synthesized

<400> SEQUENCE: 147
gtgccaagct taccgagtaa ct                                       22

<210> SEQ ID NO 148
<211> LENGTH: 21
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: 21
<223> OTHER INFORMATION: Position 21 is ribo uracil, the remainder of
      the molecule is DNA

<400> SEQUENCE: 148
ggaaggacag acgacccatc u                                        21

<210> SEQ ID NO 149
<211> LENGTH: 22
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: 22
<223> OTHER INFORMATION: Position 22 is ribo adenosine, the remainder of
      the molecule is DNA

```
<400> SEQUENCE: 149
ggaaggacag acgacctagt ta                                          22

<210> SEQ ID NO 150
<211> LENGTH: 11
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: 1
<223> OTHER INFORMATION: Optional 5 prime biotinylation

<400> SEQUENCE: 150
ggaaggacag a                                                      11

<210> SEQ ID NO 151
<211> LENGTH: 13
<212> TYPE: DNA
<213> ORGANISM: Artificial Sequence
<220> FEATURE:
<223> OTHER INFORMATION: Synthesized

<400> SEQUENCE: 151
ccgagccgga cga                                                    13

<210> SEQ ID NO 152
<211> LENGTH: 15
<212> TYPE: DNA
<213> ORGANISM: Artificial Sequence
<220> FEATURE:
<223> OTHER INFORMATION: Synthesized

<400> SEQUENCE: 152
ggctagctac aacga                                                  15

<210> SEQ ID NO 153
<211> LENGTH: 15
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: 8
<223> OTHER INFORMATION: M is A or C.

<400> SEQUENCE: 153
ggctagcmac aacga                                                  15

<210> SEQ ID NO 154
<211> LENGTH: 15
<212> TYPE: DNA
<213> ORGANISM: Artificial Sequence
<220> FEATURE:
<223> OTHER INFORMATION: Synthesized

<400> SEQUENCE: 154
ggctagcaac aacga                                                  15

<210> SEQ ID NO 155
<211> LENGTH: 15
<212> TYPE: DNA
<213> ORGANISM: Artificial Sequence
<220> FEATURE:
```

-continued

<223> OTHER INFORMATION: Synthesized

<400> SEQUENCE: 155
ggctagccac aacga                                                    15